(12) United States Patent
Lee et al.

(10) Patent No.: US 8,507,213 B1
(45) Date of Patent: Aug. 13, 2013

(54) METHODS AND COMPOSITIONS FOR TREATING DISEASES TARGETING MABA

(75) Inventors: Candy Lee, Bethesda, MD (US); Steve Ruben, Brookeville, MD (US); Bruno Domon, Zurich (CH); Charles E. Birse, North Potomac, MD (US)

(73) Assignee: Celera Corporation, Alameda, CA (US)

( * ) Notice: Subject to any disclaimer, the term of this patent is extended or adjusted under 35 U.S.C. 154(b) by 650 days.

(21) Appl. No.: 11/594,160

(22) Filed: Nov. 8, 2006

Related U.S. Application Data

(60) Provisional application No. 60/734,261, filed on Nov. 8, 2005, provisional application No. 60/791,878, filed on Apr. 14, 2006.

(51) Int. Cl.
*G01N 33/574* (2006.01)

(52) U.S. Cl.
USPC ....................................................... 435/7.23

(58) Field of Classification Search
USPC .......................................................... 435/7.1
See application file for complete search history.

(56) References Cited

U.S. PATENT DOCUMENTS

| 6,833,247 B2 * | 12/2004 | Sun et al. |
| 2003/0219748 A1 * | 11/2003 | Sun et al. |
| 2007/0065448 A1 * | 3/2007 | Lee et al. |

FOREIGN PATENT DOCUMENTS

| WO | WO03/004989 A2 * | 1/2003 |

OTHER PUBLICATIONS

Bauer et al., "Different Transcriptional Expression of KIAA1324 and its Splicing Variants in Human Carcinoma Cell Lines with different..", Oncology Reports 11, 677-680, 2004.

* cited by examiner

*Primary Examiner* — Brad Duffy
(74) *Attorney, Agent, or Firm* — Celera Corporation

(57) ABSTRACT

Methods and compositions for detecting and treating a disease, particularly cancer, associated with differential expression of Maba in disease cells compared to healthy cells. Also provided are antagonists or agonists of Maba, and methods for screening agents that modulate the Maba level or activity in vivo or in vitro.

3 Claims, 9 Drawing Sheets

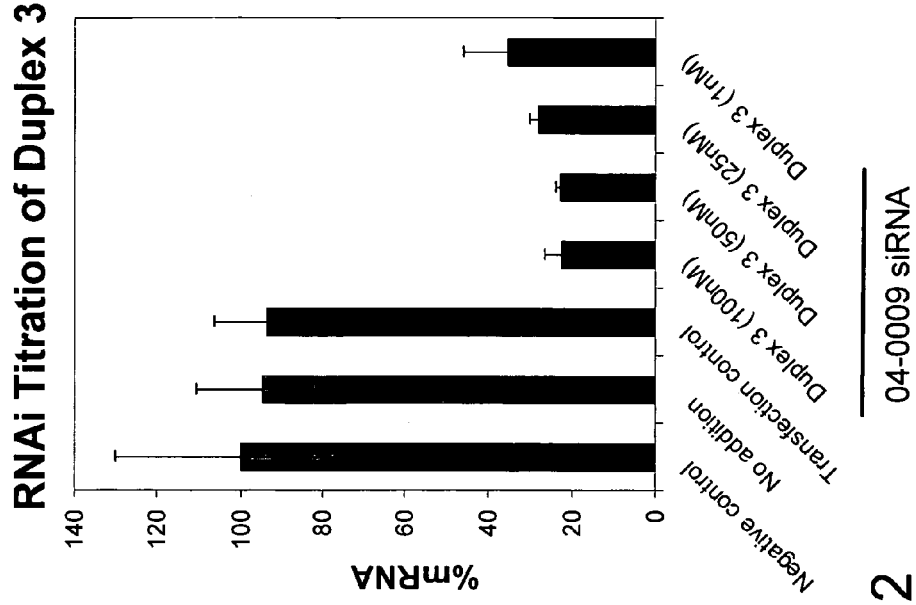
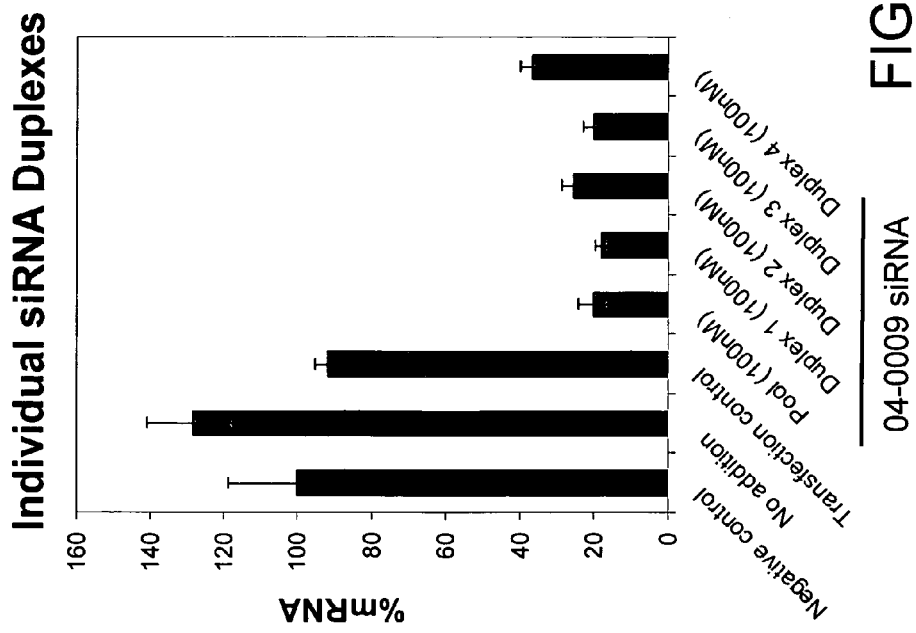
FIGURE 2

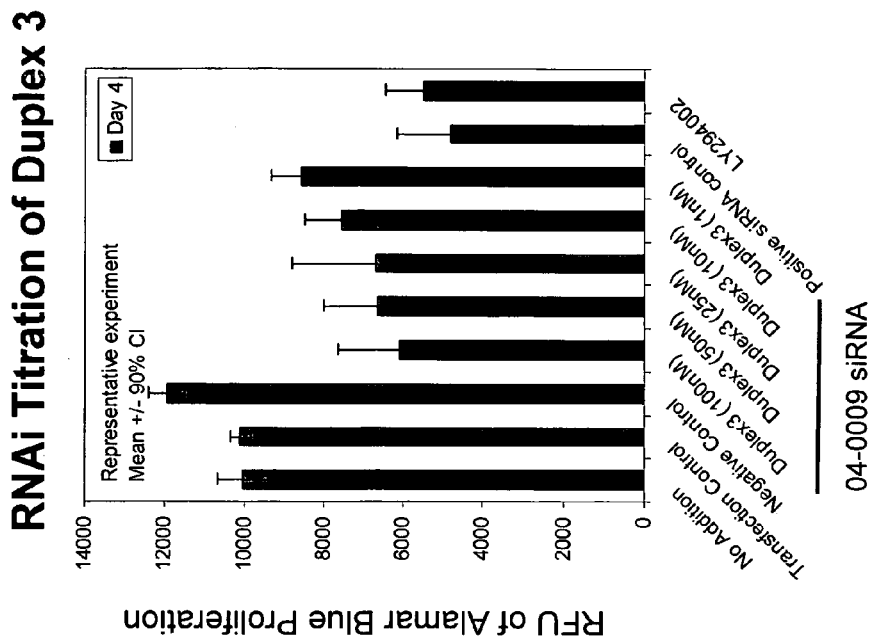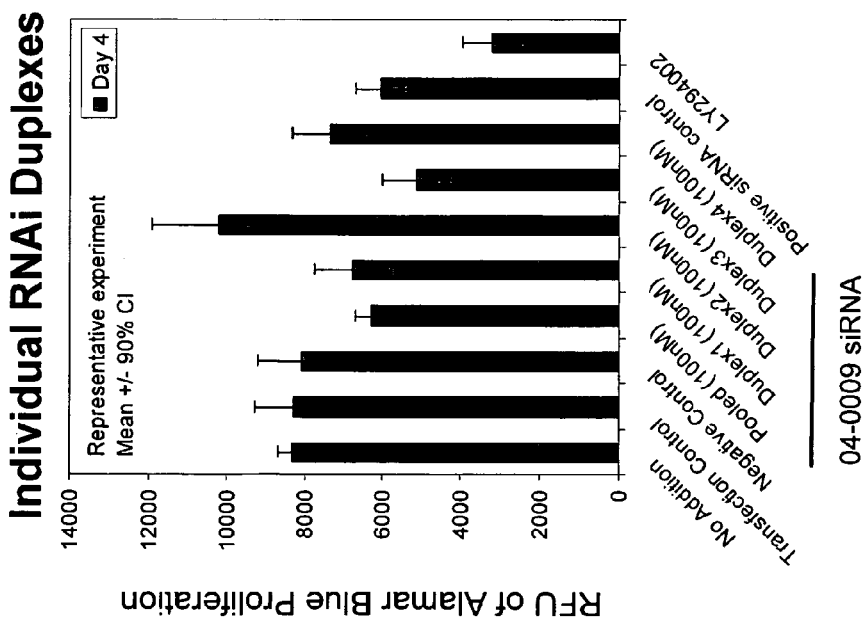
FIGURE 3

Knockdown of Maba (04-0009) Inhibits Proliferation in MCF7 cells
(Normalized over 3 Experiments)

Maba (0009) siRNA Screen Data
Anti-Proliferation Activity

* Reproducible 35% or greater decrease in proliferation

Maba (0009) Individual siRNA Duplex Data
Anti-Proliferation and Apoptosis Activity
MCF-7 Breast Carcinoma mRNA sequence of Maba

```
CGCAGGTGAGCTGCAGAGGCGCGTGTCCCTGCCCCACCCGGGCGGACTCCCTCCCCTTTTTCCGCCTCTGCCAGCAGAAGCAGCAGCCGCAGCACCTGAGC
CGCTACTGCCGCTCACTCAGGACAACGCTATGGCTGAGCCTGGGCACAGCCACCATCTCTCCGCCAGAGTCAGGGGAAGAACTGAGAGGCCCATACCCGGCTGTGG
CGGCTGCTCTGGGCTGGAGGCGCCTTCCAGTGACCCAGGGACCGGAGCTTCATGCCTGCAAAGAGTCTGAGTACCACTATGAGTACACGGGCGTGTGA
CAGCACGGGTTCCAGGTGAGGGTCCGGCCGTGCCCATACCCCGGGCCTGTGCACCAGCCTGACCCGGAGCGAGTGCTCCTTCTCCTGCAACGCC
GGGGAGTTTCTGGATATGAAGGACCAGTCATGTAAGCACTGGTGCTGCTGAGACAGTGCTCAAGATTCGGTTGATGAGTGGAGCTGCCCATGG
CTTTGCCAGCCTCTCAGCCAATGACCAGCCACACTGATGTACGCCGTCAACCTGAAGCAATCTGGCACGTTAACTTCGAATACTATCCAGACTCATCTTTGAGTTTTCG
CACGGACGAATGCACAGTGCCAGCCAATGCAGTCAGATGACTCCAGTGTGATGAAGACCACAGAGAAGGATGGGAATTCCACAGTGTGAGCTAAATCGAGGCAATAATGTCC
TCAGAAATGACCAGTGCCAGCCAATGCAGTCAGATGACTCCAGTGTGATGAAGACCACAGAGAAGGATGGGAATTCCACAGTGTGAGCTAAATCGAGGCAATAATGTCC
TCTATTGGAGAACCACAGCCTTCTCAGTATGGACCAAAGTACCCAAGCCTGTGCTGGTGAGAAACATTGCCATAACAGGGGTGGCCTACACTTCAGATGCTTCCCCTG
CAAACCTGCCACGTATGCAGCAAGCAGGGCTCCTCTTTCTGCAGCCAACTTTGCCAGCCAACTTCTTATTCAAATAAAGGAGAAACTTCTTGCCACCAGTGTGACCCTGACA
AATACTCAGAGAAGGATCTTCTTCGTAACGTGCGCCAGCACCTTGAGGGGCGAGGACCTTGAGGGGCGAGGACCTTGAAGCTGCCCACGCCTGCCACCCAGGCTTCTT
GTACAAATGGCCAAGCCACCTGTGAGGCCGAAAATCTGTAGCGAGGACCTTGAGGGGCGAGGACCTTGAAGCTGCCCACGCCTGCCACCCAGGCTTCTT
CAAAACCAACAACAGCACCTGCCCACAAACATGGAAACGACCGTTCTCAGTGGGATCAACTTCGAGTACAAGGCCATGGGAGGTGGTCAGGAGCAGGAATAAAGAGGTGGC
CAAATGGTGGAACACGCTGCCCACAAACATGGAAACGACCGTTCTCAGTGGGATCAACTTCGAGTACAAGGCCATGGGAGGTGGTGATCACATTTA
CAGCTGCTGGAGCCTCAGACGCCTATACCTAGTCCTATCCATTGAGAACTGTGAGCTCATGGTGTGAATTCTCGCAAGATTTAGACCTCCGGCCCGCCGCAGCCAGATTCATGGTGGATCAATTCTCAGAGACCAGATTCATGGTGATGAGGACTTGAAAAGTACACCAATG
AAGGCAAACAGTCCTATACCTAGTCCTATCCATTGAGGAGGAACACTACCACGAGCTTCACCTGGGCCTTCACCTGAATCATGGTGTGAATTCTCGCAAGATTTAGACCTCCGGCCCGCCGCAGCCAGATTCATGGTGGATCAATTCTCAGAGACCAGATTCATGGTGATGAGGACTTGAAAAGTACACCAATG
ACGTTGCCAAGATCTACTCCATCAATGTCACCATTGACCGAGATTCAGGAACGTGCCAGAGTTCACCACTCTGCTACACCTCTGTGCCACTCGGGCCCTTGTGCCCCT
TTGTCCTGCTGGTTACTATATGTTCACCATTGACCGAGATTCAGGAACGTGCCACTGCCACTGCCCTGTGACCACACAATTCTGAAAGCCTCTGATGTGGGCTCCTGCACCTC
GTGGTCCAGGGACCAAGAACAAGAATCCACTCTGTGCTACAAAGGGCTGAAATACTTCACCCTACGTCTGTGGAAACCAGGTAGGAAATGTCTGTGT
AACACTGTCACTCTTGCTGAGGGCCAAGCTTCACTTCCAAAGGGCTGAAATACTTCACCCTACGTC

METHODS AND COMPOSITIONS FOR TREATING DISEASES TARGETING MABA

FIELD OF THE INVENTION

This invention relates to the fields of molecular biology and oncology. Specifically, the invention provides a molecular marker and a therapeutic agent for use in the diagnosis and treatment of diseases, especially cancer, and particularly pancreatic, lung, breast, kidney, melanoma, ovary, liver, gastric, prostate, and bladder cancers.

BACKGROUND OF THE INVENTION

Cancer currently constitutes the second most common cause of death in the United States, and cancer is difficult to diagnose and treat effectively. Accordingly, there is a need in the art for improved methods for detecting and treating various cancers. The present invention fulfills these needs and further provides other related advantages, such as uses related to the treatment of other diseases.

Lung Cancer

Lung cancer is the second most prevalent type of cancer for both men and women in the United States and is the most common cause of cancer death in both sexes. Lung cancer can result from a primary tumor originating in the lung or a secondary tumor which has spread from another organ such as the bowel or breast. The five-year survival rate for lung cancer continues to be poor at 8-15% survival indicating a large unmet need with regard to more effective treatments and better diagnosis. The estimated total lung cancer deaths in the U.S. in 2003 are 157,200 and the total estimated new cases in 2003 are 171,900. Primary lung cancer is divided into three main types; small cell lung cancer; non-small cell lung cancer; and mesothelioma. Small cell lung cancer is also called "Oat Cell" lung cancer because the cancer cells are a distinctive oat shape. There are three types of non-small cell lung cancer. These are grouped together because they behave in a similar way and respond to treatment differently to small cell lung cancer. The three types are squamous cell carcinoma, adenocarcinoma, and large cell carcinoma. Squamous cell cancer develops from the cells that line the airways. Adenocarcinoma also develops from the cells that line the airways. However, adenocarcinoma develops from a particular type of cell that produces mucus (phlegm). Large cell lung cancer has been thus named because the cells look large and rounded when they are viewed under a microscope. Mesothelioma is a rare type of cancer which affects the covering of the lung called the pleura. Mesothelioma is often caused by exposure to asbestos.

Secondary lung cancer is cancer that has started somewhere else in the body (for example, the breast or bowel) and spread to the lungs. Choice of treatment for secondary lung cancer depends on where the cancer started. In other words, cancer that has spread from the breast should respond to breast cancer treatments and cancer that has spread from the bowel should respond to bowel cancer treatments.

The stage of a cancer indicates how far a cancer has spread. Staging is important because treatment is often decided according to the stage of a cancer. The staging is different for non-small cell and for small cell cancers of the lung.

Non-small cell cancer can be divided into four stages. Stage I is very localized cancer with no cancer in the lymph nodes. Stage II cancer has spread to the lymph nodes at the top of the affected lung. Stage III cancer has spread near to where the cancer started. This can be to the chest wall, the covering of the lung (pleura), the middle of the chest (mediastinum) or other lymph nodes. Stage IV cancer has spread to another part of the body.

Since small cell lung cancer can spread quite early in development of the disease, small cell lung cancers are divided into only two groups. These are: limited disease, that is cancer that can only be seen in one lung and in nearby lymph nodes; and extensive disease, that is cancer that has spread outside the lung to the chest or to other parts of the body. Further, even if spreading is not apparent on the scans, it is likely that some cancer cells will have broken away and traveled through the bloodstream or lymph system. To be safe, it is therefore preferred to treat small cell lung cancers as if they have spread, whether or not secondary cancer is visible. Because surgery is not typically used to treat small cell cancer, except in very early cases, the staging is not as critical as it is with some other types of cancer. Chemotherapy with or without radiotherapy is often employed. The scans and tests done at first will be used later to see how well a patient is responding to treatment.

Procedures used for detecting, diagnosing, monitoring, staging, and prognosticating lung cancer are of critical importance to the outcome of the patient. For example, patients diagnosed with early lung cancer generally have a much greater five-year survival rate as compared to the survival rate for patients diagnosed with distant metastasized lung cancer. New diagnostic methods which are more sensitive and specific for detecting early lung cancer are clearly needed.

Lung cancer patients are closely monitored following initial therapy and during adjuvant therapy to determine response to therapy and to detect persistent or recurrent disease of metastasis. There is clearly a need for a lung cancer marker which is more sensitive and specific in detecting lung cancer, its recurrence, and progression.

Another important step in managing lung cancer is to determine the stage of the patient's disease. Stage determination has potential prognostic value and provides criteria for designing optimal therapy. Generally, pathological staging of lung cancer is preferable over clinical staging because the former gives a more accurate prognosis. However, clinical staging would be preferred were it at least as accurate as pathological staging because it does not depend on an invasive procedure to obtain tissue for pathological evaluation. Staging of lung cancer would be improved by detecting new markers in cells, tissues, or bodily fluids which could differentiate between different stages of invasion.

Breast Cancer

Carcinomas of the breast are the eighth most prevalent form of cancer and fourth among the most common causes of cancer deaths in this country. The incidence of breast cancer has been increasing steadily in the past twenty years in most industrialized countries, exhibiting the characteristics of a growing epidemiological problem. In the year 2000, for example, an estimated 28,600 deaths will be ascribed to this type of cancer and approximately 28,600 new cases will be diagnosed.

Breast cancer is the primary killer of women. One in eight American women will develop breast cancer in her lifetime. An estimated 3 million women in the U.S. today are living with breast cancer, which 2 million have been diagnosed with the disease and 1 million have the disease but do not yet know it.

The incidence of breast cancer in the U.S. has more than doubled in the past 30 years. In 1964, the lifetime risk was one in twenty. Today it's one in eight. Breast cancer is the most commonly diagnosed cancer in women in both America and worldwide. One or more of a variety of treatments such as surgery, radiotherapy, chemotherapy and hormone therapy are used. The treatment course for a certain type of breast cancer is usually selected based on a various prognostic parameters, for example, an analysis of specific tumor markers.(e.g. Porter-Jordan and Lippman, Breast Cancer 8:73-100 (1994)). However, the use of established markers is insufficient to interpret the results and it still results in high mortality which is observed in breast cancer patients.

Kidney (Renal) Cancer

The American Cancer Society estimates that there will be about 36,160 new cases of kidney cancer (22,490 in men and 13,670 in women) in the United States in the year 2005, and about 12,660 people (8,020 men and 4,640 women) will die from this disease. Kidney cancer (also referred to as renal cancer or renal cell carcinoma) mostly affects adults between 50 and 70 years of age. If detected early, kidney cancer is curable. However, symptoms may not appear until the tumor has grown to a large size or metastasized to other organs, at which point treatment is difficult.

The 5-year survival rate for individuals diagnosed with kidney cancer is about 90% for those individuals whose tumor is confined to the kidney, about 60% if it has only spread to nearby tissues, and about 9% if it has spread to distant sites.

The majority of kidney cancers are renal cell carcinomas (which accounts for over 90% of malignant kidney tumors), also known as renal adenocarcinomas or clear cell carcinomas. There are five main types of renal cell carcinoma that are identified based on microscopic examination of cell type: clear cell, papillary, chromophobe, collecting duct, and "unclassified." Kidney cancers are also usually graded on a scale of 1 through 4 to indicate how similar the nuclei of the cancer cells are to the nuclei of normal kidney cells (grade 1 renal cell cancers have cell nuclei that differ very little from normal kidney cell nuclei and generally have a good prognosis, whereas grade 4 renal cell cancer nuclei look considerably different from normal kidney cell nuclei and have a worse prognosis). In addition to grade, kidney cancers are also characterized by stage, which describes the size of the cancer and degree of metastasis. The most commonly used staging system is that of the American Joint Committee on Cancer (AJCC) (also referred to as the TNM system), although the Robson classification is an older system that may be occasionally used.

In additional to renal cell carcinomas, other types of kidney cancers include transitional cell carcinomas, Wilms tumors, and renal sarcomas. Wilms tumors are the most common type of kidney cancer in children and are extremely rare in adults. Benign (non-metastasizing) kidney tumors include renal cell adenomas, renal oncocytomas, and angiomyolipomas.

Risk factors for kidney cancer include the following: age older than 50 years; male (men are twice as likely to get kidney cancer compared to women); cigarette smoking; exposure to asbestos, cadmium, or organic solvents; obesity; a high-fat diet; and von Hippel-Lindau disease (a genetic condition that has a high incidence of kidney cancer).

Symptoms of kidney cancer include hematuria (blood in the urine), abdominal or low back pain, weight loss, fatigue, anemia, fever, high blood pressure, and leg or ankle swelling.

In addition to a detailed medical history, physical examination, and laboratory blood testing, diagnosis of kidney cancer may typically include a computed tomography (CT) scan, ultrasound, magnetic resonance imaging (MRI), intravenous pyelography (a kidney test that utilizes dye and x-rays), or arteriography (a test in which dye is applied to the blood vessels feeding the kidney). To detect metastatic disease, chest X-ray and bone scan may be implemented.

Treatment of kidney cancer in individuals whose tumor is confined to the kidney may involve surgical removal of the kidney (nephrectomy) and surrounding tissue. Radiation therapy may be applied to treat pain and advanced or metastatic kidney cancers or to help shrink a tumor that is causing obstruction. Immunotherapy, such as interferon and interleukin-2, may be used to boost the immune system in patients with advanced kidney cancer.

One promising method for early diagnosis of various forms of cancer is the identification of specific biochemical moieties, termed targets, expressed differentially in cancerous cells. The targets may be either cell surface proteins, cytosolic proteins, or secreted proteins. Antibodies or other biomolecules or small molecules that will specifically recognize and bind to the targets in the cancerous cells potentially provide powerful tools for the diagnosis and treatment of the particular malignancy.

Pancreatic Cancer

Carcinomas of the pancreas are the eighth most prevalent form of cancer and fourth among the most common causes of cancer deaths in this country.

The prognosis for pancreatic carcinoma is, at present, very poor. Pancreatic cancer displays the lowest five-year survival rate among all cancers. Such prognosis results primarily from delayed diagnosis, due in part to the fact that the early symptoms are shared with other more common abdominal ailments. Despite the advances in diagnostic imaging methods like ultrasonography (US), endoscopic ultrasonography (EUS), dualphase spiral computer tomography (CT), magnetic resonance imaging (MRT), endoscopic retrograde cholangiopancreatography (ERCP) and transcutaneous or EUS-guided fine-needle aspiration (FNA), distinguishing pancreatic carcinoma from benign pancreatic diseases, especially chronic pancreatitis, is difficult because of the similarities in radiological and imaging features and the lack of specific clinical symptoms for pancreatic carcinoma.

Substantial efforts have been directed to developing tools useful for early diagnosis of pancreatic carcinomas. Nonetheless, a definitive diagnosis is often dependent on exploratory surgery which is inevitably performed after the disease has advanced past the point when early treatment may be effected.

Prostate Cancer

Prostate diseases include, for example, prostate cancer, as well as benign prostatic hyperplasia (BPH) and prostatitis.

Prostate cancer is the most common non-skin cancer in the United States, where one in six American men develop prostate cancer during his lifetime. About 80% of prostate cancers are diagnosed in men over the age of 65. African-American men are 65% more likely to develop prostate cancer than Caucasian-American men and, furthermore, African-American men tend to get more severe forms of prostate cancer and are more than twice as likely to die from prostate cancer as are Caucasian-American men. Approximately 25% of men with prostate cancer have a family history of prostate cancer. The risk of prostate cancer doubles among men having a first-degree relative with the disease; with two close relatives, a man's risk increases fivefold; and with three or more close relatives, the risk for developing prostate cancer is almost 100%.

Screening for prostate cancer is typically carried out using the prostate specific antigen (PSA) blood test and the digital rectal exam (DRE). The DRE and PSA test cannot confirm whether or not prostate cancer is present, but can indicate whether further testing is needed. If either the DRE or the PSA test indicates the presence of prostate cancer, a transrectal ultrasound (TRUS)—guided biopsy is typically carried out. A biopsy is the only way to confirm or diagnose the presence of prostate cancer. During a biopsy, a TRUS is used to view and guide one or more needles into the prostate to take multiple small samples of tissue from different parts of the prostate. These tissue samples are then examined for the presence of cancer in order to generate a value known as a Gleason Grade, which characterizes the aggressiveness of a particular prostate tumor based on the microscopic appearance of the tissue. Prostate cancer is also staged, which is an assessment of the size and degree of metastases of prostate cancer, using either of two different staging systems (a traditional system classifies the disease into four clinical categories rated A through D; another system exists which is called TNM staging for Tumor-Nodes-Metastases staging). The major treatment options for prostate cancer include hormonal therapy, surgery, radiation therapy, and chemotherapy. Early detection of prostate cancer increases the success rate of these treatment options.

Stomach (Gastric) Cancer

Stomach diseases (also known as gastric diseases) include, for example, stomach cancer and ulcers (ulcers typically involve a break in the tissue lining the stomach).

Stomach cancer is the second most common cancer in the world, behind only skin cancer. Stomach cancer occurs twice as often in men as women and is the most prevalent carcinoma in East Asia, with the rate in Japan being more than seven times that in the United States and accounting for one-third of all cancer deaths in Japan. The average age of individuals afflicted by stomach cancer is 55 years of age.

Several different types of stomach cancer exist. Adenocarcinomas are the most common type of stomach cancer, accounting for 90-95% of malignant tumors of the stomach. Adenocarcinomas typically develop from the epithelial cells that form the innermost lining of the stomach's mucosa. Soft tissue sarcomas are another type of stomach cancer, and soft tissue sarcomas typically develop from the cells of the muscle layer of the stomach. Leiomyosarcoma is the most common type of soft tissue sarcoma that affects the stomach. Another type of sarcoma that can affect the stomach is a gastrointestinal stromal tumor (GIST). Lymphomas can also affect the stomach, of which MALT (mucosa-associated lymphoid tissue) lymphoma is the most common type of lymphoma that affects the stomach. The stomach can also be affected by carcinoid tumors.

Stomach cancer can be diagnosed by an upper gastrointestinal (GI) series, which are x-rays of the esophagus and stomach taken after the patient has drinken a barium solution. Alternatively, an endoscopy can be carried out in which a tube is passed through the esophagus into the stomach and, if desired, a biopsy can be done to obtain a tissue sample for laboratory analysis. Blood tests, chest x-rays, a CT scan of the abdomen, and a check for blood in the patient's stools may also be carried out. Treatment for stomach cancer can include a combination of surgery (termed "gastrectomy"), chemotherapy, and radiation therapy. If the tumor is located close to the small intestine, a partial gastrectomy may be carried out in which a portion of the stomach is removed. If the tumor is located closer to the esophagus, a near-total gastrectomy may be carried out.

Stomach cancer is staged based on how deep the tumor has penetrated the stomach lining, whether it has invaded surrounding lymph nodes, and whether it has metastasized. The system most often used to stage stomach cancer in the United States is the American Joint Commission on Cancer (AJCC) TNM system. T indicates how far the tumor has grown within the stomach and into nearby organs, N indicates the degree to which the tumor has spread to lymph nodes, and M indicates the degree to which the tumor has metastasized to distant organs. In TNM staging, information about the tumor, lymph nodes, and metastasis is combined in a process called stage grouping in order to indicate a stage (represented by stages 0, I, IIA, IIB, III, IVA, and IVB). As the stage increases from 0 to IV, the 5-year relative survival rates for patient's diagnosed with stomach cancer at each stage decreases from about 89% (for stage 0) to about 7-8% (for stages IVA and IVB).

Liver Cancer

Liver diseases include, for example, liver cancer and liver cirrhosis. Liver cancers include malignant liver tumors such as hepatocellular carcinoma (which is the most common type of liver cancer, accounting for about 75% of primary liver cancers) and cholangiocarcinomas, as well as benign liver tumors such as hemangioma, hepatic adenomas, and focal nodular hyperplasia. Among other risk factors (e.g., cirrhosis, such as from alcohol abuse), chronic infection with hepatitis B or hepatitis C virus is a significant liver cancer risk factor.

Furthermore, when cancer is found in the liver, it is often the case that the cancer did not originate in the liver but rather spread to the liver from another cancer that began in a different part of the body. The liver is a common site of metastases for cancers in other organs (such as cancers of the lung, breast, and rectum), particularly since the liver receives blood from the abdominal organs via the portal vein. Tumor cells may detach from the primary cancer, enter the bloodstream or lymphatic channels, and travel to the liver where the tumor cells begin to grow independently.

Liver cancer is rarely diagnosed at an early stage because it usually does not cause symptoms until the cancer is in its later stages and, because no screening tests exist, small tumors are difficult to detect by physical exams. Liver cancers can sometimes be detected using a blood test for alpha-fetoprotein (AFP). However, some tumors do not produce AFP in quantities significant enough to be detected until the tumor is too large to be removed or has metastasized outside the liver. In addition to blood tests for AFP, other diagnostic techniques that may be used to detect liver cancer include ultrasound, CT scans, MRI, angiography, laparoscopy, and biopsy.

Once diagnosed, liver cancer is typically characterized by a stage using Roman numerals I through IV, with a higher numeral indicating a more serious cancer. Stage III is further sub-divided into A, B, and C.

The three main types of treatment for liver cancer are surgery, radiation therapy, and chemotherapy. Currently, surgery offers the only chance of completely curing liver cancer. However, surgery can only completely cure liver cancer if the cancer is small and can be entirely removed. Unfortunately, complete removal of most liver cancers is not possible. Often the cancer is too large by the time it is detected, is present in many different parts of the liver, or has metastasized beyond the liver. Also, many patients who have cirrhosis do not have enough healthy liver remaining for surgery to even be an option. Radiation therapy may be used to shrink a liver tumor or to provide relief from symptoms such as pain, but it can not cure liver cancer and may not prolong survival for liver patients. With regards to chemotherapy, liver cancer does not respond to most drugs. The most successful single drug has been doxorubicin (Adriamycin), however studies generally have not shown that chemotherapy prolongs survival for liver cancer patients.

Only a small fraction of liver cancers are detected at an early stage and can be successfully removed by surgery. Less than 30% of patients who undergo surgery have their cancer completely removed. The overall 5-year relative survival rate from liver cancer is approximately 7%.

Melanoma (Skin Cancer)

Skin cancer includes, for example, melanoma. Melanoma is a type of cancer in which melanocytes (pigment cells) become cancerous. Melanoma generally originates in the skin (cutaneous melanoma), however melanoma can sometimes originate in other areas of the body where melanocytes are present, such as the eyes, meninges, digestive tract, and lymph nodes. Other types of skin cancer include basal cell and squamous cell cancers. Melanoma is much more likely to metastasize and to be fatal than other types of skin cancer.

Melanoma is increasing in occurrence in the United States and worldwide faster than any other cancer, with an approximately 3% annual increase in new cases. The risk for melanoma in the year 2000 was 1 in 74, and melanoma is the most common cancer in individuals aged 20-30 and the most common cause of cancer death in women age 25-30 (and #2 cause of death, after breast cancer, for women age 30-35). Melanoma accounts for 5% of all skin cancers, but 71% of all skin cancer deaths. However, the earlier that melanoma is diagnosed, the better the prognosis for survival.

Maba

Maba (also referred to as Maba1 or KIAA1324) was originally identified in a screen for EGF-containing proteins (*Genomics* (1998) 51: 27-34). Maba has an extracellular domain that is typically larger than 600 amino acids in size and has multiple growth factor receptor domains.

Maba is overexpressed in certain highly metastatic breast and lung cancer cell lines, and the effects of Maba on tumor progression and metastasis may be mediated by the expression level of Maba and/or by variable expression of alternative splice forms (Bauer et al., "Different transcriptional expression of KIAA1324 and its splicing variants in human carcinoma cell lines with different metastatic capacity", *Oncol Rep.* 2004 March; 11(3):677-80). Maba has two splice forms that encode C-terminal truncated proteins and that are only expressed in less metastatic cell lines (*Oncology Reports* (2004) 11; 677-680).

SUMMARY OF THE INVENTION

A diseased, e.g. malignant, cell often differs from a normal cell by a differential expression of one or more proteins. These differentially expressed proteins, and suitable fragments thereof, are useful as markers for the diagnosis and treatment of the disease.

Based on the finding that Maba is differentially expressed in disease cells, especially in cancer, in comparison to normal cells, the present invention provides methods and compositions for treating diseases, especially cancer, and particularly pancreatic, lung, breast, kidney, melanoma, ovary, liver, gastric, prostate, and bladder cancers, using Maba as a target.

In the context of the present invention, the differentially expressed Maba protein (SEQ ID NOS:1-7) and suitable fragments thereof, and nucleic acids encoding said protein (SEQ ID NOS:8-14) and suitable fragments thereof, are referred to herein as Maba protein, Maba peptides or Maba nucleic acids, and collectively as Maba.

The Maba protein of the present invention may serve as a target for one or more classes of therapeutic agents, including antibody therapeutics. Maba protein of the present invention is useful in providing a target for diagnosing a disease, or predisposition to a disease mediated by the peptide, particularly cancer. Accordingly, the invention provides methods for detecting the presence, or levels of, a Maba protein of the present invention in a biological sample such as tissues, cells and biological fluids isolated from a subject.

The diagnosis method may detect Maba nucleic acids, protein, peptides and fragments thereof that are differentially expressed in diseases in a test sample, preferably in a biological sample.

The further embodiment includes but is not limited to, monitoring the disease prognosis (recurrence), diagnosing disease stage, preventing the disease and treating the disease.

Accordingly, the present invention provides a method for diagnosing or detecting a disease (particularly cancer) in a subject comprising: determining the level of Maba in a test sample from said subject, wherein a differential level of said Maba in said sample relative to the level in a control sample from a healthy subject, or the level established for a healthy subject, is indicative of the disease. The test sample includes but is not limited to a biological sample such as tissue, blood, serum or biological fluid.

The diagnostic method of the present invention may be suitable for monitoring the disease progression or the treatment progress.

The diagnostic methods of the present invention may also be suitable for other epithelial-cell related cancers. The present invention further provides an antagonist to Maba protein or peptides and a pharmaceutical composition that comprises the antagonist and a suitable carrier. The antagonist may be used for treating the disease. Preferably, the antagonist is an antibody that specifically binds to a Maba protein or peptide. In another preferred embodiment, the antagonist may be a small molecule that inhibits the function or levels of Maba, or an inhibitory nucleic acid molecule, such as an RNAi or antisense molecule against a Maba nucleic acid.

The present invention provides additionally a pharmaceutical composition comprising an antagonist to Maba of the present invention, and a pharmaceutically acceptable excipient, for treating a disease, particularly cancer.

The present invention further provides a method for treating a disease, particularly cancer, comprising administering to a patient in need of said treatment a therapeutically effective amount of the pharmaceutical composition.

The present invention further provides a method for screening for agents that modulate Maba protein activity, comprising the steps of (i) contacting a candidate agent with a Maba protein, and (ii) assaying for Maba protein activity, wherein a change in said activity in the presence of said agent relative to Maba protein activity in the absence of said agent indicates said agent modulates said Maba protein activity. Candidate agents include but are not limited to protein, peptide, antibody, nucleic acid such as antisense RNA, RNAi fragments, small molecules. RNAi is particularly effective at suppressing gene expression, and is therefore useful for blocking or limiting production of the Maba protein, such as for treating cancer or other diseases.

The screening method may also determine a candidate agent's ability to modulate the expression level of a Maba protein or nucleic acid. The method comprises (i) contacting a candidate agent with a system that is capable of expressing a Maba protein or Maba mRNA, (ii) assaying for the level of a Maba protein or a Maba mRNA, wherein a specific change in said level in the presence of said agent relative to a level in the absence of said agent indicates said agent modulates said Maba level.

The present invention further provides a method to screen for agents that bind to the Maba protein, comprising the steps of (i) contacting a test agent with a Maba protein and (ii) measuring the level of binding of agent to said Maba protein.

DESCRIPTION OF THE SEQUENCE LISTING

The Sequence Listing discloses exemplary Maba protein and nucleic acid sequences. Specifically, SEQ ID NOS:1-7 of the Sequence Listing discloses the amino acid sequence(s) of Maba protein(s), and SEQ ID NOS:8-14 of the Sequence Listing discloses the nucleic acid sequence(s) of Maba transcript(s) that encode Maba protein(s). The Sequence Listing is hereby incorporated by reference pursuant to 37 CFR 1.77 (b)(11).

DESCRIPTION OF THE FIGURES

FIG. 2. Knockdown of Maba mRNA in MCF-7 Breast Cancer Cells.

FIG. 3. Knockdown of Maba mRNA Inhibits Proliferation of MCF-7 Breast Cancer Cells.

FIG. 9. mRNA sequence of Maba (SEQ ID NO:17), indicating siRNA target regions.

DETAILED DESCRIPTION OF THE PREFERRED EMBODIMENTS

1. Maba Protein and Peptides

Figure 1:
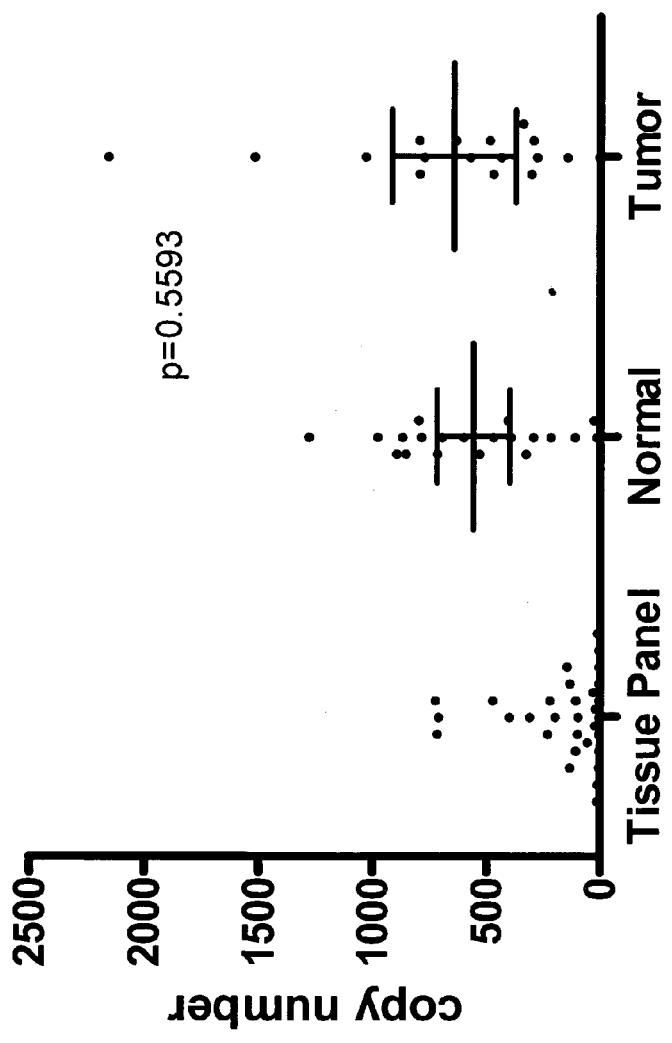
FIG. 1. Maba mRNA Expression Analysis in Breast Tumor Tissues.
Figure 4:
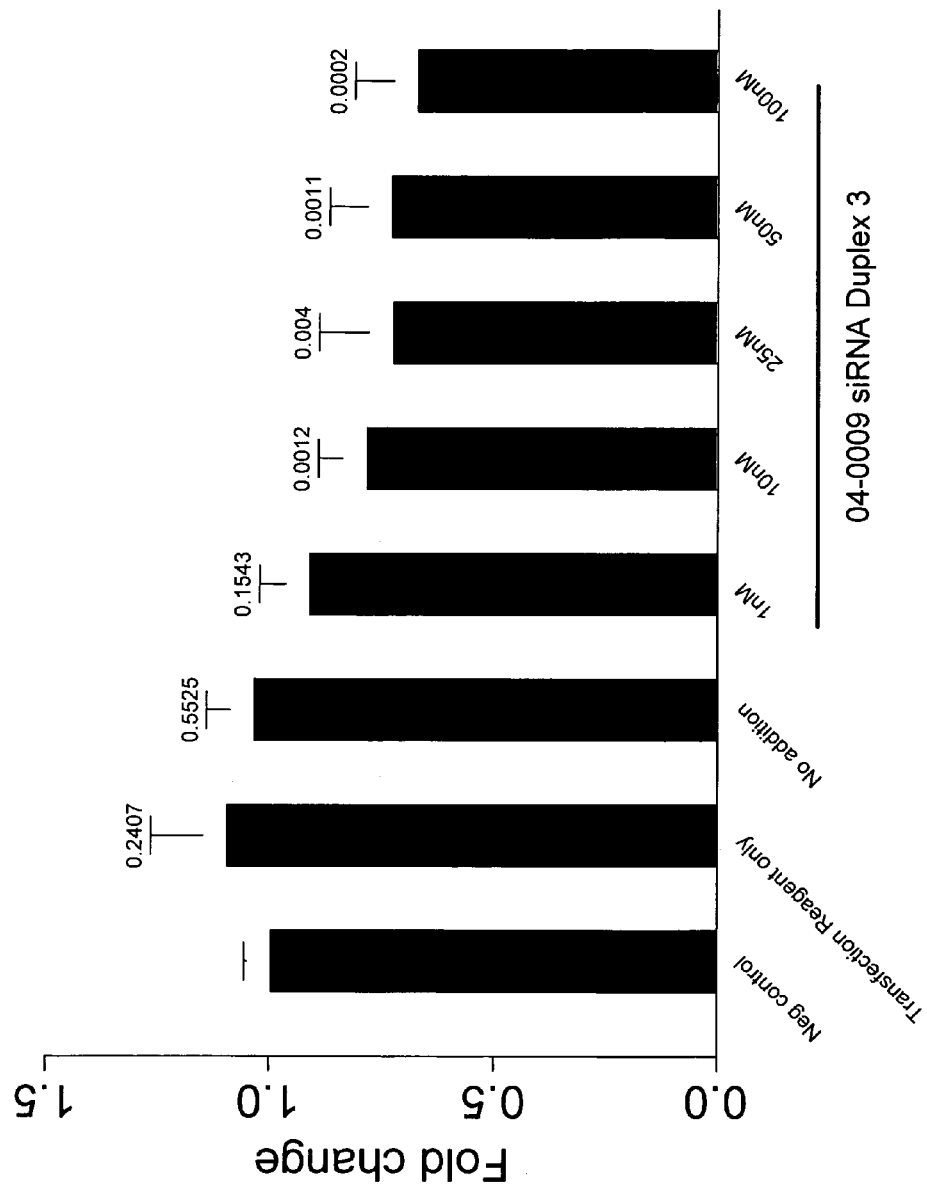
FIG. 4. Knockdown of Maba Inhibits Proliferation in MCF7 cells (normalized over three experiments).

The present invention provides isolated Maba peptide and protein molecules that consisting of, consisting essentially of, or comprising the amino acid sequence of SEQ ID NOS:1-7, respectively encoded by the nucleic acid molecules having the nucleotide sequences of SEQ ID NOS:8-14, as well as all obvious variants of these peptides that are within the art to make and use. Some of these variants are described in detail below.

A Maba peptide or protein can be attached to heterologous sequences to form chimeric or fusion proteins. Such chimeric and fusion proteins comprise a peptide operatively linked to a heterologous protein having an amino acid sequence not substantially homologous to the peptide. "Operatively linked" indicates that the peptide and the heterologous protein are fused in-frame. The heterologous protein can be fused to the N-terminus or C-terminus of the peptide.

In some uses, the fusion protein does not affect the activity of the peptide or protein per se. For example, the fusion protein can include, but is not limited to, fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Maba proteins or peptides. In certain host cells (e.g., mammalian host cells), expression and/or secretion of a protein can be increased by using a heterologous signal sequence.

A chimeric or fusion Maba protein or peptide can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A Maba-encoding nucleic acid can be cloned into such an expression vector such that the fusion moiety is linked in-frame to the Maba protein or peptide.

Variants of the Maba protein can readily be identified/made using molecular techniques and the sequence information disclosed herein. Further, such variants can readily be distinguished from other peptides based on sequence and/or structural homology to the Maba peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48): 444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acids and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215: 403-10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389-3402 (1997)). When utilizing BLAST and gapped BLAST programs, the default parameters of the respective programs (e.g., XBLAST and NBLAST) can be used.

Allelic variants of a Maba peptide can readily be identified as being a human protein having a high degree (significant) of sequence homology/identity to at least a portion of the Maba peptide as well as being encoded by the same genetic locus as the Maba peptide provided herein. Genetic locus can readily be determined based on the genomic information. As used herein, two proteins (or a region of the proteins) have significant homology when the amino acid sequences are typically at least about 70-80%, 80-90%, and more typically at least about 90-95% or more homologous. A significantly homologous amino acid sequence, according to the present invention, will be encoded by a nucleic acid sequence that will hybridize to a Maba peptide encoding nucleic acid molecule under stringent conditions as more fully described below.

Paralogs of a Maba peptide can readily be identified as having some degree of significant sequence homology/identity to at least a portion of the Maba peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a Maba peptide encoding nucleic acid molecule under moderate to stringent conditions as more fully described below.

Orthologs of a Maba peptide can readily be identified as having some degree of significant sequence homology/identity to at least a portion of the Maba peptide as well as being encoded by a gene from another organism. Preferred orthologs will be isolated from mammals, preferably primates, for the development of human therapeutic targets and agents. Such orthologs will be encoded by a nucleic acid sequence that will hybridize to a Maba peptide-encoding nucleic acid molecule under moderate to stringent conditions, as more fully described below, depending on the degree of relatedness of the two organisms yielding the proteins.

Non-naturally occurring variants of the Maba peptides of the present invention can readily be generated using recombinant techniques. Such variants include, but are not limited to deletions, additions and substitutions in the amino acid sequence of the Maba peptide. For example, one class of substitutions is conserved amino acid substitution. Such substitutions are those that substitute a given amino acid in a Maba peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Variant Maba peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity such as Maba activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899-904 (1992); de Vos et al. Science 255:306-312 (1992)).

The present invention further provides fragments of Maba, in addition to and peptides that comprise and consist of such fragments. As used herein, a fragment comprises at least 8, 10, 12, 14, 16, 18, 20 or more contiguous amino acid residues from Maba. Such fragments can be chosen based on the ability to retain one or more of the biological activities of Maba or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of Maba, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis).

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Maba are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (Meth. Enzymol. 182: 626-646 (1990)) and Rattan et al. (Ann. N.Y. Acad. Sci. 663:48-62 (1992)).

Accordingly, the Maba of the present invention also encompass derivatives or analogs in which a substituted amino acid residue is not one encoded by the genetic code, in which a substituent group is included, in which the mature Maba is fused with another compound, such as a compound to increase the half-life of Maba (for example, polyethylene glycol), or in which the additional amino acids are fused to the mature Maba, such as a leader or secretory sequence or a sequence for purification of the mature Maba or a pro-protein sequence.

2. Antibodies Against Maba Protein or Fragments Thereof

Antibodies that selectively bind to the Maba protein or peptides of the present invention can be made using standard procedures known to those of ordinary skills in the art. The term "antibody" is used in the broadest sense, and specifically covers monoclonal antibodies (including full length monoclonal antibodies), polyclonal antibodies, multispecific antibodies (e.g., bispecific antibodies), humanized antibody and antibody fragments (e.g., Fab, F(ab').sub.2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules that lack antigen specificity.

As used herein, antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains. Chothia et al., J. Mol. Biol. 186, 651-63 (1985); Novotny and Haber, Proc. Natl. Acad. Sci. USA 82 4592-4596 (1985).

An "isolated" antibody is one which has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain. Isolated antibody includes the antibody in situ within recombinant cells since at least one component of the antibody's natural environment will not be present. Ordinarily, however, isolated antibody will be prepared by at least one purification step.

An "antigenic region" or "antigenic determinant" or an "epitope" includes any protein determinant capable of specific binding to an antibody. This is the site on an antigen to which each distinct antibody molecule binds. Epitopic determinants usually consist of active surface groupings of molecules such as amino acids or sugar side chains and usually have specific three-dimensional structural characteristics, as well as charge characteristics.

"Antibody specificity," is an antibody, which has a stronger binding affinity for an antigen from a first subject species than it has for a homologue of that antigen from a second subject species. Normally, the antibody "bind specifically" to a human antigen (i.e., has a binding affinity (Kd) value of no more than about $1\times10^{-7}$ M, preferably no more than about $1\times10^{-8}$ M and most preferably no more than about $1\times10^{-9}$ M) but has a binding affinity for a homologue of the antigen from a second subject species which is at least about 50 fold, or at least about 500 fold, or at least about 1000 fold, weaker than its binding affinity for the human antigen. The antibody can be of any of the various types of antibodies as defined above, but preferably is a humanized or human antibody (Queen et al., U.S. Pat. Nos. 5,530,101; 5,585,089; 5,693,762; and 6,180,370).

The present invention provides an "antibody variant," which refers to an amino acid sequence variant of an antibody wherein one or more of the amino acid residues have been modified. Such variant necessarily have less than 100% sequence identity or similarity with the amino acid sequence having at least 75% amino acid sequence identity or similarity with the amino acid sequence of either the heavy or light chain variable domain of the antibody, more preferably at least 80%, more preferably at least 85%, more preferably at least 90%, and most preferably at least 95%. Since the method of the invention applies equally to both polypeptides, antibodies and fragments thereof, these terms are sometimes employed interchangeably.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of crosslinking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

An "Fv" fragment is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment [also designated as F(ab)] also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The present invention further provides monoclonal antibody, polyclonal antibody as well as humanized antibody. In general, to generate antibodies, an isolated peptide is used as an immunogen and is administered to a mammalian organism, such as a rat, rabbit or mouse. The full-length protein, an antigenic peptide fragment or a fusion protein of the Maba protein can be used. Particularly important fragments are those covering functional domains. Many methods are known for generating and/or identifying antibodies to a given target peptide. Several such methods are described by Harlow, Antibodies, Cold Spring Harbor Press, (1989).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" antibody indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al., Nature 352: 624-628 (1991), as well as in Marks et al., J. Mol. Biol. 222: 581-597 (1991). For detailed procedures for making a monoclonal antibody, see the Example below.

"Humanized" forms of non-human (e.g. murine or rabbit) antibodies are chimeric immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-327 (1988) and Presta, Curr. Op. Struct. Biol. 2, 593-596 (1992).

Polyclonal antibodies may be prepared by any known method or modifications of these methods including obtaining antibodies from patients. For example, a complex of an immunogen such as Maba protein, peptides or fragments thereof and a carrier protein is prepared and an animal is immunized by the complex according to the same manner as that described with respect to the above monoclonal antibody preparation and the description in the Example. A serum or plasma containing the antibody against the protein is recovered from the immunized animal and the antibody is separated and purified. The gamma globulin fraction or the IgG antibodies can be obtained, for example, by use of saturated ammonium sulfate or DEAE SEPHADEX, or other techniques known to those skilled in the art.

The antibody titer in the antiserum can be measured according to the same manner as that described above with respect to the supernatant of the hybridoma culture. Separation and purification of the antibody can be carried out according to the same separation and purification method of antibody as that described with respect to the above monoclonal antibody and in the Example.

The protein used herein as the immunogen is not limited to any particular type of immunogen. In one aspect, antibodies are preferably prepared from regions or discrete fragments of the Maba protein. Antibodies can be prepared from any region of the peptide as described herein. In particular, they are selected from a group consisting of SEQ ID NOS:1-7 and fragments thereof. An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness.

Antibodies may also be produced by inducing production in the lymphocyte population or by screening antibody libraries or panels of highly specific binding reagents as disclosed in Orlandi et al. (1989; Proc Natl Acad Sci 86:3833-3837) or Winter et al. (1991; Nature 349:293-299). A protein may be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art. Smith G. P., 1991, Curr. Opin. Biotechnol. 2: 668-673.

The antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibody can be also made recombinantly. When using recombinant techniques, the antibody variant can be produced intracellularly, in the periplasmic space, or directly secreted into the medium. If the antibody variant is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody variant is secreted into the medium, supernatants from such expression systems are generally first concentrated using a commercially available protein concentration filter, for example, an Amicon or Millipore PELLICON ultrafiltration unit. A protease inhibitor such as PMSF may be included in any of the foregoing steps to inhibit proteolysis and antibiotics may be included to prevent the growth of adventitious contaminants.

The antibodies or antigen binding fragments may also be produced by genetic engineering. The technology for expression of both heavy and light chain genes in E. coli is the subject the following PCT patent applications; publication number WO 901443, WO901443, and WO 9014424 and in Huse et al., 1989 Science 246:1275-1281. The general recombinant methods are well known in the art.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .delta.1, .delta.2 or .delta.4 heavy chains (Lindmark et al., J. Immunol. Meth. 62: 1-13 (1983)). Protein G is recommended for all mouse isotypes and for human .delta.3 (Guss et al., EMBO J. 5: 1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the BAKERBOND ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

3. Maba Nucleic Acid Molecules

Isolated Maba nucleic acid molecules of the present invention consist of, consist essentially of, or comprise a nucleotide sequence that encodes Maba peptides of the present invention, an allelic variant thereof, or an ortholog or paralog thereof. As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding Maba peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the proteins of the present invention as well as nucleic acid molecules that encode obvious variants of Maba protein of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60-70%, 70-80%, 80-90%, and more typically at least about 90-95% or more homologous to the nucleotide sequence. Such nucleic acid molecules can readily be identified as being able to hybridize under moderate to stringent conditions, to the nucleotide sequence shown in the Sequence Listing or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65C. Examples of moderate to low stringency hybridization conditions are well known in the art.

4. Vectors and Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequences to which the nucleic acid molecules described herein can be operably linked include promoters for directing mRNA transcription. These include, but are not limited to, the left promoter from bacteriophage, the lac, TRP, and TAC promoters from E. coli, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., Molecular Cloning: A Laboratory Manual. 3rd. ed., Cold Spring Harbor Laboratory Press, Cold Spring Harbor, N.Y., (2001).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y., (2001).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, E. coli, Streptomyces, and Salmonella typhimurium. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein; increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al., Gene 69:301-315 (1988)) and pET 11d (Studier et al., Gene Expression Technology: Methods in Enzymology 185:60-89 (1990)).

Recombinant protein expression can be maximized in host bacteria by providing a genetic background wherein the host cell has an impaired capacity to proteolytically cleave the recombinant protein. (Gottesman, S., Gene Expression Technology: Methods in Enzymology 185, Academic Press, San Diego, Calif. (1990) 119-128). Alternatively, the sequence of the nucleic acid molecule of interest can be altered to provide preferential codon usage for a specific host cell, for example E. coli. (Wada et al., Nucleic Acids Res. 20:2111-2118 (1992)).

The nucleic acid molecules can also be expressed by expression vectors suitable in a yeast host. Examples of vectors for expression in yeast e.g., S. cerevisiae include pYepSec1 (Baldari, et al., EMBO J. 6:229-234 (1987)), pMFa (Kurjan et al., Cell 30:933-943 (1982)), pJRY88 (Schultz et al., Gene 54:113-123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology 170:31-39 (1989)).

In certain embodiments of the invention, the nucleic acid molecules described herein are expressed in mammalian cells using mammalian expression vectors. Examples of mammalian expression vectors include pCDM8 (Seed, B. Nature 329:840 (1987)) and pMT2PC (Kaufman et al., EMBO J. 6:187-195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. Molecular Cloning: A Laboratory Manual. 3rd. ed., Cold Spring Harbor Laboratory Press, Cold Spring Harbor, N.Y., (2001).

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (Molecular Cloning: A Laboratory Manual. 3rd. ed., Cold Spring Harbor Laboratory Press, Cold Spring Harbor, N.Y., (2001).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which may be difficult to achieve with a multi-transmembrane domain containing protein such as Maba, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

The recombinant host cells expressing the peptides described herein have a variety of uses. First, the cells are useful for producing Maba protein or peptide that can be further purified to produce desired amounts of Maba protein or fragments. Thus, host cells containing expression vectors are useful for peptide production.

Host cells are also useful for conducting cell-based assays involving the Maba protein or Maba protein fragments, such as those described above as well as other formats known in the art. Thus, a recombinant host cell expressing a native Maba protein is useful for assaying compounds that stimulate or inhibit Maba protein function.

Host cells are also useful for identifying Maba protein mutants in which these functions are affected. If the mutants naturally occur and give rise to a pathology, host cells containing the mutations are useful to assay compounds that have a desired effect on the mutant Maba protein (for example, stimulating or inhibiting function) which may not be indicated by their effect on the native Maba protein.

5. Detection and Diagnosis in General

As used herein, a "biological sample" can be collected from tissues, blood, sera, cell lines or biological fluids such as, plasma, interstitial fluid, urine, cerebrospinal fluid, and the like, containing cells. In preferred embodiments, a biological sample comprises cells or tissues suspected of having diseases (e.g., cells obtained from a biopsy).

As used herein, a "differential level" is defined as the level of Maba protein or nucleic acids in a test sample either above or below the level in control samples, wherein the level of control samples is obtained either from a control cell line, a normal tissue or body fluids, or combination thereof, from a healthy subject. While the protein is overexpressed, the expression of Maba is preferably greater than about 20%, or preferably greater than about 30%, and most preferably greater than about 50% or more of disease sample, at a level that is at least two fold, and preferably at least five fold, greater than the level of expression in control samples, as determined using a representative assay provided herein. While the protein is under expressed, the expression of Maba is preferably less than about 20%, or preferably less than 30%, and most preferably less than about 50% or more of the disease sample, at a level that is at least 0.5 fold, and preferably at least 0.2 fold less than the level of the expression in control samples, as determined using a representative assay provided herein.

As used herein, a "subject" can be a mammalian subject or non mammalian subject, preferably, a mammalian subject. A mammalian subject can be human or non-human, preferably human. A healthy subject is defined as a subject without detectable diseases or associated pathologies by using conventional diagnostic methods.

As used herein, the "disease(s)" preferably include cancer, particularly pancreatic, lung, breast, kidney, melanoma, ovary, liver, gastric, prostate, and bladder cancers, and associated diseases and pathologies.

6. Treatment in General

This invention further pertains to novel agents identified by the screening assays described below. It is also within the scope of this invention to use an agent identified for treatment purposes. For example, an agent identified as described herein (e.g., a Maba-modulating agent, an antisense Maba nucleic acid molecule, a Maba-RNAi fragment, a Maba-specific antibody, or a Maba-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

Modulators of Maba protein activity identified according to these drug screening assays can be used to treat a subject with a disorder mediated by Maba, e.g. by treating cells or tissues that express Maba at a differential level. Methods of treatment include the steps of administering a modulator of Maba activity in a pharmaceutical composition to a subject in need of such treatment.

The following terms, as used in the present specification and claims, are intended to have the meaning as defined below, unless indicated otherwise.

"Treat," "treating" or "treatment" of a disease includes: (1) inhibiting the disease, i.e., arresting or reducing the development of the disease or its clinical symptoms, or (2) relieving the disease, i.e., causing regression of the disease or its clinical symptoms.

The term "prophylaxis" is used to distinguish from "treatment," and to encompass both "preventing" and "suppressing," it is not always possible to distinguish between "preventing" and "suppressing," as the ultimate inductive event or events may be unknown, latent, or the patient is not ascertained until well after the occurrence of the event or events. Therefore, the term "protection," as used herein, is meant to include "prophylaxis."

A "therapeutically effective amount" means the amount of an agent that, when administered to a subject for treating a disease, is sufficient to effect such treatment for the disease. The "therapeutically effective amount" will vary depending on the agent, the disease and its severity and the age, weight, etc., of the subject to be treated.

In one embodiment, when decreased expression or activity of the protein is desired, an inhibitor, antagonist, antibody and the like or a pharmaceutical agent containing one or more of these molecules may be delivered. Such delivery may be effected by methods well known in the art and may include delivery by an antibody specifically targeted to the protein.

In another embodiment, when increased expression or activity of the protein is desired, the protein, an agonist, an enhancer and the like or a pharmaceutical agent containing one or more of these molecules may be delivered. Such delivery may be effected by methods well known in the art.

While it is possible for the modulating agent to be administered in a pure or substantially pure form, it is preferable to present it as a pharmaceutical composition, formulation or preparation with a carrier. The formulations of the present invention, both for veterinary and for human use, comprise a suitable active Maba modulating agent, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

Suitable pharmaceutical carriers include proteins such as albumins (e.g., U.S. Pat. No. 4,507,234, to Kato et al.), peptides and polysaccharides such as aminodextran (e.g., U.S. Pat. No. 4,699,784, to Shih et al.), or water. A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, metal oxide, radionuclide. For example, U.S. Pat. No. 4,673,562, to Davison et al. discloses representative chelating compounds and their synthesis.

All methods include the step of bringing into association the active ingredient with the carrier, which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions, which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids, which may be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the antibody of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate anti-Maba antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

7. Diagnosis, Treatment and Screening Methods Using Maba Nucleic Acids a. General Aspects The nucleic acid molecules of the present invention are useful for probes, primers, chemical intermediates, and in biological assays. The nucleic acid molecules are useful as a hybridization probe for messenger RNA, transcript/cDNA and genomic DNA to detect or isolate full-length cDNA and genomic clones encoding Maba protein or peptide of the invention, or variants thereof.

The probe can correspond to any sequence along the entire length of the nucleic acid molecules of SEQ ID NOS:8-14. Accordingly, it could be derived from 5' noncoding regions, the coding region, and 3' noncoding regions.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. The nucleic acid molecules are also useful for expressing antigenic portions of the proteins.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

In vitro techniques for detection of mRNA include Northern hybridizations and in situ hybridizations. In vitro techniques for detecting DNA include Southern hybridizations and in situ hybridization.

b. Diagnosis Methods

The nucleic acid molecules are also useful as hybridization probes for determining the presence, level, form and distribution of nucleic acid expression. The probes can be used to detect the presence of, or to determine levels of, a specific nucleic acid molecule in cells, tissues, and in organisms. Accordingly, probes corresponding to the peptides described herein can be used to assess expression and/or gene copy number in a given cell, tissue, or organism. These uses are relevant for diagnosis of disorders involving an increase or decrease in Maba protein expression relative to normal results.

Probes can be used as a part of a diagnostic test kit for identifying cells or tissues that express Maba protein differentially, such as by measuring a level of a Maba-encoding nucleic acid in a sample of cells from a subject e.g., mRNA or genomic DNA, or determining if a Maba gene has been mutated.

The invention also encompasses kits for detecting the presence of Maba nucleic acid in a biological sample. For example, the kit can comprise reagents such as a labeled or labelable nucleic acid or agent capable of detecting Maba nucleic acid in a biological sample; means for determining the amount of Maba nucleic acid in the sample; and means for comparing the amount of Maba nucleic acid in the sample with a standard. The compound or agent can be packaged in a suitable container. The kit can further comprise instructions for using the kit to detect Maba protein mRNA or DNA.

c. Screening Method Using Nucleic Acids

Nucleic acid expression assays are useful for drug screening to identify compounds that modulate Maba nucleic acid expression.

The invention thus provides a method for identifying a compound that can be used to treat a disease associated with differential expression of the Maba gene, particularly cancer. The method typically includes assaying the ability of the compound to modulate the expression of Maba nucleic acid and thus identifying a compound that can be used to treat a disorder characterized by undesired Maba nucleic acid expression. The assays can be performed in cell-based and cell-free systems. Cell-based assays include cells naturally expressing Maba nucleic acid or recombinant cells genetically engineered to express specific nucleic acid sequences.

The assay for Maba nucleic acid expression can involve direct assay of nucleic acid levels, such as mRNA levels, or on collateral compounds involved in the signal pathway. Further, the expression of genes that are up- or down-regulated in response to the Maba protein signal pathway can also be assayed. In this embodiment the regulatory regions of these genes can be operably linked to a reporter gene such as luciferase.

Thus, modulators of Maba gene expression can be identified in a method wherein a cell is contacted with a candidate compound or agent and the expression of mRNA determined. The level of expression of Maba mRNA in the presence of the candidate compound or agent is compared to the level of expression of Maba mRNA in the absence of the candidate compound or agent. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

d. Methods of Monitoring Treatment

The nucleic acid molecules are also useful for monitoring the effectiveness of modulating compounds or agents on the expression or activity of the Maba gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

e. Treatment Using Nucleic Acid

The nucleic acid molecules are useful to design antisense constructs to control Maba gene expression in cells, tissues, and organisms. A DNA antisense nucleic acid molecule is designed to be complementary to a region of the gene involved in transcription, preventing transcription and hence production of Maba protein. An antisense RNA or DNA nucleic acid molecule would hybridize to the mRNA and thus block translation of mRNA into Maba protein.

The nucleic acid of the present invention may also be used to specifically suppress gene expression by methods such as RNA interference (RNAi), which may also include cosuppression and quelling. This and antisense RNA or DNA of gene suppression are well known in the art. A review of this technique is found in Science 288:1370-1372, 2000. RNAi also operates on a post-transcriptional level and is sequence specific, but suppresses gene expression far more efficiently than antisense RNA. RNAi fragments, particularly double-stranded (ds) RNAi, can be also used to generate loss-of-function phenotypes.

The present invention relates to isolated RNA molecules (double-stranded; single-stranded) of from about 21 to about 25 nucleotides which mediate RNAi. As used herein, about 21 to about 25 nt includes nucleotides 17, 18, 19, 20, 21, 22, 23, 24, 25, 26, 27, 28 and 29 nucleotides in length. The isolated RNAs of the present invention mediate degradation of mRNA, the transcriptional product of a gene. Such mRNA is also referred to herein as mRNA to be degraded. As used herein, the terms RNA, RNA molecule(s), RNA segment(s) and RNA fragment(s) are used interchangeably to refer to RNA that mediates RNA interference. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the 21-25 nt RNA or internally (at one or more nucleotides of the RNA). Nucleotides in the RNA molecules of the present invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nucleotides of the present invention need only be sufficiently similar to natural RNA that it has the ability to mediate RNAi. As used herein the phrase "mediates RNAi" refers to the ability to distinguish which RNAs are to be degraded by the RNAi machinery or process. RNA that mediates RNAi interacts with the RNAi machinery such that it directs the degradation of particular mRNAs. Such RNA may include RNAs of various structure, including short hairpin RNA.

In one embodiment, the present invention relates to RNA molecules of about 21 to about 25 nucleotides that direct cleavage of specific mRNA to which their sequence corresponds. It is not necessary that there be perfect correspondence of the sequences, but the correspondence must be sufficient to enable the RNA to direct RNAi cleavage of the target mRNA (Holen et al. (2005) Nucleic Acids Res. 33, 4704-4710). In a particular embodiment, the 21-25 nt RNA molecules of the present invention comprise a 3' hydroxyl group.

The present invention relates to 21-25 nt RNAs of specific genes, produced by chemical synthesis or recombinant DNA techniques, that mediate RNAi. As used herein, the term isolated RNA includes RNA obtained by any means, including processing or cleavage of dsRNA; production by chemical synthetic methods; and production by recombinant DNA techniques. The invention further relates to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

The present invention also relates to a method of mediating RNA interference of genes of a patient. In one embodiment, RNA of about 21 to about 25 nt which targets the specific mRNA to be degraded is introduced into a patient's cells. The cells are maintained under conditions allowing degradation of the mRNA, resulting in RNA-mediated interference of the mRNA of the gene in the cells of the patient. Treatment of patients with cancer with the RNAi will inhibit the growth and spread of the cancer and reduce the tumor. Treatment of patients using RNAi can also be in combination with other anti-cancer compounds. The RNAi may be used in combination with other treatment modalities, such as chemotherapy, cryotherapy, hyperthermia, radiation therapy, and other similar treatments. In one embodiment, a chemotherapy agent was combined with the RNAi. In another embodiment, a chemotherapy named Gemzar was used.

Treatment of cancer or tumors in patients requires introduction of the RNA into the cancer or tumor cells. RNA may be directly introduced into the cell, or introduced extracellularly into a cavity, interstitial space, into the circulation of a patient, or introduced orally. Methods for oral introduction include direct mixing of the RNA with food, as well as engineered approaches in which a species that is used as food is engineered to express the RNA and then ingested. Physical methods of introducing nucleic acids, for example, injection directly into the cell or extracellular injection into the patient, may also be used. Vascular or extravascular circulation, the blood or lymph system, and the cerebrospinal fluid are sites where the RNA may be introduced. RNA may be introduced into an embryonic stem cell, or another multipotent cell derived from the patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into the cell, with the construct expressing RNA. Other methods known in the art for introducing nucleic acids to cells may be used, such as lipid-mediated carrier transport, chemical-mediated transport, and the like. Thus the RNA may be introduced along with components that perform one or more of the following activities: enhance RNA uptake by the cell, promote annealing of the duplex strands, stabilize the annealed strands, or otherwise increase inhibition of the target gene. The RNAi may be used in combination with other treatment modalities, such as chemotherapy, cryotherapy, hyperthermia, radiation therapy, and the like.

The present invention may be used alone or as a component of a kit having at least one of the reagents necessary to carry out the in vitro or in vivo introduction of RNA to tissue or patients. Preferred components are the dsRNA and a vehicle that promotes introduction of the dsRNA. Such a kit may also include instructions to allow a user of the kit to practice the invention.

Alternatively, a class of antisense molecules can be used to inactivate mRNA in order to decrease expression of Maba nucleic acid. Accordingly, these molecules can treat a disorder characterized by abnormal or undesired Maba nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Maba protein, such as substrate binding.

The nucleic acid molecules can be used for gene therapy in patients containing cells that are aberrant in Maba gene expression. Thus, recombinant cells, which include the patient's cells that have been engineered ex vivo and returned to the patient, are introduced into an individual where the cells produce the desired Maba protein to treat the individual.

8. Diagnosis using Maba Protein

Protein Detections

The present invention provides methods for diagnosing or detecting the differential presence of Maba protein. Where Maba is overexpressed in diseased cells, Maba protein is detected directly.

The information obtained is also used to determine prognosis and appropriate course of treatment. For example, it is contemplated that individuals with a specific Maba expression or stage of disease may respond differently to a given treatment that individuals lacking Maba expression. The information obtained from the diagnostic methods of the present invention thus provides for the personalization of diagnosis and treatment.

In one embodiment, the present invention provides a method for monitoring disease treatment in a subject comprising: determining the level of Maba protein or any fragment(s) or peptide(s) thereof in a test sample from said subject, wherein a level of said Maba protein similar to the level of said protein in a test sample from a healthy subject, or the level established for a healthy subject, is indicative of successful treatment.

In another embodiment, the present invention provides a method for diagnosing recurrence of disease following successful treatment in a subject comprising: determining the level of Maba protein or any fragment(s) or peptide(s) thereof in a test sample from said subject; wherein a changed level of said Maba protein relative to the level of said protein in a test sample from a healthy subject, or the level established for a healthy subject, is indicative of recurrence of diseases.

In yet another embodiment, the present invention provides a method for diagnosing or detecting disease in a subject comprising: determining the level of Maba protein or any fragment or peptides thereof in a test sample from said subject; wherein a differential level of said Maba protein relative to the level of said protein in a test sample from a healthy subject, or the level established for a healthy subject, is indicative of disease.

These methods are also useful for diagnosing diseases that show differential protein expression. As describe earlier, normal, control or standard values or level established from a healthy subject for protein expression are established by combining body fluids or tissue, cell extracts taken from a normal healthy mammalian or human subject with specific antibodies to a protein under conditions for complex formation. Standard values for complex formation in normal and diseased tissues are established by various methods, often photometric means. Then complex formation as it is expressed in a subject sample is compared with the standard values. Deviation from the normal standard and toward the diseased standard provides parameters for disease diagnosis or prognosis while deviation away from the diseased and toward the normal standard may be used to evaluate treatment efficacy.

In yet another embodiment, the present invention provides a detection or diagnostic method of Maba by using LC/MS.

The proteins from cells are prepared by methods known in the art (for example, R. Aebersold Nature Biotechnology, Volume 21, Number 6, June 2003). The differential expression of proteins in disease and healthy samples are quantitated using Mass Spectrometry and ICAT (Isotope Coded Affinity Tag) labeling, which is known in the art. ICAT is an isotope label technique that allows for discrimination between two populations of proteins, such as a healthy and a disease sample. The LC/MS spectra are collected for the labeled samples. The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios are calculated for each peptide of each replicate of the experiment. Thus overexpression or under expression of Maba protein or peptide are similar to the expression pattern in a test subject indicates the likelihood of having a disease, particularly cancer, or an associated pathology.

Immunological methods for detecting and measuring complex formation as a measure of protein expression using either specific polyclonal or monoclonal antibodies are known in the art. Examples of such techniques include enzyme-linked immunosorbent assays (ELISAs), radioimmunoassays (RIAs), fluorescence-activated cell sorting (FACS) and antibody arrays. Such immunoassays typically involve the measurement of complex formation between the protein and its specific antibody. These assays and their quantitation against purified, labeled standards are well known in the art (Ausubel, supra, unit 10.1-10.6). A two-site, monoclonal-based immunoassay utilizing antibodies reactive to two non-interfering epitopes is preferred, but a competitive binding assay may be employed (Pound (1998) Immunochemical Protocols, Humana Press, Totowa N.J.). More immunological detections are described in section below.

For diagnostic applications, the antibody or its variant typically will be labeled with a detectable moiety. Numerous labels are available which can be generally grouped into the following categories:

(a) Radioisotopes, such as $^{36}S$, $^{14}C$, $^{125}I$, $^{3}H$, and $^{131}I$. The antibody variant can be labeled with the radioisotope using the techniques described in Current Protocols in Immunology, vol 1-2, Coligen et al., Ed., Wiley-Interscience, New York, Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody variant using the techniques disclosed in Current Protocols in Immunology, supra, for example. Fluorescence can be quantified using a fluorometer.

(c) Various enzyme-substrate labels are available and U.S. Pat. Nos. 4,275,149 and 4,318,980 provide a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate.

Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

The biological samples can then be tested directly for the presence of Maba by assays (e.g., ELISA or radioimmunoassay) and format (e.g., microwells, dipstick, etc., as described in International Patent Publication WO 93/03367). Alternatively, proteins in the sample can be size separated (e.g., by polyacrylamide gel electrophoresis (PAGE)), in the presence or absence of sodium dodecyl sulfate (SDS), and the presence of Maba detected by immunoblotting (e.g., Western blotting). Immunoblotting techniques are generally more effective with antibodies generated against a peptide corresponding to an epitope of a protein, and hence, are particularly suited to the present invention.

Antibody binding may be detected also by "sandwich" immunoassays, immunoradiometric assays, gel diffusion precipitation reactions, immunodiffusion assays, in situ immunoassays (e.g., using colloidal gold, enzyme or radio-isotope labels, for example), precipitation reactions, agglutination assays (e.g., gel agglutination assays, hemagglutination assays, etc.), complement fixation assays, immunofluorescence assays, protein A assays, and immuno-electrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide is conjugated to KLH, it may be conjugated to BSA, or used directly, in a screening assay. In some embodiments, an automated detection assay is utilized. Methods for the automation of immunoassays are well known in the art (See e.g., U.S. Pat. Nos. 5,885,530, 4,981,785, 6,159,750, and 5,358,691, each of which is herein incorporated by reference). In some embodiments, the analysis and presentation of results is also automated. For example, in some embodiments, software that generates a prognosis based on the presence or absence of a series of antigens is utilized.

Competitive binding assays rely on the ability of a labeled standard to compete with the test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample, which remain unbound.

Sandwich assays involve the use of two antibodies, each capable of binding to a different immunogenic portion, or epitope, or the protein to be detected. In a sandwich assay, the test sample to be analyzed is bound by a first antibody, which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) that the tumor can be localized using immunoscintiography. In one embodiment, antibodies or fragments thereof bind to the extracellular domains of two or more Maba targets and the affinity value(Kd) is less than $1\times10^8$ M.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art.

For immunohistochemistry, the disease tissue sample may be fresh or frozen or may be embedded in paraffin and fixed with a preservative such as formalin (see Example). The fixed or embedded section contains the sample are contacted with a labeled primary antibody and secondary antibody, wherein the antibody is used to detect Maba protein expression in situ. The detailed procedure is shown in the Example.

Antibodies against Maba protein or peptides are useful to detect the presence of one of the proteins of the present invention in cells or tissues to determine the pattern of expression of the protein among various tissues in an organism and over the course of normal development.

Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy. More detection and diagnostic methods are described in detail below.

Additionally, antibodies are useful in pharmacogenomic analysis. Thus, antibodies prepared against polymorphic proteins can be used to identify individuals that require modified treatment modalities. The antibodies are also useful as diagnostic tools, as an immunological marker for aberrant protein analyzed by electrophoretic mobility, isoelectric point, tryptic peptide digest, and other physical assays known to those in the art.

The antibodies are also useful for tissue typing. Where a specific protein has been correlated with expression in a specific tissue, antibodies that are specific for this protein can be used to identify a tissue type.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

9. Methods of Treatment Based on Maba Protein a. Antibody Therapy

The antibody of the present invention can be used for therapeutic reasons. It is contemplated that the antibody of the present invention may be used to treat a mammal, preferably a human with a disease.

In general, the antibodies are also useful for inhibiting protein function, for example, blocking the binding of Maba protein or peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated within a cell or cell membrane. The functional blocking assays are provided in detail in the Examples.

The antibodies of present invention can also be used as means of enhancing the immune response. The antibodies can be administered in amounts similar to those used for other therapeutic administrations of antibody. For example, pooled gamma globulin is administered at a range of about 1 mg to about 100 mg per patient.

Antibodies reactive with the protein or peptides of Maba can be administered alone or in conjunction with other therapies, such as anti-cancer therapies, to a mammal afflicted with cancer or other disease. Examples of anti-cancer therapies include, but are not limited to, chemotherapy, radiation therapy, and adoptive immunotherapy therapy with TIL (Tumor Infiltration Lymphocytes).

The selection of an antibody subclass for therapy will depend upon the nature of the antigen to be acted upon. For example, an IgM may be preferred in situations where the antigen is highly specific for the diseased target and rarely occurs on normal cells. However, where the disease-associated antigen is also expressed in normal tissues, although at much lower levels, the IgG subclass may be preferred, since the binding of at least two IgG molecules in close proximity is required to activate complement, less complement mediated damage may occur in the normal tissues which express smaller amounts of the antigen and, therefore, bind fewer IgG antibody molecules. Furthermore, IgG molecules by being smaller may be more able than IgM molecules to localize to the diseased tissue.

The mechanism for antibody therapy is that the therapeutic antibody recognizes a cell surface protein or a cytosolic protein that is expressed or preferably, overexpressed in a diseased cell. By NK cell or complement activation, or conjugation of the antibody with an immunotoxin or radiolabel, the interaction can abrogate ligand/receptor interaction or activation of apoptosis.

The potential mechanisms of antibody-mediated cytotoxicity of diseased cells are phagocyte (antibody dependent cellular cytotoxicity (ADCC)) (see Example), complement (Complement-mediated cytotoxicity (CMC)) (see Example), naked antibody (receptor cross-linking apoptosis and growth factor inhibition), or targeted payload labeled with radionuclide or immunotoxins or immunochemotherapeutics.

In one embodiment, the antibody is administered to a non-human mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed on the mammal.

The antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the antibody variant is suitably administered by pulse infusion, particularly with declining doses of the antibody variant. Preferably the dosing is given by injections, most preferably intravenous or subcutaneous injections, depending in part on whether the administration is brief or chronic.

For the prevention or treatment of a disease, the appropriate dosage of the antibody will depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of the disease, about 1 µg/kg to 150 mg/kg (e.g., 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutically effective amount of the antibody to be administered will be governed by such considerations, and is the minimum amount necessary to prevent, ameliorate, or treat a disease or disorder. The antibody may optionally be formulated with one or more agents currently used to prevent or treat the disorder in question.

Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$ $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein A therapeutic agent may be coupled (e.g., covalently bonded) to a suitable antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be affected, for example, through amino groups, carboxyl groups, sulfhydryl groups or oxidized carbohydrate residues. There are numerous references describing such methodology, e.g. U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671, 958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways as described above.

b. Other Immunotherapy

Peptides derived from the Maba protein sequence may be modified to increase their immunogenicity by enhancing the binding of the peptide to the MHC molecules in which the peptide is presented. The peptide or modified peptide may be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites, D. P. and Ten A. I. (eds) Appleton and Lange, Norwalk Conn., San Mateo, Calif.).

An "immunogenic peptide" is a peptide, which comprises an allele-specific motif such that the peptide will bind the MHC allele (HLA in human) and be capable of inducing a CTL (cytotoxic T-lymphocytes) response. Thus, immunogenic peptides are capable of binding to an appropriate class I or II MHC molecule and inducing a cytotoxic T cell or T helper cell response against the antigen from which the immunogenic peptide is derived.

Alternatively, amino acid sequence variants of the peptide can be prepared by altering the nucleic acid sequence of the DNA which encodes the peptide, or by peptide synthesis. At the genetic level, these variants ordinarily are prepared by site-directed mutagenesis of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

The recombinant or natural protein, peptides, or fragment thereof of Maba, or modified peptides, may be used as a vaccine either prophylactically or therapeutically. When provided prophylactically the vaccine is provided in advance of any evidence of disease, particularly, cancer. The prophylactic administration of the disease vaccine should serve to prevent or attenuate diseases, preferably cancer, in a mammal.

Preparation of vaccine uses recombinant protein or peptide expression vectors comprising a nucleic acid sequence encoding all or part of the Maba protein. Examples of vectors that may be used in the aforementioned vaccines include, but are not limited to, defective retroviral vectors, adenoviral vectors vaccinia viral vectors, fowl pox viral vectors, or other viral vectors (Mulligan, R. C., (1993) Science 260:926-932). The vectors can be introduced into a mammal either prior to any evidence of the disease or to mediate regression of the disease in a mammal afflicted with disease. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the vector may be administered locally by direct injection into the cancer lesion or topical application in a pharmaceutically acceptable carrier. The quantity of viral vector, carrying all or part of the Maba nucleic acid sequence, to be administered is based on the titer of virus particles. A preferred range may be about $10^6$ to about $10^{11}$ virus particles per mammal, preferably a human.

After immunization the efficacy of the vaccine can be assessed by the production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with cancer, the vaccine can be administered in conjunction with other therapeutic treatments. Examples of other therapeutic treatments includes, but are not limited to, adoptive T cell immunotherapy, coadministration of cytokines or other therapeutic drugs for cancer.

Alternatively all or parts thereof of a substantially or partially purified the Maba protein or their peptides may be administered as a vaccine in a pharmaceutically acceptable carrier. Ranges of the protein that may be administered are about 0.001 to about 100 mg per patient, preferred doses are about 0.01 to about 100 mg per patient. Immunization may be repeated as necessary, until a sufficient titer of anti-immunogen antibody or immune cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573), dendritic cells. The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. 3rd. ed., Cold Spring Harbor Laboratory Press, Cold Spring Harbor, N.Y., (2001).

The vaccine formulation of the present invention comprises an immunogen that induces an immune response directed against the cancer associated antigen such as Maba protein, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the vaccine.

In one embodiment mammals, preferably human, at high risk for disease, particularly cancer, are prophylactically treated with the vaccines of this invention. Examples include, but are not limited to, humans with a family history of a disease, humans with a history of disease, particular cancer, or humans afflicted with a disease, such as cancer that has been previously resected and therefore at risk for reoccurrence. When provided therapeutically, the vaccine is provided to enhance the patient's own immune response to the disease antigen present on the disease cells or present during advanced stage of the disease. The vaccine, which acts as an immunogen, may be a cell, cell lysate from cells transfected with a recombinant expression vector, or a culture supernatant containing the expressed protein. Alternatively, the immunogen is a partially or substantially purified recombinant protein, peptide or analog thereof or modified peptides or analogs thereof. The proteins or peptides may be conjugated with lipoprotein or administered in liposomal form or with adjuvant.

While it is possible for the immunogen to be administered in a pure or substantially pure form, it is preferable to present it as a pharmaceutical composition, formulation or preparation, as discussed hereinabove.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route appropriate for antibody production such as intravenous, intraperitoneal, intramuscular, subcutaneous, and the like. The immunogen may be administered once or at periodic intervals until a significant titer of anti-Maba immune cells or anti-Maba antibody is produced. The presence of anti-Maba immune cells may be assessed by measuring the frequency of precursor CTL (cytotoxic T-lymphocytes) against Maba antigen prior to and after immunization by a CTL precursor analysis assay (Coulie, P. et al., (1992) International Journal Of Cancer 50:289-297). The antibody may be detected in the serum using the immunoassay described above.

The safety of the immunization procedures is determined by examining the effect of immunization on the general health of the immunized animal (fever, change in weight, appetite, behavior etc.) and pathological changes on autopsies. After initial testing in animals, human patients can be tested. Conventional methods would be used to evaluate the immune response of the patient to determine the efficiency of the vaccine.

In yet another embodiment of this invention all, part, or parts of the Maba protein or peptides or fragments thereof, or modified peptides, may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The Maba antigen activated dendritic cells or processed dendritic cell antigens may be used as immunogens for vaccines or for the treatment of diseases, particularly cancer. The dendritic cells should be exposed to the antigen for sufficient time to allow the antigens to be internalized and presented on the dendritic cells surface. The resulting dendritic cells or the dendritic-cell processed antigens can then be administered to an individual in need of therapy. Such methods are described in Steinman et al. (WO93/208185) and in Banchereau et al. (EPO Application 0563485A1).

In yet another aspect of this invention T-cells isolated from individuals can be exposed to Maba protein, peptides or fragment thereof, or modified peptides in vitro and then administered to a patient in need of such treatment in a therapeutically effective amount. Examples of where T-lymphocytes can be isolated include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) J.

Immunol. 142: 2453-3461). Lymphocytes are cultured in media such as RPMI or RPMI 1640 or AIM V for 1-10 weeks. Viability is assessed by trypan blue dye exclusion assay. Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

The present invention is further described by the following examples, which are provided solely to illustrate the invention by reference to specific embodiments. This exemplification, while illustrating certain aspects of the invention, does not offer the limitations or circumscribe the scope of the disclosed invention.

10. Screening Methods Using Proteins

The Maba protein and polypeptide can be used to identify compounds or agents that modulate Maba activity of the protein in its natural state or an altered form that causes a specific disease or pathology associated with Maba. Both Maba of the present invention and appropriate variants and fragments can be used in high-throughput screens to assay candidate compounds for the ability to bind to Maba. These compounds can be further screened against functional Maba to determine the effect of the compound on Maba activity. Further, these compounds can be tested in animal or invertebrate systems to determine activity/effectiveness. Compounds can be identified that activate (agonist) or inactivate (antagonist) Maba to a desired degree.

Both Maba of the present invention and appropriate variants and fragments can be used in high-throughput screening to assay candidate compounds for the ability to bind to Maba. These compounds can be further screened against functional Maba to determine the effect of the compound on Maba activity. Further, these compounds can be tested in animal or invertebrate systems to determine activity/effectiveness. Compounds can be identified that activate (agonist) or inactivate (antagonist) Maba to a desired degree.

Further, the proteins of the present invention can be used to screen a compound or an agent for the ability to stimulate or inhibit interaction between Maba protein and a molecule that normally interacts with Maba protein, e.g. a substrate or an extracellular binding ligand or a component of the signal pathway that Maba protein normally interacts (for example, a cytosolic signal protein). Such assays typically include the steps of combining Maba protein with a candidate compound under conditions that allow Maba protein, or fragment, to interact with the target molecule, and to detect the formation of a complex between the protein and the target or to detect the biochemical consequence of the interaction with Maba protein and the target, such as any of the associated effects of signal transduction such as protein phosphorylation, cAMP turnover, and adenylate cyclase activation, etc.

Candidate compounds or agents include 1) peptides such as soluble peptides, including Ig-tailed fusion peptides and members of random peptide libraries (see, e.g., Lam et al., Nature 354:82-84 (1991); Houghten et al., Nature 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767-778 (1993)); 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries).

One candidate compound or agent is a soluble fragment of Maba that competes for substrate binding. Other candidate compounds include mutant Maba or appropriate fragments containing mutations that affect Maba function and thus compete for substrate. Accordingly, a fragment that competes for substrate, for example with a higher affinity, or a fragment that binds substrate but does not allow release, is encompassed by the invention.

Any of the biological or biochemical functions mediated by Maba can be used as an endpoint assay to identify an agent that modulates Maba activity. These include all of the biochemical or biochemical/biological events described herein, in the references cited herein, incorporated by reference for these endpoint assay targets, and other functions known to those of ordinary skill in the art or that can be readily identified. Specifically, a biological function of a cell or tissues that expresses Maba can be assayed.

A substrate-binding region can be used that interacts with a different substrate than one which is recognized by the native Maba. Accordingly, a different set of signal transduction components is available as an end-point assay for activation. This allows for assays to be performed in other than the specific host cell from which Maba is derived.

Competition binding assays may also be used to discover compounds that interact with Maba (e.g. binding partners and/or ligands). Thus, a compound is exposed to Maba polypeptide under conditions that allow the compound to bind or to otherwise interact with the polypeptide. Soluble Maba polypeptide is also added to the mixture. If the test compound interacts with the soluble Maba polypeptide, it decreases the amount of complex formed or activity from Maba. This type of assay is particularly useful in cases in which compounds are sought that interact with specific regions of Maba. Thus, the soluble polypeptide that competes with the target Maba region is designed to contain peptide sequences corresponding to the region of interest.

To perform cell free drug screening assays, it is sometimes desirable to immobilize either the Maba protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Maba-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of Maba-binding protein and a candidate compound are incubated in Maba protein-presenting wells and the amount of complex trapped in the well can be quantitated. Methods for detecting such complexes, in addition to those described above for the GST-immobilized complexes, include immunodetection of complexes using antibodies reactive with the Maba protein target molecule, or which are reactive with Maba protein and compete with the target molecule, as well as Maba-linked assays which rely on detecting an enzymatic activity associated with the target molecule.

Agents that modulate Maba of the present invention can be identified using one or more of the above assays, alone or in combination. It is generally preferable to use a cell-based or cell free system first and then confirm activity in an animal or other model system. Such model systems are well known in the art and can readily be employed in this context.

In yet another aspect of the invention, Maba protein can be used as a "bait protein" in a two-hybrid assay or three-hybrid assay (see, e.g., U.S. Pat. No. 5,283,317; Zervos et al. (1993) Cell 72:223-232; Madura et al. (1993) J. Biol. Chem. 268: 12046-12054; Bartel et al. (1993) Biotechniques 14:920-924; Iwabuchi et al. (1993) Oncogene 8:1693-1696; and Brent WO94/10300), to identify other proteins, which bind to or interact with Maba and are involved in Maba activity. Such Maba-binding proteins are also likely to be involved in the propagation of signals by Maba protein or Maba targets as, for example, downstream elements of a Maba-mediated signaling pathway. Alternatively, such Maba-binding proteins are likely to be Maba inhibitors.

The two-hybrid system is based on the modular nature of most transcription factors, which consist of separable DNA-binding and activation domains. Briefly, the assay utilizes two different DNA constructs. In one construct, the gene that codes for Maba protein is fused to a gene encoding the DNA binding domain of a known transcription factor (e.g., GAL-4). In the other construct, a DNA sequence, from a library of DNA sequences that encode an unidentified protein ("prey" or "sample") is fused to a gene that codes for the activation domain of the known transcription factor. If the "bait" and the "prey" proteins are able to interact, in vivo, forming a Maba-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with Maba protein.

Array:

"Array" refers to an ordered arrangement of at least two transcripts, proteins or peptides, or antibodies on a substrate. At least one of the transcripts, proteins, or antibodies represents a control or standard, and the other transcript, protein, or antibody is of diagnostic or therapeutic interest. The arrangement of at least two and up to about 40,000 transcripts, proteins, or antibodies on the substrate assures that the size and signal intensity of each labeled complex, formed between each transcript and at least one nucleic acid, each protein and at least one ligand or antibody, or each antibody and at least one protein to which the antibody specifically binds, is individually distinguishable.

An "expression profile" is a representation of gene expression in a sample. A nucleic acid expression profile is produced using sequencing, hybridization, or amplification technologies using transcripts from a sample. A protein expression profile, although time delayed, minors the nucleic acid expression profile and is produced using gel electrophoresis, mass spectrometry, or an array and labeling moieties or antibodies which specifically bind the protein. The nucleic acids, proteins, or antibodies specifically binding the protein may be used in solution or attached to a substrate, and their detection is based on methods well known in the art.

A substrate includes but is not limited to, paper, nylon or other type of membrane, filter, chip, glass slide, or any other suitable solid support.

The present invention also provides an antibody array. Antibody arrays have allowed the development of techniques for high-throughput screening of recombinant antibodies. Such methods use robots to pick and grid bacteria containing antibody genes, and a filter-based ELISA to screen and identify clones that express antibody fragments. Because liquid handling is eliminated and the clones are arrayed from master stocks, the same antibodies can be spotted multiple times and screened against multiple antigens simultaneously. For more information, see de Wildt et al. (2000) Nat. Biotechnol. 18:989-94.

The array is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), U.S. Pat. No. 5,807, 522, Brown et al., all of which are incorporated herein in their entirety by reference.

In one embodiment, a nucleic acid array or a microarray, preferably composed of a large number of unique, single-stranded nucleic acid sequences, usually either synthetic antisense oligonucleotides or fragments of cDNAs, fixed to a solid support. The oligonucleotides are preferably about 6-60 nucleotides in length, more preferably 15-30 nucleotides in length, and most preferably about 20-25 nucleotides in length.

In order to produce oligonucleotides to a known sequence for an array, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on an array. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process, wherein the substrate may be paper, nylon or other type of membrane, filter, chip, glass slide or any other suitable solid support as described above.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference.

A gene expression profile comprises the expression of a plurality of transcripts as measured by after hybridization with a sample. The transcripts of the invention may be used as elements on an array to produce a gene expression profile. In one embodiment, the array is used to diagnose or monitor the progression of disease. Researchers can assess and catalog the differences in gene expression between healthy and diseased tissues or cells.

For example, the transcript or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human or nonmammal, with a transcript under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

By analyzing changes in patterns of gene expression, disease can be diagnosed at earlier stages before the patient is symptomatic. The invention can be used to formulate a prognosis and to design a treatment regimen. The invention can also be used to monitor the efficacy of treatment. For treatments with known side effects, the array is employed to improve the treatment regimen. A dosage is established that causes a change in genetic expression patterns indicative of successful treatment. Expression patterns associated with the onset of undesirable side effects are avoided.

In another embodiment, animal models which mimic a human disease can be used to characterize expression profiles associated with a particular condition, disease, or disorder; or treatment of the condition, disease, or disorder. Novel treatment regimens may be tested in these animal models using arrays to establish and then follow expression profiles over time. In addition, arrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

WORKING EXAMPLES

1. Breast Tissues and Cell Lines

Breast Tissues
Tissue Processing

All tissues were procured as fresh specimens. Tissues were collected as remnant tissues following surgical resection of cancer tissues. Remnant tissues were supplied following processing for pathological diagnosis according to proper standards of patient care. Procurement of all tissues was performed in an anonymised manner in strict compliance with Federal mandated ethical and legal guidelines (HIPAA) and in accordance with clinical institution ethical review board as well as the internal institutional review board. Tissues were transported on ice in ice-cold transport buffer by courier for processing.

i) Enrichment of Epithelial Cells from Normal Breast Tissue:

Normal breast tissue was transferred from the transport vessel to a sterile dish containing 25 ml of ice-cold transport buffer. The tissue was measured, weighed and photographed. The tissue was dissected to isolate breast tissue which was transferred to a fresh dish containing 25 ml ice-cold Hanks buffered saline solution. The tissue section was washed by vigorous shaking and the HBSS replaced. This was repeated two further times or until all visible mucus was removed. Mucosa was measured, weighed and diced into 1 mm2 sections. The tissues sections were transferred to a 50 ml polypropylene centrifuge tube containing 50 ml of A52 media (Biosource) supplemented with 2 mM L-glutamine and 1.5 mg/ml dispase (Roche Biochemicals). The digest was incubated for 1 h at 37° C. with frequent agitation. Following the incubation, the suspension was poured through a 40-mesh cell sieve situated in the base of a 15 cm culture dish. The filtrate was diluted to 50 ml using A52 media supplemented with 2 mM L-glutamine and passed through a 200-mesh cell sieve. The filtrate was collected into a 50 ml polypropylene centrifuge tube and the suspension was triturated several times followed by vortexing for 2 min at setting 6. The density and viability of nucleated cells was determined by flow cytometry using propidium iodide as a negative stain for viability (Guava system). Erythrocytes were lysed using a standard ammonium chloride lysis protocol with incubation at room temperature for 10s. Cells were harvested by centrifugation at 500 g for 5 min at 4° C. The cell pellet was resuspended in 50 ml of ice-cold HBSS and recentrifuged. The final cell pellet was resuspended in 3 ml of ice-cold HBSS supplemented with 0.1% BSA and 0.25M EDTA. Cell density and viability were estimated using the Guava system and the density adjusted to $1 \times 10^7$ cells per ml. Epithelial cells were stained with a FITC-labeled anti-EpCAM murine monoclonal antibody and enriched by cell sorting using flow cytometry.

ii) Enrichment of Tumor Cells from Cancer Tissue

Cancer tissue was transferred from the transport vessel to a sterile dish containing 25 ml of ice-cold transport buffer. The tissue was measured, weighed and photographed. The tissue was dissected to remove necrotic and fibrotic tissue plaques and the tumour tissue transferred to a fresh dish containing 25 ml ice-cold Hanks buffered saline solution. The tissue section was washed by vigorous shaking and the HBSS replaced. This was repeated 2 further times or until all visible mucus was removed. Tumor tissue was measured, weighed and extensively diced. The tissues slurry was transferred to a 50 ml polypropylene centrifuge tube containing 50 ml of A52 media (Biosource) supplemented with 2 mM L-glutamine and 1.5 mg/ml dispase (Roche Biochemicals). The digest was incubated for 1 h at 37° C. with frequent agitation. Following the incubation, the suspension was poured through a 40-mesh cell sieve situated in the base of a 15 cm culture dish. The filtrate was diluted to 50 ml using A52 media supplemented with 2 mM L-glutamine and passed through a 200-mesh cell sieve. The filtrate was collected into a 50 ml polypropylene centrifuge tube and the suspension was triturated several times followed by vortexing for 2 min at setting 6. The density and viability of nucleated cells was determined by flow cytometry using propidium iodide as a negative stain for viability (Guava system). Erythrocytes were lysed using a standard ammonium chloride lysis protocol with incubation at room temperature for 10s. Cells were harvested by centrifugation at 500 g for 5 min at 4° C. The cell pellet was resuspended in 50 ml of ice-cold HBSS and recentrifuged. The final cell pellet was resuspended in 3 ml of ice-cold HBSS supplemented with 0.1% BSA and 0.25M EDTA. Cell density and viability were estimated using the Guava system and the density adjusted to $1 \times 10^7$ cells per ml. Epithelial cells were stained with a FITC-labeled anti-EpCAM murine monoclonal antibody and enriched by cell sorting using flow cytometry.

iii) Enrichment of Cell Surface Proteins from Sorted Epithelial and Tumor Cells

Sorted cells were centrifuged at 500 g at 4° C. for 5 min and resuspended in 50 ml of ice-cold DPBS. The cell suspension was washed by 2 further cycles of centrifugation 500 g at 4° C. for 5 min and resuspension of the cell pellet in 50 ml of ice-cold DPBS. Finally, the cell pellet was resuspended in 9.5 ml of ice-cold DPBS and sodium metaperiodate added to a final concentration of 1 mM. The cell suspension was incubated on ice for 10 min with frequent agitation in the dark. Cells were centrifuged at 500 g at 4° C. for 5 min and resuspended in 50 ml of ice-cold DPBS. The cell suspension was washed by 2 further cycles of centrifugation 500 g at 4° C. for 5 min and resuspension of the cell pellet in 50 ml of ice-cold DPBS. Finally, the cell pellet was resuspended in lysis buffer (1% SDS [w/v]; 0.1M HEPES; 10 mM $MgCl_2$; 0.1% Non ionic detergent P40; 100 ml protease inhibitor cocktail [P8340, Sigma]) and homogenisation performed by passage of lysate through a 18G syringe needle 10 times. Protein concentrations were assayed relative to a Bovine serum albumin standard by a modified Lowry assay (DC assay, Bio-RAD) and 1 mg of total cellular protein transferred to a fresh tube and diluted to 1 mg/ml in acetate buffer (0.1M, pH 5.0).

Cancer Cell Line Model System:

The model system employed here involves the use of a "normal" reference (i.e., control) to which cell surface expression in tumor-derived cell lines is compared. These differentials or candidates are then validated in tissues, cancer and normal breast tissue, to confirm that they are differentially expressed between these tissues as well as within the cell line model system.

Cancer Cell Line Culture

Cell lines were grown in a culturing medium that is supplemented as necessary with growth factors and serum, in accordance with the American Type Culture Collection (ATCC) (Mannassas, Va.) guidelines for each particular cell line. Cultures were established from frozen stocks in which the cells were suspended in a freezing medium (cell culture medium with 10% DMSO [v/v]) and flash frozen in liquid nitrogen. Frozen stocks prepared in this way were stored in the liquid nitrogen vapour. Cell cultures were established by rapidly thawing frozen stocks at 37° C. Thawed stock cultures were slowly transferred to a culture vessel containing a large volume of culture medium that was supplemented. For maintenance of culture, cells were seeded at $1 \times 10^5$ cells/per ml in medium and incubated at 37° C. until confluence of cells in the culture vessel exceeds 50% by area. At this time, cells were harvested from the culture vessel using enzymes or EDTA where necessary. The density of harvested, viable cells was estimated by hemocytometry and the culture reseeded as above. A passage of this nature was repeated no more than 25 times at which point the culture was destroyed and reestablished from frozen stocks as described above.

For the analyses of cell surface protein expression in cultured cell lines, cells were grown as described above. At a period 24 h prior to the experiment, the cell line was passaged as described above. This yielded cell densities that were <50% confluent and growing exponentially. Typically, triplicate analyses of differential expression were performed for each line relative to Caco2 for the purpose of identifying statistically significant reproducible differentially expressed proteins.

2. Cloning and Expression of Target Proteins cDNA Retrieval

Peptide sequences were searched by BlastP against the CELERA DISCOVERY SYSTEM (CDS) and public database to identify the corresponding full-length open reading frames (ORFs). Each ORF sequence was then searched by BlastN against the Celera in-house human cDNA clone collection. For each sequence of interest, up to three clones are pulled and streaked onto LB/Ampicillin (100 ug/ml) plates. Plasmid DNA is isolated using Qiagen spin mini-prep kit and verified by restriction digest. Subsequently, the isolated plasmid DNA is sequence verified against the ORF reference sequence. Sequencing reactions are carried out using Applied Biosystems BIGDYE TERMINATOR kit followed by ethanol precipitation. Sequence data is collected using the Applied Biosystems 3100 GENETIC ANALYZER and analyzed by alignment to the reference sequence using the Clone Manager alignment tool.

PCR

PCR primers are designed to amplify the full-length ORF as well as any regions of the ORF that are interest for expression (antigenic or hydrophilic regions as determined by the CLONE MANAGER sequence analysis tool). Primers also contain 5' and 3' overhangs to facilitate cloning (see below). PCR reactions contain 2.5 units PLATINUM TAQ DNA POLYMERASE HIGH FIDELITY (Invitrogen), 50 ng cDNA plasmid template, 1 uM forward and reverse primers, 800 uM dNTP cocktail (Applied Biosystems) and 2 mM MgSO4. After 20-30 cycles (94° C. for 30 seconds, 55° C. for 1 minutes and 73° C. for 2 minutes), product is verified and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO or pEntr/SD/D-TOPO and are used as described in the cloning methods below.

TOPO Cloning into pEntr/D-TOPO or pEntr/SD/D-TOPO

For cloning using this method, the forward PCR primer contained a 5' overhang containing the sequence "CACC". PCR products are generated as described above and cloned into the entry vector using the Invitrogen TOPO cloning kit. Reactions are typically carried out at room temperature for 10 minutes and subsequently transformed into TOP10 chemically competent cells (Invitrogen, CA). Candidate clones are picked, plasmid DNA is prepared using Qiagen spin mini-prep kit and screened using restriction digest. Inserts are subsequently sequence verified as described above.

Gateway Cloning into pDonr201 or pDonr221

For cloning using this method, PCR primers contained the following overhangs:

Forward 5' overhang:

(SEQ ID NO: 15)
5'-GGGGACAAGTTTGTACAAAAAAGCAGGCTTC-3'

Reverse 5' overhang:

(SEQ ID NO: 16)
5'-GGGGACCACTTTGTACAAGAAAGCTGGGT-3'

PCR products are generated as described above. ORFs are recombined into the entry vector using the Invitrogen Gateway BP Clonase enzyme mix. Reactions are typically carried out at 25° C. for 1 hour, treated with Proteinase K at 37° C. for 10 minutes and transformed into Library Efficiency DH5α chemically competent cells (Invitrogen, CA). Candidate clones are picked, plasmid DNA is prepared using Qiagen spin mini-prep kit and screened using restriction digest. Inserts are subsequently sequence verified as described above.

Construction of Expression Clones

ORFs are transferred from the entry construct into a series of expression vectors using the Gateway LR Clonase enzyme mix. Reactions are typically carried out for 1 hour at 25° C., treated with Proteinase K at 37° C. for 10 minutes and subsequently transformed into Library Efficiency DH5a chemically competent cells (Invitrogen). Candidate clones are picked, plasmid DNA is prepared using Qiagen spin mini-prep kit and screened using restriction digest. Expression vectors include but are not limited to pDest14, pDest15, pDest17, pDest8, pDest10 and pDest20. These vectors allow expression in systems such as *E. coli* and recombinant baculovirus. Other vectors not listed here allow expression in yeast, mammalian cells, or in vitro.

Expression of Recombinant Proteins in *E. Coli*

Constructs are transformed into one or more of the following host strains: BL21 SI, BL21 AI, (Invitrogen); Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.3 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm, at 4° C. Cell pellets are stored at −80° C.

Expression of Recombinant Proteins Using Baculovirus

Recombinant proteins are expressed using baculovirus in Sf21 fall army worm ovarian cells. Recombinant baculoviruses are prepared using the BAC-TO-BAC SYSTEM (Invitrogen) per the manufacturer's instructions. Proteins are expressed on the large scale in Sf900 μl serum-free medium (Invitrogen) in a 10 L bioreactor tank (27° C., 130 rpm, 50% dissolved oxygen for 48 hours).

3. Recombinant Protein Purification

Recombinant proteins are purified from *E. coli* and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column, e.g. His-tagged proteins are separated using a pre-packed chelating SEPHAROSE column (Pharmacia) or GST-tagged proteins are separated using a glutathione SEPHAROSE column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size and shape.

Expression and purification of the protein are also achieved using either a mammalian cell expression system or an insect cell expression system. The pUB6/V5-His vector system (Invitrogen, CA) is used to express GSCC in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6.times.His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6xhis which enables purification as described above. Purified protein is used in the following activity and to make antibodies 4. Chemical Synthesis of Peptides Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20). Automated synthesis may also be carried out on machines such as the 431A peptide synthesizer (ABI). A protein or portion thereof may be purified by preparative high performance liquid chromatography and its composition confirmed by amino acid analysis or by sequencing (Creighton (1984) Proteins, Structures and Molecular Properties, W H Freeman, New York N.Y.).

5. Antibody Development

Polyclonal Antibody Preparations:

Polyclonal antibodies against recombinant proteins are raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21 and 49. Bleeds are collected and screened for recognition of the antigen by solid phase ELISA and western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against Maba from a Library of scFvs

Naturally occurring V-genes isolated from human PBLs are constructed into a library of antibody fragments which contain reactivities against Maba to which the donor may or may not have been exposed (see e.g., U.S. Pat. No. 5,885,793 incorporated herein by reference in its entirety).

Rescue of the Library: A library of scFvs is constructed from the RNA of human PBLs as described in PCT publication WO 92/01047. To rescue phage displaying antibody fragments, approximately $10^9$ E. coli harboring the phagemid are used to inoculate 50 ml of 2×TY containing 1% glucose and 100 .mu.g/ml of ampicillin (2.times.TY-AMP-GLU) and grown to an O.D. of 0.8 with shaking. Five ml of this culture is used to innoculate 50 ml of 2.times.TY-AMP-GLU, 2× $10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 .mu.g/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-CENTRA 8,400 r.p.m. for 10 min), resuspended in 300 ml 2×TY broth containing 100 .mu.g ampicillin/ml and 25 .mu.g kanamycin/ml (2×TY-AMP-KAN) and grown overnight, shaking at 37° C. Phagre particles are purified and concentrated from the culture medium by two PEG-precipitations (Sambrook et al., 2001), resuspended in 2 ml PBS and passed through a 0.45 .mu.m filter (Minisart NML; Sartorius) to give a final concentration of approximately 1013 transducing units/ml (ampicillin-resistant clones).

Panning of the Library: Immunotubes (Nunc) are coated overnight in PBS with 4 ml of either 100 .mu.g/ml or 10 .mu.g/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phages are then used to infect 10 ml of mid-log E. coli TG1 by incubating eluted phage with bacteria for 30 minutes at 37° C. The E. coli are then plated on TYE plates containing 1% glucose and 100 .mu.g/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders: Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 .mu.g/ml of the polypeptide of the present invention in 50 mM bicarbonate pH 9.6. Clones positive in ELISA are further characterized by PCR fingerprinting (see, e.g., PCT publication WO 92/01047) and then by sequencing.

Monoclonal Antibody Generation i) Materials:

1) Complete Media No Sera (CMNS) for washing of the myeloma and spleen cells; Hybridoma medium CM-HAT {Cell Mab (BD), 10% FBS (or HS); 5% Origen HCF (hybridoma cloning factor) containing 4 mM L-glutamine and antibiotics} to be used for plating hybridomas after the fusion.

2) Hybridoma medium CM-HT (NO AMINOPTERIN) (Cell Mab (BD), 10% FBS 5% Origen HCF containing 4 mM L-glutamine and antibiotics) to be used for fusion maintenance are stored in the refrigerator at 4-6° C. The fusions are fed on days 4, 8, and 12, and subsequent passages. Inactivated and pre-filtered commercial Fetal Bovine serum (FBS) or Horse Serum (HS) are thawed and stored in the refrigerator at 4° C. and must be pretested for myeloma growth from single cells.

3) The L-glntamine (200 mM, 100× solution), which is stored at −20° C. freezer, is thawed and warmed until completely in solution. The L-glntamin is dispensed into media to supplement growth. L-glntamin is added to 2 mM for myelomas, and 4 mM for hybridoma media. Further the Penicillin, Streptomycin, Amphotericin (antibacterial-antifungal stored at −20° C.) is thawed and added to Cell Mab Media to 1%.

4) Myeloma growth media is CELL MAB MEDIA (CELL MAB MEDIA, QUANTUM YIELD from BD is stored in the refrigerator at 4° C. in the dark) which are added L-glntamine to 2 mM and antibiotic/antimycotic solution to 1% and is called CMNS.

5) 1 bottle of PEG 1500 in Hepes (Roche, N.J.)

6) 8-Azaguanine is stored as the dried powder supplied by SIGMA at −700° C. until needed. Reconstitute 1 vial/500 ml of media and add entire contents to 500 ml media (eg. 2 vials/liter).

7) Myeloma Media is CM which has 10% FBS (or HS) and 8-Aza (1×) stored in the refrigerator at 4° C.

8) CLONAL CELL MEDIUM D (Stemcell, Vancouver) contains HAT and methyl cellulose for semi-solid direct cloning from the fusion. This comes in 90 ml bottles with a CoA and must be "melted at 37° C. in a waterbath in the morning of the day of the fusion. Loosen the cap and leave in CO2 incubator to sufficiently gas the medium D and bring the pH down.

9) Hybridoma supplements HT [hypoxanthine, thymidine] are to be used in medium for the section of hybridomas and maintenance of hybridomas through the cloning stages respectively.

10) Origen HCF can be obtained directly from Igen and is a cell supernatant produced from a macrophage-like cell-line. It can be thawed and aliqouted to 15 ml tubes at 5 ml per tube and stored frozen at −20° C. Positive Hybridomas are fed HCF through the first subcloning and are gradually weaned. It is not necessary to continue to supplement unless you have a particularly difficult hybridoma clone. This and other additives have been shown to be more effective in promoting new hybridoma growth than conventional feeder layers.

ii) Procedure

To generate monoclonal antibodies, mice are immunized with 5-50 ug of antigen either intra-peritoneally (i.p.) or by intravenous injection in the tail vein (i.v.). Typically, the antigen used is a recombinant protein that is generated as described above. The primary immunization takes place 2 months prior to the harvesting of splenocytes from the mouse and the immunization is typically boosted by i.v. injection of 5-50 ug of antigen every two weeks. At least one week prior to expected fusion date, a fresh vial of myeloma cells is thawed and cultured. Several flasks at different densities are maintained in order that a culture at the optimum density is ensured at the time of fusion. The optimum density is determined to be $3-6\times10^5$ cells/ml. Two to five days before the scheduled fusion, a final immunization is administered of ~5 ug of antigen in PBS i.p. or i.v.

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1\times10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96 well plate.

To prepare splenocytes from immunized mice, the animals are euthanised and submerged in 70% ETOH. Under sterile conditions, the spleen is surgically removed and placed in 10 ml of RPMI medium supplemented with 20% fetal calf serum in a Petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed 2 more times with 30 ml of RPMI-CMNS. Spin at 800 rpm for 12 minutes.

Supernatant is removed and cells are resuspended in 5 ml of RPMI-CMNS and are pooled to fill volume to 30 ml and spin down as before. Then, the pellet is broken up by gently tapping on the flow hood surface and resuspended in 1 ml of BMB REG1500 (prewarmed to 37° C.) dropwise with 1 cc needle over 1 minute.

RPMI-CMNS to the PEG cells and RPMI-CMNS are added to slowly dilute out the PEG. Cells are centrifuged and diluted in 5 ml of Complete media and 95 ml of CLONA-CELL MEDIUM D (HAT) media (with 5 ml of HCF). The cells are plated out 10 ml per small petri plate.

Myeloma/HAT control. P is prepared as follows: dilute about 1000 P3X63 Ag8.653 myeloma cells into 1 ml of mediu D and transfer into a single well of a 24 well plate. Plates are placed in incubator, with two plates inside of a large petri plate, with an additional petri plate full of distilled water, for 10-18 days under 5% CO2 overlay at 37° C. Clones are picked from semisolid agarose into 96 well plates containing 150-200 ul of CM-HT. Supernatants are screened 4 days later in ELISA, and positive clones are moved up to 24 well plates. Heavy growth will require changing of the media at day 8 (+/−150 ml). One should further decrease the HCF to 0.5% (gradually—2%, then 1%, then 0.5%) in the cloning plates.

For further references see Kohler G, and C. Milstein Continuous cultures of fused cells secreting antibody of predefined specificity. 1975. Nature 256: 495-497; Lane, R. D. A short duration polyethylene glycol fusion technique for increasing production of monoclonal antibody-secreting hybridomas. 1985. J. Immunol. Meth. 81:223-228;

Harlow, E. and D. Lane. Antibodies: A laboratory manual. Cold Spring Harbour Laboratory Press. 1988; Kubitz, D. The Scripps Research Institute. La Jolla. Personal Communication; Zhong, G., Berry, J. D., and Choukri, S. (1996) Mapping epitopes of *Chlamydia trachomatis* neutralizing monoclonal antibodies using phage random peptide libraries. J. Indust. Microbiol. Biotech. 19, 71-76; Berry, J. D., Licea, A., Popkov, M., Cortez, X., Fuller, R., Elia, M., Kerwin, L., and C. F. Barbas III. (2003) Rapid monoclonal antibody generation via dendritic cell targeting in vivo. Hybridoma and Hybridomics 22 (1), 23-31.

6. mRNA Expression

Validation in Tissues by TAQMAN

Expression of mRNA is quantitated by RT-PCR using TAQMAN technology. The TAQMAN system couples a 5' fluorogenic nuclease assay with PCR for real time quantitation. A probe is used to monitor the formation of the amplification product.

Total RNA is isolated from disease model cell lines using the RNEasy Kit® (Qiagen) per manufacturer's instructions and included DNase treatment. Normal human tissue RNAs are acquired from commercial vendors (Ambion, Austin, Tex.; Stratagene, La Jolla, Calif., BioChain Institute, Newington, N.H.) as were RNAs from matched disease/normal tissues.

Target transcript sequences are identified for the differentially expressed peptides by searching the BlastP database. TAQMAN assays (PCR primer/probe set) specific for those transcripts are identified by searching the Celera Discovery System™ (CDS) database. The assays are designed to span exon-exon borders and do not amplify genomic DNA.

The TAQMAN primers and probe sequences are as designed by Applied Biosystems (AB) as part of the Assays on Demand™ product line or by custom design through the AB Assays by Design$^{SM}$ service.

RT-PCR is accomplished using AMPLITAQGOLD and MULTISCRIBE reverse transcriptase in the ONE STEP RT-PCR Master Mix reagent kit (AB) according to the manufacturer's instructions. Probe and primer concentrations are 250 nM and 900 nM, respectively, in a 15 µl reaction. For each experiment, a master mix of the above components is made and aliquoted into each optical reaction well. Eight nanograms of total RNA is the template. Each sample is assayed in triplicate. Quantitative RT-PCR is performed using the ABI Prism® 7900HT Sequence Detection System (SDS). Cycling parameters follow: 48° C. for 30 min. for one cycle; 95° C. for 10 min for one cycle; 95° C. for 15 sec, 60° C. for 1 min. for 40 cycles.

The SDS software calculates the threshold cycle ($C_T$) for each reaction, and $C_T$ values are used to quantitate the relative amount of starting template in the reaction. The $C_T$ values for each set of three reactions are averaged for all subsequent calculations Data are analyzed for fold difference in expression using an endogenous control for normalization and is expressed relative to a normal tissue or normal cell line reference. The choice of endogenous control is determined empirically by testing various candidates against the cell line and tissue RNA panels and selecting the one with the least variation in expression. Relative changes in expression are quantitated using the $2^{-\Delta\Delta C_T}$ Method. Livak, K. J. and Schmittgen, T. D. (2001) Methods 25: 402-408; User bulletin #2: ABI PRISM 7700 Sequence Detection System.

Validation by Tissue Flow Cytometry Analysis

Post tissue processing, cells are sorted by flow cytometry known in the art to enrich for epithelial cells. Alternatively, cells isolated from tissue are stained directly with EpCAM (for epithelial cells) and the specific antibody to Maba. Cell numbers and viability are determined by PI exclusion (GUAVA) for cells isolated from both normal and tumor tissue. A minimum of $0.5 \times 10^6$ cells are used for each analysis. Cells are washed once with Flow Staining Buffer (0.5% BSA, 0.05% NaN3 in D-PBS). To the cells, 20 ul of each antibody for Maba are added. An additional 5 ul of EpCAM antibody conjugated to APC were added when unsorted cells are used in the experiment. Cells are incubated with antibodies for 30 minutes at 4° C. Cells are washed once with Flow Staining Buffer and either analyzed immediately on the LSR flow cytometry apparatus or fixed in 1% formaldehyde and store at 4° C. until LSR analysis. Antibodies used to detect Maba may be purchased from BD Biosciences and PE-conjugated. The isotype control antibody used for these experiments is PE-conjugated mouse IgG1k.

7. Detection and Diagnosis of Maba by Liquid Chromatography and Mass Spectrometry (LC/MS)

The proteins from cells can be prepared by methods known in the art (R. Aebersold Nature Biotechnology Volume 21 Number 6 Jun. 2003).

The differential expression of proteins in disease and healthy samples are quantitated using Mass Spectrometry and ICAT (Isotope Coded Affinity Tag) labeling, which is known in the art. ICAT is an isotope label technique that allows for discrimination between two populations of proteins, such as a healthy and a disease sample that are pooled together for experimental purposes or two acquisitions of the same sample for classification of true sample peptides from LC/MS noise artifacts. The LC/MS spectra are collected for the labeled samples and processed using the following steps:

The raw scans from the LC/MS instrument are subjected to peak detection and noise reduction software. Filtered peak lists are then used to detect 'features' corresponding to specific peptides from the original sample(s). Features are characterized by their mass/charge, charge, retention time, isotope pattern and intensity.

Similar experiments are repeated in order to increase the confidence in detection of a peptide. These multiple acquisitions are computationally aggregated into one experiment. Experiments involving healthy and disease samples used the known effects of the ICAT label to classify the peptides as originating from a particular sample or from both samples. The intensity of a peptide present in both healthy and disease samples is used to calculate the differential expression, or relative abundance, of the peptide. The intensity of a peptide found exclusively in one sample is used to calculate a theoretical expression ratio for that peptide (singleton). Expression ratios are calculated for each peptide of each replicate of the experiment.

Statistical tests are performed to assess the robustness of the data and select statistically significant differentials. To assess general quality of the data, one: a) ensured that similar features are detected in all replicates of the experiment; b) assessed the distribution of the log ratios of all peptides (a Gaussian is expected); c) calculated the overall pair wise correlations between ICAT LC/MS maps to ensure that the expression ratios for peptides are reproducible across the multiple replicates; d) aggregated multiple experiments in order to compare the expression ratio of a peptide in multiple diseases or disease samples.

8. Expression Validation by IHC in Tissue Sections

Tissue Sections

Paraffin embedded, fixed tissue sections are obtained from a panel of normal tissues (Adrenal, Bladder, Lymphocytes, Bone Marrow, Breast, Cerebellum, Cerebral cortex, Endothelium, Eye, Fallopian tube, Small Intestine, Heart, Kidney [glomerulus, tubule], Liver, Lung, Testes and Thyroid) as well as 30 tumor samples with matched normal adjacent tissues from pancreas, lung, prostate, ovarian and breast. In addition, other tissues are selected for testing such as bladder, renal, hepatocellular, pharyngeal and gastric tumor tissues. Replicate sections are also obtained from numerous tumor types (Bladder Cancer, Lung Cancer, Breast Cancer, Melanoma, Non-Hodgkins Lymphoma, Endometrial Cancer, Ovarian Cancer, Head and Neck Cancer, Prostate Cancer, Leukemia [ALL and CML] and Rectal Cancer). Sections are stained with hemotoxylin and eosin and histologically examined to ensure adequate representation of cell types in each tissue section.

An identical set of tissues will be obtained from frozen sections and are used in those instances where it is not possible to generate antibodies that are suitable for fixed sections. Frozen tissues do not require an antigen retrieval step.

Paraffin Fixed Tissue Sections

Hemotoxylin and Eosin staining of paraffin embedded, fixed tissue sections.

Sections are deparaffinized in 3 changes of xylene or xylene substitute for 2-5 minutes each. Sections are rinsed in 2 changes of absolute alcohol for 1-2 minutes each, in 95% alcohol for 1 minute, followed by 80% alcohol for 1 minute. Slides are washed well in running water and stained in Gill solution 3 hemotoxylin for 3 to 5 minutes. Following a vigorous wash in running water for 1 minute, sections are stained in Scott's solution for 2 minutes. Sections are washed for 1 min in running water then conterstained in Eosin solution for 2-3 minutes depending upon development of desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimisation of Antibody Staining

For each antibody, a positive and negative control sample are generated using data from the ICAT analysis of the cancer cell lines/tissues. Cells are selected that are known to express low levels of a particular target as determined from the ICAT data. This cell line is the reference normal control. Similarly, a cancer cell line that is determined to over-express the target is selected.

Antigen Retrieval

Sections are deparaffinized and rehydrated by washing 3 times for 5 minutes in xylene; two times for 5 minutes in 100% ethanol; two times for 5 minutes in 95% ethanol; and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4. Alternatively, where necessary sections are deparrafinized by High Energy Antigen Retrieval as follows: sections are washed three times for 5 minutes in xylene; two times for 5 minutes in 100% ethanol; two times for 5 minutes in 95% ethanol; and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are repeated four times (depending on tissue), followed by cooling for 20 minutes at room temperature. Sections are then rinsed in deionized water, two times for 5 minutes, placed in modified endogenous oxidation blocking solution (PBS+2% hydrogen peroxide) and rinsed for 5 minutes in PBS.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. (The choice of blocking serum is the same as the species of the biotinylated secondary antibody). Excess antibody is gently removed by shaking and sections covered with primary antibody diluted in PBA and incubated either at room temperature for 1 hour or overnight at 4° C. (Care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum is used to decrease the background on rat tissue sections. Following incubation, sections are rinsed twice for 5 minutes in PBS, shaking gently. Excess PBS is removed and sections incubated for 1 hour at room temperature in VECTASTAIN ABC reagent (as per kit instructions). The lid of the humidity chamber is secured during all incunations to ensure a moist environment. Sections are rinsed twice for 5 minutes in PBS, shaking gently.

Develop and Counterstain

Sections are incubated for 2 minutes in peroxidase substrate solution that is made up immediately prior to use as follows:

10 mg diaminobenzidine (DAB) dissolved in 10 ml 50 mM sodium phosphate buffer, pH 7.4.
12.5 microliters 3% CoCl2/NiCl2 in deionized water
1.25 microliters hydrogen peroxide Slides are rinsed well three times for 10 min in deionized water and counterstained with 0.01% Light Green acidified with 0.01% acetic acid for 1-2 minutes depending on intensity of counterstain desired.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

9. IHC Staining of Frozen Tissue Sections

Fresh tissues are embedded carefully in OCT in plastic mold, without trapping air bubbles surrounding the tissue. Tissues are frozen by setting the mold on top of liquid nitrogen until 70-80% of the block turns white at which point the mold is placed on dry ice. The frozen blocks were stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for long term storage.)

Sections are fixed by immersing in acetone jar for 1-2 minutes at room temperature, followed by drying at room temp. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation a chamber for 1 hour at room temperature. Without letting the sections dry out, the secondary antibody (diluted in Tris-saline/2.5% serum) is added in a similar manner to the primary and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 ul of diluted alkaline phosphatase conjugated streptavidin, incubated for 30 minutes at room temperature and washed as above. Sections are incubated with alkaline phosphatse substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. Assay for Antibody Dependent Cellular Cytotoxicity

Cultured tumor cells are labeled with 100 µCi $^{51}$Cr for 1 hour; Livingston, P. O., Zhang, S., Adluri, S., Yao, T.-J., Graeber, L., Ragupathi, G., Helling, F., & Fleischer, M. (1997). Cancer Immunol. Immunother. 43, 324-330. After being washed three times with culture medium, cells are resuspended at $10^5$/ml, and 100 µl/well are plated onto 96-well round-bottom plates. A range of antibody concentrations are applied to the wells, including an isotype control together with donor peripheral blood mononuclear cells that are plated at a 100:1 and 50:1 ratio. After an 18-h incubation at 37° C., supernatant (30 µl/well) is harvested and transferred onto Lumaplate 96 (Packard), dried, and read in a Packard Top-Count NXT γ counter. Each measurement is carried out in triplicate. Spontaneous release is determined by cpm of tumor cells incubated with medium and maximum release by cpm of tumor cells plus 1% TRITON X-100 (Sigma). Specific lysis is defined as: % specific lysis=[(experimental release−spontaneous release)/(maximum release−spontaneous release)]×100. The percent ADCC is expressed as peak specific lysis postimmune subtracted by preimmune percent specific lysis. A doubling of the ADCC to >20% is considered significant.

11. Assay for Complement Dependent Cytotoxicity

Chromium release assays to assess complement-mediated cytotoxicity are performed for each patient at various time points; Dickler, M. N., Ragupathi, G., Liu, N. X., Musselli, C., Martino, D. J., Miller, V. A., Kris, M. G., Brezicka, F. T., Livingston, P. O. & Grant, S. C. (1999) Clin. Cancer Res. 5, 2773-2779. Cultured tumor cells are washed in FCS-free media two times, resuspended in 500 μl of media, and incubated with 100 μCi $^{51}$Cr per 10 million cells for 2 h at 37° C. The cells are then shaken every 15 min for 2 h, washed 3 times in media to achieve a concentration of approximately 20,000 cells/well, and then plated in round-bottom plates. The plates contain either 50 μl cells plus 50 μl monoclonal antibody, 500 cells plus serum (pre- and posttherapy), or 50 μl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 μl. Control wells include those for maximum release of isotope in 10% TRITON X-100 (Sigma) and for spontaneous release in the absence of complement with medium alone. The plates are incubated for 2 h at 37° C., centrifuged for 3 min, and then 100 μl of supernatant is removed for radioactivity counting. The percentage of specific lysis is calculated as follows: % cytotoxicity=[(experimental release−spontaneous release)/(maximum release-spontaneous release)]×100. A doubling of the CDC to >20% is considered significant.

12. In Vitro Assays in Cell Lines

RNAi

LIPOFECTAMINE 2000 and PLUS were purchased from Invitrogen (Carlsbad, Calif.) and GENESILENCER from Gene Therapy Systems (San Diego, Calif.). Synthetic siRNA oligonucleotides were from Dharmacon (Lafayette, Colo.), Qiagen (Valencia, Calif.). RNEASY 96 Kit was purchased from Qiagen (Valencia, Calif.). APOP-ONE HOMOGENEOUS CASPASE-3/7 kit and CELLTITER 96 AQUEOUS ONE solution cell proliferation assay were both purchased from Promega (Madison, Wis.). Alamar Blue proliferation assay was purchased from Biosource (Camarillo, Calif.).

RNAi Transfections

In the initial screening phase, RNAi was performed by using 100 nM (final) of SMARTPOOLS (Dharmacon), pool of 4- for Silencing siRNA duplexes (Qiagen) or non-targeting negative control siRNA (Dharmacon or Qiagen). In the breakout phase, each individual duplex was used at 100 nM (final). In the titration phase, individual duplex were used at 0.1-100 nM (final). Transient transfections were carried out by using either LIPOFECTAMINE 2000 from Invitrogen (Carlsbad, Calif.) or by using GENESILENCER from Gene Therapy Systems (San Diego, Calif.) in methods described below. 1 day after transfections, total RNA was isolated by using the RNEASY 96 Kit (Qiagen) according to manufacturer's instructions and expression of mRNA was quantitated by using TAQMAN technology. Apoptosis and proliferation assays were performed daily using APOP-ONE HOMOGENEOUS CASPASE-3/7 kit and Alamar Blue or CELLTITER 96 AQUEOUS ONE SOLUTION CELL PROLIFERATION ASSAYS (see below).

RNAi Transfections-Lipofectamine 2000

Transient transfections were carried out on sub-confluent cancer cell lines as previously described (Elbashir, S. M. et al. (2001) Nature 411: 494-498, Caplen, N. J. et al. (2001) Proc Natl Acad Sci USA 98: 9742-9747, Sharp, P. A. (2001) Genes and Development 15: 485-490). Synthetic RNA to gene of interest or non-targeting negative control siRNA were transfected using lipofectamine according to manufacturer's instructions. Cells were plated in 96 well plates in antibiotics free medium. The next day, the transfection reagent and siRNA were prepared for transfections as follows: For each well, 0.1-100 nM siRNA was resuspended in 25 ul serum-free media with PLUS and incubated at room temperature for 15 minutes. 0.1-1 ul of LIPOFECTAMINE 2000 was then resuspended in serum-free medium. After incubation, the diluted siRNA and the LIPOFECTAMINE 2000 were combined and incubated for 15 minutes at room temperature. Media was then removed from the cells and the combined siRNA-LIPOFECTAMINE 2000 reagent added to a final volume of 50 ul per well. After a further 4 hours incubation, 50 ul serum containing medium was added to each well. 1 and 4 days after transfection, expression of mRNA was quantitated by RT-PCR using TAQMAN technology and protein expression levels were examined by flow cytometry. Apoptosis and proliferation assays were performed daily using Apop-one homogeneous caspase-3/7 kit and Alamar Blue or CELLTITER 96 AQUEOUS ONE SOLUTION CELL PROLIFERATION ASSAYS (see below).

RNAi Transfections—GENESILENCER

Transient transfections were carried out on sub-confluent cancer cell lines as previously described. Synthetic RNA to gene of interest or scrambled negative control siRNA were transfected using GENESILENCER according to manufacturer's instructions. Cells were plated in 96 well plates in antibiotics free medium. The next day, the transfection reagent and the synthetic siRNA were prepared for transfections as follows: 1-1.5 ul of GENE SILENCER was diluted in serum-free media to a final volume of 20 ul per well. After resuspending 0.1-100 nM siRNA in 20 ul serum-free media, the reagents were combined and incubated at room temperature for 5-20 minutes. After incubation, the siRNA-GENE SILENCER reagent was added to each well to a final volume of 50 ul per well. After further incubation in a 37° C. incubator for 4 hours, an equal volume of serum containing media was added back to the cultured cells. The cells were then incubated for 1 to 4 days before mRNA, protein expression and effects on apoptosis and proliferation were examined.

Apoptosis

Apoptosis assay was performed by using the APOP-ONE HOMOGENEOUS CASPASE-3/7 kit from Promega. Briefly, the caspase-3/7 substrate was thawed to room temperature and diluted 1:100 with buffer. The diluted substrate was then added 1:1 to cells, control or blank. The plates were then placed on a plate shaker for 30 minutes to 18 hours at 300-500 rpm. The fluorescence of each well was then measured at using an excitation wavelength of 485+/−20 nm and an emission wavelength of 530+/−25 nm.

Proliferation—MTS

Proliferation assay was performed by using the CELLTITER 96 AQUEOUS ONE SOLUTION CELL PROLIFERATION ASSAY kit from Promega. 20 ul of CELLTITER 96 AQUEOUS ONE SOLUTION was added to 100 ul of culture medium. The plates were then incubated for 1-4 hours at 37° C. in a humidified 5% CO2 incubator. After incubation, the change in absorbance was read at 490 nm.

Proliferation—Alamar Blue

Proliferation assay was performed by using the Alamar Blue assay from Biosource. 10 ul of Alamar Blue reagent was added to 100 ul of cells in culture medium. The plates were then incubated for 1-4 hours at 37° C. in a humidified 5% $CO_2$ incubator. After incubation, the change in fluorescence was measured at using an excitation wavelength of 530 nm and an emission wavelength of 595 nm.

mRNA Expression

Expression of mRNA was quantitated by RT-PCR using TaqMan® technology. Total RNA was isolated from cancer model cell lines using the RNEASY 96 kit (Qiagen) per manufacturer's instructions and included DNase treatment. Target transcript sequences were identified for the differentially expressed peptides by searching the BlastP database. TAQMAN assays (PCR primer/probe set) specific for those transcripts were identified by searching the Celera Discovery System™ (CDS) database. The assays are designed to span exon-exon borders and do not amplify genomic DNA. The TAQMAN primers and probe sequences were as designed by Applied Biosystems (AB) as part of the Assays on Demand™ product line or by custom design through the AB Assays by Design$^{SM}$ service. RT-PCR was accomplished using AMPLI-TAQGOLD and MULTISCRIBE reverse transcriptase in the ONE STEP RT-PCR MASTER MIX reagent kit (AB) according to the manufacturers instructions. Probe and primer concentrations were 900 nM and 250 nM, respectively, in a 250 reaction. For each experiment, a master mix of the above components was made and aliquoted into each optical reaction well. 5 ul of total RNA was the template. Each sample was assayed in triplicate. Quantitative RT-PCR was performed using the ABI Prism® 7900HT Sequence Detection System (SDS). Cycling parameters follow: 48° for 30 min. for one cycle; 95° C. for 10 min for one cycle; 95° C. for 15 sec, 60° C. for 1 min. for 40 cycles.

The SDS software calculates the threshold cycle (CT) for each reaction, and CT values were used to quantitate the relative amount of starting template in the reaction. The CT values for each set of three reactions were averaged for all subsequent calculations.

Total RNA was quantitated by using RIBOGREEN RNA QUANTITATION KIT according to manufacturer's instructions and the % mRNA expression was calculated using total RNA for normalization. % knockdown was then calculated relative to the no addition control.

Testing of Functional Blocking Antibodies

Sub-confluent cancer cell lines are serum-starved overnight. The next day, serum-containing media is added back to the cells in the presence of 5-50 ng/ml of function blocking antibodies. After 2 or 5 days incubation at 37° C. 5% $CO_2$, antibody binding is examined by flow cytometry and apoptosis and proliferation are examined by using protocols described below.

Cell Invasion

Cell invasion assay is performed by using the 96 well cell invasion assay kit available from Chemicon. After the cell invasion chamber plates are adjusted to room temperature, 100 ul serum-free media is added to the interior of the inserts. 1-2 hours later, cell suspensions of $1 \times 10^6$ cells/ml are prepared. Media is then carefully removed from the inserts and 100 ul of prepared cells are added into the insert +/−0 to 50 ng function blocking antibodies. The cells are pre-incubated for 15 minutes at 37° C. before 150 ul of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 ul of pre-warmed cell detachment solution in the wells. The plates are incubated for 30 minutes at 37° C. and are periodically shaken. Lysis buffer/dye solution (4 ul CYQUANT DYE/300 ul 4× lysis buffer) is prepared and added to each well of dissociation buffer/cells on feeder tray. The plates are incubated for 15 minutes at room temperature before 150 ul is transferred to a new 96-well plate. Fluorescence of invading cells is then read at 480 nm excitation and 520 nm emission.

Receptor Internalization

For quantification of receptor internalization, ELISA assays are performed essentially as described by Daunt et al. (Daunt, D. A., Hurtz, C., Hein, L., Kallio, J., Feng, F., and Kobilka, B. K. (1997) Mol. Pharmacol. 51, 711-720.) The cell lines are plated at $6 \times 10^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface target of interest is then added at a pre-determined concentration in prewarmed DMEM to the wells. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 hr at room temperature. Three washes with TBS followed, and cells are briefly reblocked for 15 min at room temperature. Incubation with goat anti-mouse conjugated alkaline phosphatase (Bio-Rad) diluted 1:1000 in TBS/BSA is carried out for 1 h at room temperature. The cells are washed three times with TBS and a colorimetric alkaline phosphatase substrate is added. When the adequate color change is reached, 100-0 samples are taken for colorimetric readings.

13. In Vivo Studies by Using Antibodies

Treatment of Cancer Cells with Monoclonal Antibodies

Cancer cells are seeded at a density of $4 \times 10^4$ cells per well in 96-well microtiter plates and allowed to adhere for 2 hours. The cells are then treated with different concentrations of anti-Maba monoclonal antibody (Mab) or irrelevant isotype matched (anti-rHuIFN-. gamma. Mab) at 0.05, 0.5 or 5.0 mug/ml. After a 72 hour incubation, the cell monolayers are stained with crystal violet dye for determination of relative percent viability (RPV) compared to control (untreated) cells. Each treatment group consists of replicates. Cell growth inhibition is monitored.

Treatment of NIH 3T3 Cells Overexpression Maba Protein with Monoclonal Antibodies.

NIH 3T3 expressing Maba protein are treated with different concentrations of anti-Maba MAbs. Cell growth inhibition is monitored.

In Vivo Treatment of NIH 3T3 Cells Overexpressing Maba with Anti-Maba Monoclonal Antibodies.

NIH 3T3 cells transfected with either a Maba expression plasmid or the neo-DHFR vector are injected into nu/nu (athymic) mice subcutaneously at a dose of $10^6$ cells in 0.1 ml of phosphate-buffered saline. On days 0, 1, 5 and every 4 days thereafter, 100 mug (0.1 ml in PBS) of either an irrelevant or anti-Maba monoclonal antibody of the IG2A subclass is injected intraperitoneally. Tumor occurrence and size are monitored for 1 month period of treatment.

14. Summary of Experimental Validation

Multiple Maba peptides were identified by mass spectrometry as overexpressed in lung (3.2 to 4.3-fold) and breast (6.3 to 7.4-fold) tumor tissues and in breast cancer cell lines (4.2 to 18.7-fold). Immunohistochemistry (IHC) confirms expression of Maba in lung and breast tumors.

Overexpression of Maba was measured by IHC in the following tumor types: kidney (overexpressed in 100% of tumors), melanoma (50%), ovary (40-50%), liver (38%), lung (squamous) (60%), lung (NSC) (40%), bladder (30%), and breast (20%).

RNAi knockdown of Maba mediates a decrease (e.g., 27% decrease) in cell proliferation in breast cancer cells (FIGS. 3-4, 6, and 8).

Cell surface expression of Maba was confirmed by FACS in multiple breast cancer cell lines.

Cross-tissue analysis of Maba reveals elevated breast cancer expression.

Figure 5:
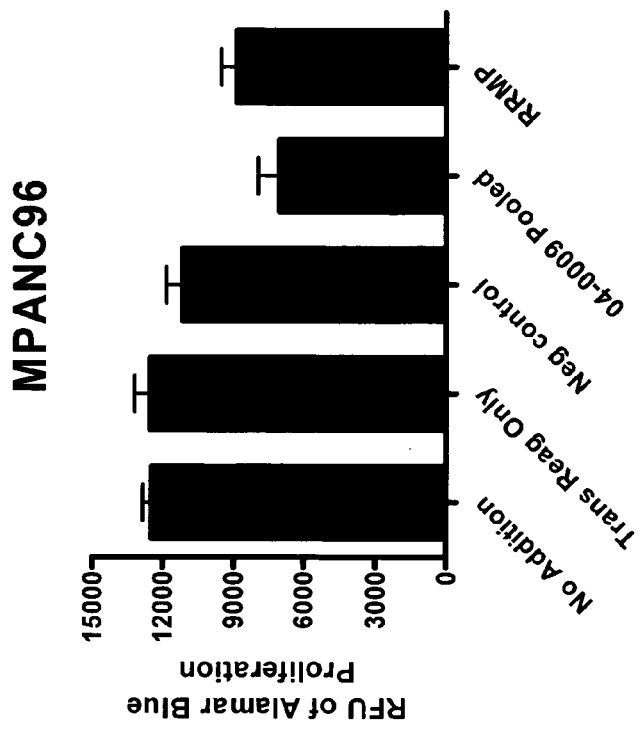
FIG. 5. Maba siRNA Inhibits Cell Proliferation in Pancreatic Cancer Cell Line MPANC96.

RNAi knockdown of Maba inhibits cell proliferation in a pancreatic cancer cell line (FIG. 5).

Figure 6:
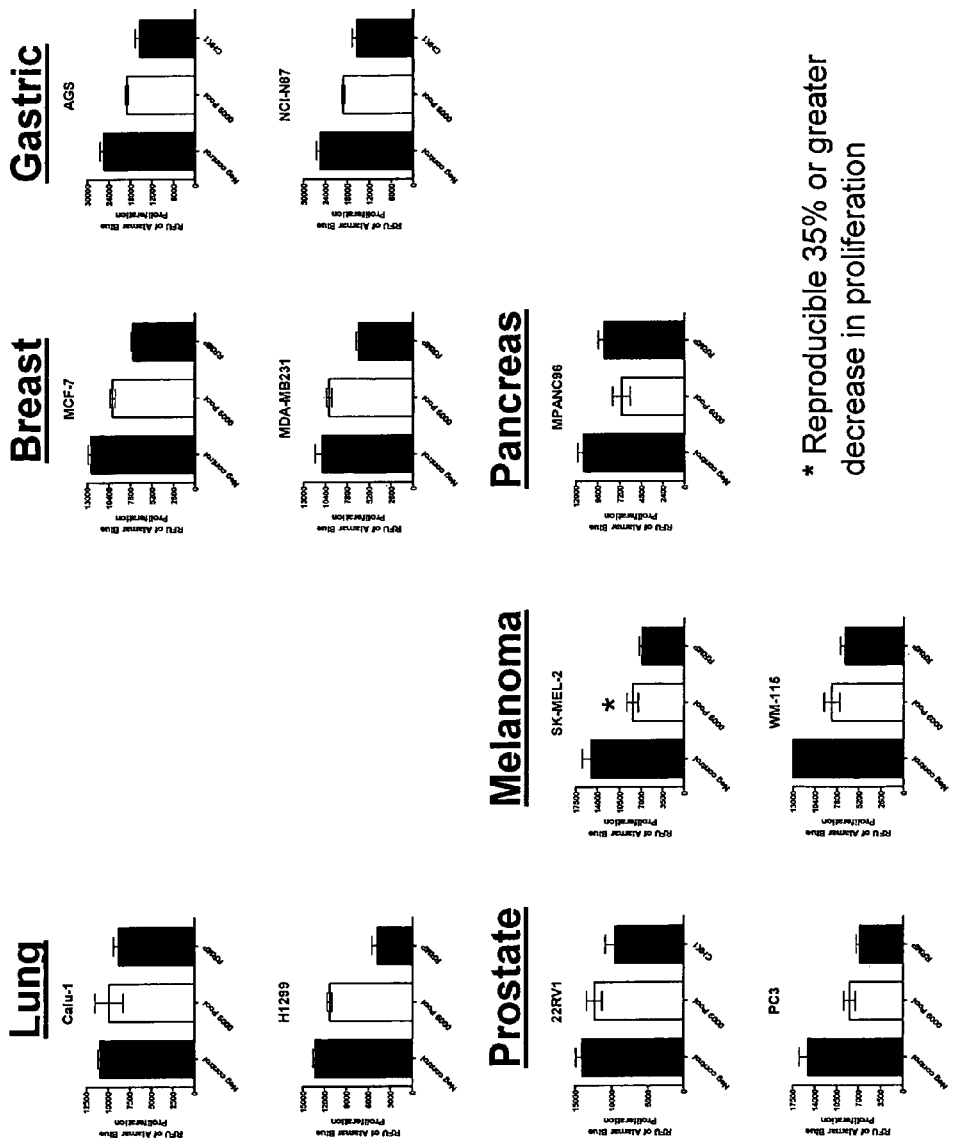
FIG. 6. Maba siRNA Screen Data: Anti-Proliferation Activity.
Figure 7:
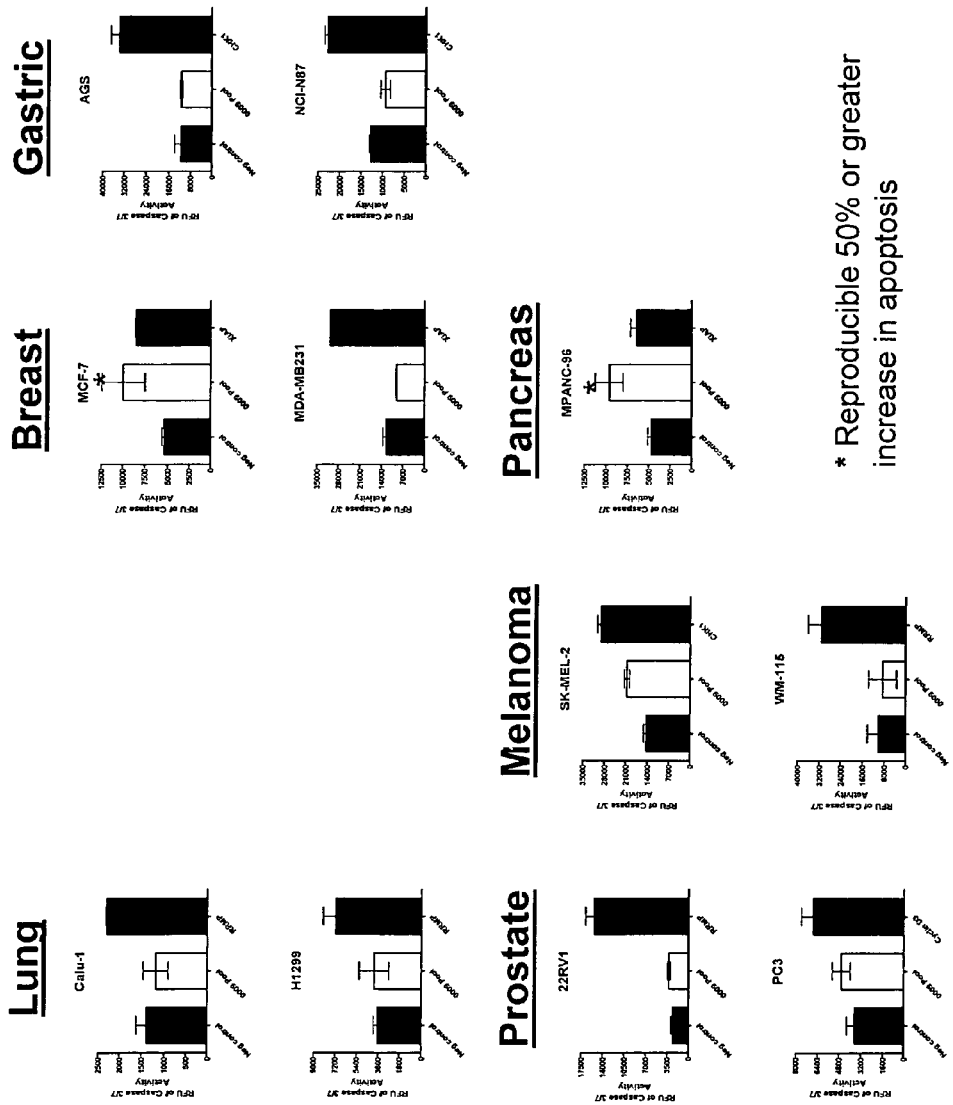
FIG. 7. Maba siRNA Screen Data: Apoptosis Activity.
Figure 8:
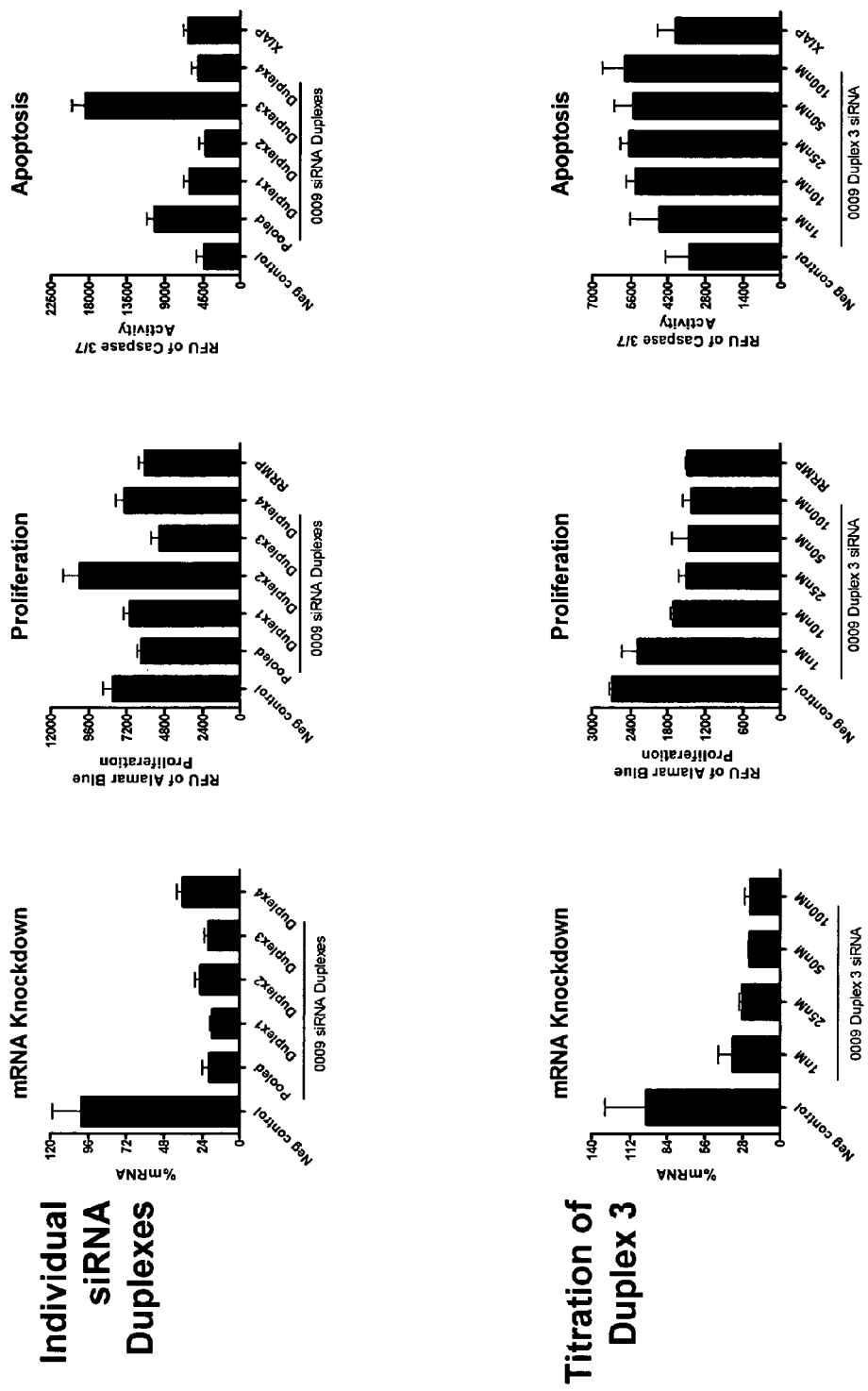
FIG. 8. Maba Individual siRNA Duplex Data: Anti-Proliferation and Apoptosis Activity—MCF-7 Breast Carcinoma.

RNAi knockdown of Maba results in a decrease in cell proliferation in gastric cancer and melanoma cell lines, as well as other cancer cell lines (FIG. 6).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

SEQUENCE LISTING

```
<160> NUMBER OF SEQ ID NOS: 17

<210> SEQ ID NO 1
<211> LENGTH: 703
<212> TYPE: PRT
<213> ORGANISM: Homo sapiens

<400> SEQUENCE: 1

Met Ser Ser Gln Glu Val Thr Phe Glu Gln Arg Pro Glu Gly Asp Glu
 1               5                  10                  15

Gly Gly Ala Val Glu Leu Ser Arg Gln Gln Thr Gln Gln Glu Arg Arg
            20                  25                  30

Arg Gln Leu Gly Gln Thr Gln Leu Met Tyr Lys Trp Ala Lys Pro Lys
        35                  40                  45

Ile Cys Ser Glu Asp Leu Glu Gly Ala Val Lys Leu Pro Ala Ser Gly
    50                  55                  60

Val Lys Thr His Cys Pro Pro Cys Asn Pro Gly Phe Phe Lys Thr Asn
65                  70                  75                  80

Asn Ser Thr Cys Gln Pro Cys Pro Tyr Gly Ser Tyr Ser Asn Gly Ser
                85                  90                  95

Asp Cys Thr Arg Cys Pro Ala Gly Thr Glu Pro Ala Val Gly Phe Glu
            100                 105                 110

Tyr Lys Trp Trp Asn Thr Leu Pro Thr Asn Met Glu Thr Thr Val Leu
        115                 120                 125

Ser Gly Ile Asn Phe Glu Tyr Lys Gly Met Thr Gly Trp Glu Val Ala
    130                 135                 140

Gly Asp His Ile Tyr Thr Ala Ala Gly Ala Ser Asp Asn Asp Phe Met
145                 150                 155                 160

Ile Leu Thr Leu Val Val Pro Gly Phe Arg Pro Pro Gln Ser Val Met
                165                 170                 175

Ala Asp Thr Glu Asn Lys Glu Val Ala Arg Ile Thr Phe Val Phe Glu
            180                 185                 190

Thr Leu Cys Ser Val Asn Cys Glu Leu Tyr Phe Met Val Gly Val Asn
        195                 200                 205

Ser Arg Thr Asn Thr Pro Val Glu Thr Trp Lys Gly Ser Lys Gly Lys
    210                 215                 220

Gln Ser Tyr Thr Tyr Ile Ile Glu Glu Asn Thr Thr Thr Ser Phe Thr
225                 230                 235                 240

Trp Ala Phe Gln Arg Thr Thr Phe His Glu Ala Ser Arg Lys Tyr Thr
                245                 250                 255

Asn Asp Val Ala Lys Ile Tyr Ser Ile Asn Val Thr Asn Val Met Asn
            260                 265                 270
```

```
Gly Val Ala Ser Tyr Cys Arg Pro Cys Ala Leu Glu Ala Ser Asp Val
            275                 280                 285

Gly Ser Ser Cys Thr Ser Cys Pro Ala Gly Tyr Tyr Ile Asp Arg Asp
            290                 295                 300

Ser Gly Thr Cys His Ser Cys Pro Pro Asn Thr Ile Leu Lys Ala His
305                 310                 315                 320

Gln Pro Tyr Gly Val Gln Ala Cys Val Pro Cys Gly Pro Gly Thr Lys
                325                 330                 335

Asn Asn Lys Ile His Ser Leu Cys Tyr Asn Asp Cys Thr Phe Ser Arg
                340                 345                 350

Asn Thr Pro Thr Arg Thr Phe Asn Tyr Asn Phe Ser Ala Leu Ala Asn
            355                 360                 365

Thr Val Thr Leu Ala Gly Gly Pro Ser Phe Thr Ser Lys Gly Leu Lys
            370                 375                 380

Tyr Phe His His Phe Thr Leu Ser Leu Cys Gly Asn Gln Gly Arg Lys
385                 390                 395                 400

Met Ser Val Cys Thr Asp Asn Val Thr Asp Leu Arg Ile Pro Glu Gly
                405                 410                 415

Glu Ser Gly Phe Ser Lys Ser Ile Thr Ala Tyr Val Cys Gln Ala Val
            420                 425                 430

Ile Ile Pro Pro Glu Val Thr Gly Tyr Lys Ala Gly Val Ser Ser Gln
            435                 440                 445

Pro Val Ser Leu Ala Asp Arg Leu Ile Gly Val Thr Thr Asp Met Thr
450                 455                 460

Leu Asp Gly Ile Thr Ser Pro Ala Glu Leu Phe His Leu Glu Ser Leu
465                 470                 475                 480

Gly Ile Pro Asp Val Ile Phe Phe Tyr Arg Ser Asn Asp Val Thr Gln
                485                 490                 495

Ser Cys Ser Ser Gly Arg Ser Thr Thr Ile Arg Val Arg Cys Ser Pro
                500                 505                 510

Gln Lys Thr Val Pro Gly Ser Leu Leu Pro Gly Thr Cys Ser Asp
            515                 520                 525

Gly Thr Cys Asp Gly Cys Asn Phe His Phe Leu Trp Glu Ser Ala Ala
            530                 535                 540

Ala Cys Pro Leu Cys Ser Val Ala Asp Tyr His Ala Ile Val Ser Ser
545                 550                 555                 560

Cys Val Ala Gly Ile Gln Lys Thr Thr Tyr Val Trp Arg Glu Pro Lys
                565                 570                 575

Leu Cys Ser Gly Gly Ile Ser Leu Pro Glu Gln Arg Val Thr Ile Cys
            580                 585                 590

Lys Thr Ile Asp Phe Trp Leu Lys Val Gly Ile Ser Ala Gly Thr Cys
            595                 600                 605

Thr Ala Ile Leu Leu Thr Val Leu Thr Cys Tyr Phe Trp Lys Lys Asn
            610                 615                 620

Gln Lys Leu Glu Tyr Lys Tyr Ser Lys Leu Val Met Asn Ala Thr Leu
625                 630                 635                 640

Lys Asp Cys Asp Leu Pro Ala Ala Asp Ser Cys Ala Ile Met Glu Gly
                645                 650                 655

Glu Asp Val Glu Asp Asp Leu Ile Phe Thr Ser Lys Lys Ser Leu Phe
            660                 665                 670

Gly Lys Ile Lys Ser Phe Thr Ser Lys Arg Thr Pro Asp Gly Phe Asp
            675                 680                 685

Ser Val Pro Leu Lys Thr Ser Ser Gly Gly Pro Asp Met Asp Leu
690                 695                 700
```

-continued

<210> SEQ ID NO 2
<211> LENGTH: 1013
<212> TYPE: PRT
<213> ORGANISM: Homo sapiens

<400> SEQUENCE: 2

```
Met Ala Glu Pro Gly His Ser His His Leu Ser Ala Arg Val Arg Gly
  1               5                  10                  15

Arg Thr Glu Arg Arg Ile Pro Arg Leu Trp Arg Leu Leu Leu Trp Ala
             20                  25                  30

Gly Thr Ala Phe Gln Val Thr Gln Gly Thr Gly Pro Glu Leu His Ala
         35                  40                  45

Cys Lys Glu Ser Glu Tyr His Tyr Glu Tyr Thr Ala Cys Asp Ser Thr
 50                  55                  60

Gly Ser Arg Trp Arg Val Ala Val Pro His Thr Pro Gly Leu Cys Thr
 65                  70                  75                  80

Ser Leu Pro Asp Pro Val Lys Gly Thr Glu Cys Ser Phe Ser Cys Asn
                 85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Val Gln Asn
        195                 200                 205

Asp Gln Cys Gln Pro Asn Ala Asp Asp Ser Arg Trp Met Lys Thr Thr
210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
290                 295                 300

Glu Thr Ser Cys His Gln Cys Asp Pro Asp Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
            340                 345                 350

Lys Trp Ala Lys Pro Lys Ile Cys Ser Glu Asp Leu Glu Gly Ala Val
        355                 360                 365

Lys Leu Pro Ala Ser Gly Val Lys Thr His Cys Pro Pro Cys Asn Pro
370                 375                 380
```

```
Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
            405                 410                 415

Pro Ala Val Gly Phe Glu Tyr Lys Trp Trp Asn Thr Leu Pro Thr Asn
        420                 425                 430

Met Glu Thr Thr Val Leu Ser Gly Ile Asn Phe Glu Tyr Lys Gly Met
    435                 440                 445

Thr Gly Trp Glu Val Ala Gly Asp His Ile Tyr Thr Ala Ala Gly Ala
450                 455                 460

Ser Asp Asn Asp Phe Met Ile Leu Thr Leu Val Pro Gly Phe Arg
465                 470                 475                 480

Pro Pro Gln Ser Val Met Ala Asp Thr Glu Asn Lys Glu Val Ala Arg
            485                 490                 495

Ile Thr Phe Val Phe Glu Thr Leu Cys Ser Val Asn Cys Glu Leu Tyr
        500                 505                 510

Phe Met Val Gly Val Asn Ser Arg Thr Asn Thr Pro Val Glu Thr Trp
    515                 520                 525

Lys Gly Ser Lys Gly Lys Gln Ser Tyr Thr Tyr Ile Ile Glu Glu Asn
530                 535                 540

Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
            565                 570                 575

Val Thr Asn Val Met Asn Gly Val Ala Ser Tyr Cys Arg Pro Cys Ala
        580                 585                 590

Leu Glu Ala Ser Asp Val Gly Ser Ser Cys Thr Ser Cys Pro Ala Gly
    595                 600                 605

Tyr Tyr Ile Asp Arg Asp Ser Gly Thr Cys His Ser Cys Pro Pro Asn
610                 615                 620

Thr Ile Leu Lys Ala His Gln Pro Tyr Gly Val Gln Ala Cys Val Pro
625                 630                 635                 640

Cys Gly Pro Gly Thr Lys Asn Asn Lys Ile His Ser Leu Cys Tyr Asn
            645                 650                 655

Asp Cys Thr Phe Ser Arg Asn Thr Pro Thr Arg Thr Phe Asn Tyr Asn
        660                 665                 670

Phe Ser Ala Leu Ala Asn Thr Val Thr Leu Ala Gly Pro Ser Phe
    675                 680                 685

Thr Ser Lys Gly Leu Lys Tyr Phe His His Phe Thr Leu Ser Leu Cys
690                 695                 700

Gly Asn Gln Gly Arg Lys Met Ser Val Cys Thr Asp Asn Val Thr Asp
705                 710                 715                 720

Leu Arg Ile Pro Glu Gly Glu Ser Gly Phe Ser Lys Ser Ile Thr Ala
            725                 730                 735

Tyr Val Cys Gln Ala Val Ile Ile Pro Pro Glu Val Thr Gly Tyr Lys
        740                 745                 750

Ala Gly Val Ser Ser Gln Pro Val Ser Leu Ala Asp Arg Leu Ile Gly
    755                 760                 765

Val Thr Thr Asp Met Thr Leu Asp Gly Ile Thr Ser Pro Ala Glu Leu
770                 775                 780

Phe His Leu Glu Ser Leu Gly Ile Pro Asp Val Ile Phe Phe Tyr Arg
785                 790                 795                 800

Ser Asn Asp Val Thr Gln Ser Cys Ser Ser Gly Arg Ser Thr Thr Ile
```

```
                           805                 810                 815
Arg Val Arg Cys Ser Pro Gln Lys Thr Val Pro Gly Ser Leu Leu Leu
            820                 825                 830

Pro Gly Thr Cys Ser Asp Gly Thr Cys Asp Gly Cys Asn Phe His Phe
            835                 840                 845

Leu Trp Glu Ser Ala Ala Cys Pro Leu Cys Ser Val Ala Asp Tyr
    850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
            900                 905                 910

Ile Ser Ala Gly Thr Cys Thr Ala Ile Leu Leu Thr Val Leu Thr Cys
            915                 920                 925

Tyr Phe Trp Lys Lys Asn Gln Lys Leu Glu Tyr Lys Tyr Ser Lys Leu
    930                 935                 940

Val Met Asn Ala Thr Leu Lys Asp Cys Asp Leu Pro Ala Ala Asp Ser
945                 950                 955                 960

Cys Ala Ile Met Glu Gly Asp Val Glu Asp Leu Ile Phe Thr
                965                 970                 975

Ser Lys Lys Ser Leu Phe Gly Lys Ile Lys Ser Phe Thr Ser Lys Arg
            980                 985                 990

Thr Pro Asp Gly Phe Asp Ser Val Pro Leu Lys Thr Ser Ser Gly Gly
            995                 1000                1005

Pro Asp Met Asp Leu
    1010

<210> SEQ ID NO 3
<211> LENGTH: 663
<212> TYPE: PRT
<213> ORGANISM: Homo sapiens

<400> SEQUENCE: 3

Met Tyr Lys Trp Ala Lys Pro Lys Ile Cys Ser Glu Asp Leu Glu Gly
1               5                   10                  15

Ala Val Lys Leu Pro Ala Ser Gly Val Lys Thr His Cys Pro Pro Cys
            20                  25                  30

Asn Pro Gly Phe Phe Lys Thr Asn Asn Ser Thr Cys Gln Pro Cys Pro
        35                  40                  45

Tyr Gly Ser Tyr Ser Asn Gly Ser Asp Cys Thr Arg Cys Pro Ala Gly
    50                  55                  60

Thr Glu Pro Ala Val Gly Phe Glu Tyr Lys Trp Trp Asn Thr Leu Pro
65                  70                  75                  80

Thr Asn Met Glu Thr Thr Val Leu Ser Gly Ile Asn Phe Glu Tyr Lys
                85                  90                  95

Gly Met Thr Gly Trp Glu Val Ala Gly Asp His Ile Tyr Thr Ala Ala
            100                 105                 110

Gly Ala Ser Asp Asn Asp Phe Met Ile Leu Thr Leu Val Pro Gly
        115                 120                 125

Phe Arg Pro Pro Gln Ser Val Met Ala Asp Thr Glu Asn Lys Glu Val
    130                 135                 140

Ala Arg Ile Thr Phe Val Phe Glu Thr Leu Cys Ser Val Asn Cys Glu
145                 150                 155                 160

Leu Tyr Phe Met Val Gly Val Asn Ser Arg Thr Asn Thr Pro Val Glu
```

-continued

```
                165                 170                 175
Thr Trp Lys Gly Ser Lys Gly Lys Gln Ser Tyr Thr Tyr Ile Ile Glu
                180                 185                 190

Glu Asn Thr Thr Thr Ser Phe Thr Trp Ala Phe Gln Arg Thr Thr Phe
                195                 200                 205

His Glu Ala Ser Arg Lys Tyr Thr Asn Asp Val Ala Lys Ile Tyr Ser
                210                 215                 220

Ile Asn Val Thr Asn Val Met Asn Gly Val Ala Ser Tyr Cys Arg Pro
225                 230                 235                 240

Cys Ala Leu Glu Ala Ser Asp Val Gly Ser Ser Cys Thr Ser Cys Pro
                245                 250                 255

Ala Gly Tyr Tyr Ile Asp Arg Asp Ser Gly Thr Cys His Ser Cys Pro
                260                 265                 270

Pro Asn Thr Ile Leu Lys Ala His Gln Pro Tyr Gly Val Gln Ala Cys
                275                 280                 285

Val Pro Cys Gly Pro Gly Thr Lys Asn Asn Lys Ile His Ser Leu Cys
                290                 295                 300

Tyr Asn Asp Cys Thr Phe Ser Arg Asn Thr Pro Thr Arg Thr Phe Asn
305                 310                 315                 320

Tyr Asn Phe Ser Ala Leu Ala Asn Thr Val Thr Leu Ala Gly Gly Pro
                325                 330                 335

Ser Phe Thr Ser Lys Gly Leu Lys Tyr Phe His His Phe Thr Leu Ser
                340                 345                 350

Leu Cys Gly Asn Gln Gly Arg Lys Met Ser Val Cys Thr Asp Asn Val
                355                 360                 365

Thr Asp Leu Arg Ile Pro Glu Gly Glu Ser Gly Phe Ser Lys Ser Ile
                370                 375                 380

Thr Ala Tyr Val Cys Gln Ala Val Ile Ile Pro Pro Glu Val Thr Gly
385                 390                 395                 400

Tyr Lys Ala Gly Val Ser Ser Gln Pro Val Ser Leu Ala Asp Arg Leu
                405                 410                 415

Ile Gly Val Thr Thr Asp Met Thr Leu Asp Gly Ile Thr Ser Pro Ala
                420                 425                 430

Glu Leu Phe His Leu Glu Ser Leu Gly Ile Pro Asp Val Ile Phe Phe
                435                 440                 445

Tyr Arg Ser Asn Asp Val Thr Gln Ser Cys Ser Ser Gly Arg Ser Thr
                450                 455                 460

Thr Ile Arg Val Arg Cys Ser Pro Gln Lys Thr Val Pro Gly Ser Leu
465                 470                 475                 480

Leu Leu Pro Gly Thr Cys Ser Asp Gly Thr Cys Asp Gly Cys Asn Phe
                485                 490                 495

His Phe Leu Trp Glu Ser Ala Ala Ala Cys Pro Leu Cys Ser Val Ala
                500                 505                 510

Asp Tyr His Ala Ile Val Ser Ser Cys Val Ala Gly Ile Gln Lys Thr
                515                 520                 525

Thr Tyr Val Trp Arg Glu Pro Lys Leu Cys Ser Gly Gly Ile Ser Leu
                530                 535                 540

Pro Glu Gln Arg Val Thr Ile Cys Lys Thr Ile Asp Phe Trp Leu Lys
545                 550                 555                 560

Val Gly Ile Ser Ala Gly Thr Cys Thr Ala Ile Leu Leu Thr Val Leu
                565                 570                 575

Thr Cys Tyr Phe Trp Lys Lys Asn Gln Lys Leu Glu Tyr Lys Tyr Ser
                580                 585                 590
```

```
Lys Leu Val Met Asn Ala Thr Leu Lys Asp Cys Asp Leu Pro Ala Ala
            595                 600                 605

Asp Ser Cys Ala Ile Met Glu Gly Glu Asp Val Glu Asp Leu Ile
610                 615                 620

Phe Thr Ser Lys Ser Leu Phe Gly Lys Ile Lys Ser Phe Thr Ser
625                 630                 635                 640

Lys Arg Thr Pro Asp Gly Phe Asp Ser Val Pro Leu Lys Thr Ser Ser
                    645                 650                 655

Gly Gly Pro Asp Met Asp Leu
            660

<210> SEQ ID NO 4
<211> LENGTH: 1013
<212> TYPE: PRT
<213> ORGANISM: Homo sapiens

<400> SEQUENCE: 4

Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
            20                  25                  30

Gly Thr Ala Phe Gln Val Thr Gln Gly Thr Gly Pro Glu Leu His Ala
        35                  40                  45

Cys Lys Glu Ser Glu Tyr His Tyr Glu Tyr Thr Ala Cys Asp Ser Thr
    50                  55                  60

Gly Ser Arg Trp Arg Val Ala Val Pro His Thr Pro Gly Leu Cys Thr
65                  70                  75                  80

Ser Leu Pro Asp Pro Val Lys Gly Thr Glu Cys Ser Phe Ser Cys Asn
                85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Glu Trp Asp
        115                 120                 125

Glu Leu Pro His Gly Phe Ala Ser Leu Ser Ala Asn Met Glu Leu Asp
130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Val Gln Asn
        195                 200                 205

Asp Gln Cys Gln Pro Asn Ala Asp Asp Ser Arg Trp Met Lys Thr Thr
210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
290                 295                 300
```

```
Glu Thr Ser Cys His Gln Cys Asp Pro Asp Lys Tyr Ser Glu Lys Gly
305                 310                 315                 320
Ser Ser Ser Cys Asn Val Arg Pro Ala Cys Thr Asp Lys Asp Tyr Phe
            325                 330                 335
Tyr Thr His Thr Ala Cys Asp Ala Asn Gly Glu Thr Gln Leu Met Tyr
        340                 345                 350
Lys Trp Ala Lys Pro Lys Ile Cys Ser Glu Asp Leu Glu Gly Ala Val
    355                 360                 365
Lys Leu Pro Ala Ser Gly Val Lys Thr His Cys Pro Pro Cys Asn Pro
370                 375                 380
Gly Phe Phe Lys Thr Asn Asn Ser Thr Cys Gln Pro Cys Pro Tyr Gly
385                 390                 395                 400
Ser Tyr Ser Asn Gly Ser Asp Cys Thr Arg Cys Pro Ala Gly Thr Glu
            405                 410                 415
Pro Ala Val Gly Phe Glu Tyr Lys Trp Trp Asn Thr Leu Pro Thr Asn
        420                 425                 430
Met Glu Thr Thr Val Leu Ser Gly Ile Asn Phe Glu Tyr Lys Gly Met
    435                 440                 445
Thr Gly Trp Glu Val Ala Gly Asp His Ile Tyr Thr Ala Ala Gly Ala
450                 455                 460
Ser Asp Asn Asp Phe Met Ile Leu Thr Leu Val Val Pro Gly Phe Arg
465                 470                 475                 480
Pro Pro Gln Ser Val Met Ala Asp Thr Glu Asn Lys Glu Val Ala Arg
            485                 490                 495
Ile Thr Phe Val Phe Glu Thr Leu Cys Ser Val Asn Cys Glu Leu Tyr
        500                 505                 510
Phe Met Val Gly Val Asn Ser Arg Thr Asn Thr Pro Val Glu Thr Trp
    515                 520                 525
Lys Gly Ser Lys Gly Lys Gln Ser Tyr Thr Tyr Ile Ile Glu Glu Asn
530                 535                 540
Thr Thr Thr Ser Phe Thr Trp Ala Phe Gln Arg Thr Thr Phe His Glu
545                 550                 555                 560
Ala Ser Arg Lys Tyr Thr Asn Asp Val Ala Lys Ile Tyr Ser Ile Asn
            565                 570                 575
Val Thr Asn Val Met Asn Gly Val Ala Ser Tyr Cys Arg Pro Cys Ala
        580                 585                 590
Leu Glu Ala Ser Asp Val Gly Ser Ser Cys Thr Ser Cys Pro Ala Gly
    595                 600                 605
Tyr Tyr Ile Asp Arg Asp Ser Gly Thr Cys His Ser Cys Pro Thr Asn
610                 615                 620
Thr Ile Leu Lys Ala His Gln Pro Tyr Gly Val Gln Ala Cys Val Pro
625                 630                 635                 640
Cys Gly Pro Gly Thr Lys Asn Asn Lys Ile His Ser Leu Cys Tyr Asn
            645                 650                 655
Asp Cys Thr Phe Ser Arg Asn Thr Pro Thr Arg Thr Phe Asn Tyr Asn
        660                 665                 670
Phe Ser Ala Leu Ala Asn Thr Val Thr Leu Ala Gly Gly Pro Ser Phe
    675                 680                 685
Thr Ser Lys Gly Leu Lys Tyr Phe His His Phe Thr Leu Ser Leu Cys
690                 695                 700
Gly Asn Gln Gly Arg Lys Met Ser Val Cys Thr Asp Asn Val Thr Asp
705                 710                 715                 720
Leu Arg Ile Pro Glu Gly Glu Ser Gly Phe Ser Lys Ser Ile Thr Ala
            725                 730                 735
```

-continued

```
Tyr Val Cys Gln Ala Val Ile Ile Pro Pro Glu Val Thr Gly Tyr Lys
                740                 745                 750
Ala Gly Val Ser Ser Gln Pro Val Ser Leu Ala Asp Arg Leu Ile Gly
            755                 760                 765
Val Thr Thr Asp Met Thr Leu Asp Gly Ile Thr Ser Pro Ala Glu Leu
770                 775                 780
Phe His Leu Glu Ser Leu Gly Ile Pro Asp Val Ile Phe Phe Tyr Arg
785                 790                 795                 800
Ser Asn Asp Val Thr Gln Ser Cys Ser Ser Gly Arg Ser Thr Thr Ile
                805                 810                 815
Arg Val Arg Cys Ser Pro Gln Lys Thr Val Pro Gly Ser Leu Leu Leu
            820                 825                 830
Pro Gly Thr Cys Ser Asp Gly Thr Cys Asp Gly Cys Asn Phe His Phe
        835                 840                 845
Leu Trp Glu Ser Ala Ala Ala Cys Pro Leu Cys Ser Val Ala Asp Tyr
    850                 855                 860
His Ala Ile Val Ser Ser Cys Val Ala Gly Ile Gln Lys Thr Thr Tyr
865                 870                 875                 880
Val Trp Arg Glu Pro Lys Leu Cys Ser Gly Ile Ser Leu Pro Glu
                885                 890                 895
Gln Arg Val Thr Ile Cys Lys Thr Ile Asp Phe Trp Leu Lys Val Gly
            900                 905                 910
Ile Ser Ala Gly Thr Cys Thr Ala Ile Leu Leu Thr Val Leu Thr Cys
        915                 920                 925
Tyr Phe Trp Lys Lys Asn Gln Lys Leu Glu Tyr Lys Tyr Ser Lys Leu
    930                 935                 940
Val Met Asn Ala Thr Leu Lys Asp Cys Asp Leu Pro Ala Ala Asp Ser
945                 950                 955                 960
Cys Ala Ile Met Glu Gly Glu Asp Val Glu Asp Asp Leu Ile Phe Thr
                965                 970                 975
Ser Lys Lys Ser Leu Phe Gly Lys Ile Lys Ser Phe Thr Ser Lys Arg
            980                 985                 990
Thr Pro Asp Gly Phe Asp Ser Val Pro Leu Lys Thr Ser Ser Gly Gly
        995                 1000                1005
Leu Asp Met Asp Leu
    1010

<210> SEQ ID NO 5
<211> LENGTH: 580
<212> TYPE: PRT
<213> ORGANISM: Homo sapiens

<400> SEQUENCE: 5

Trp Trp Asn Thr Leu Pro Thr Asn Met Glu Thr Thr Val Leu Ser Gly
1               5                   10                  15
Ile Asn Phe Glu Tyr Lys Gly Met Thr Gly Trp Glu Val Ala Gly Asp
                20                  25                  30
His Ile Tyr Thr Ala Ala Gly Ala Ser Asp Asn Asp Phe Met Ile Leu
            35                  40                  45
Thr Leu Val Val Pro Gly Phe Arg Pro Pro Gln Ser Val Met Ala Asp
        50                  55                  60
Thr Glu Asn Lys Glu Val Ala Arg Ile Thr Phe Val Phe Glu Thr Leu
65                  70                  75                  80
Cys Ser Val Asn Cys Glu Leu Tyr Phe Met Val Gly Val Asn Ser Arg
                85                  90                  95
```

-continued

Thr Asn Thr Pro Val Glu Thr Trp Lys Gly Ser Lys Gly Lys Gln Ser
            100                 105                 110

Tyr Thr Tyr Ile Ile Glu Glu Asn Thr Thr Thr Ser Phe Thr Trp Ala
            115                 120                 125

Phe Gln Arg Thr Thr Phe His Glu Ala Ser Arg Lys Tyr Thr Asn Asp
            130                 135                 140

Val Ala Lys Ile Tyr Ser Ile Asn Val Thr Asn Val Met Asn Gly Val
145                 150                 155                 160

Ala Ser Tyr Cys Arg Pro Cys Ala Leu Glu Ala Ser Asp Val Gly Ser
                165                 170                 175

Ser Cys Thr Ser Cys Pro Ala Gly Tyr Tyr Ile Asp Arg Asp Ser Gly
            180                 185                 190

Thr Cys His Ser Cys Pro Asn Thr Ile Leu Lys Ala His Gln Pro
            195                 200                 205

Tyr Gly Val Gln Ala Cys Val Pro Cys Gly Pro Gly Thr Lys Asn Asn
    210                 215                 220

Lys Ile His Ser Leu Cys Tyr Asn Asp Cys Thr Phe Ser Arg Asn Thr
225                 230                 235                 240

Pro Thr Arg Thr Phe Asn Tyr Asn Phe Ser Ala Leu Ala Asn Thr Val
                245                 250                 255

Thr Leu Ala Gly Gly Pro Ser Phe Thr Ser Lys Gly Leu Lys Tyr Phe
            260                 265                 270

His His Phe Thr Leu Ser Leu Cys Gly Asn Gln Gly Arg Lys Met Ser
    275                 280                 285

Val Cys Thr Asp Asn Val Thr Asp Leu Arg Ile Pro Glu Gly Glu Ser
    290                 295                 300

Gly Phe Ser Lys Ser Ile Thr Ala Tyr Val Cys Gln Ala Val Ile Ile
305                 310                 315                 320

Pro Pro Glu Val Thr Gly Tyr Lys Ala Gly Val Ser Ser Gln Pro Val
                325                 330                 335

Ser Leu Ala Asp Arg Leu Ile Gly Val Thr Thr Asp Met Thr Leu Asp
            340                 345                 350

Gly Ile Thr Ser Pro Ala Glu Leu Phe His Leu Glu Ser Leu Gly Ile
    355                 360                 365

Pro Asp Val Ile Phe Phe Tyr Arg Ser Asn Asp Val Thr Gln Ser Cys
    370                 375                 380

Ser Ser Gly Arg Ser Thr Thr Ile Arg Val Arg Cys Ser Pro Gln Lys
385                 390                 395                 400

Thr Val Pro Gly Ser Leu Leu Leu Pro Gly Thr Cys Ser Asp Gly Thr
                405                 410                 415

Cys Asp Gly Cys Asn Phe His Phe Leu Trp Glu Ser Ala Ala Ala Cys
            420                 425                 430

Pro Leu Cys Ser Val Ala Asp Tyr His Ala Ile Val Ser Ser Cys Val
            435                 440                 445

Ala Gly Ile Gln Lys Thr Thr Tyr Val Trp Arg Glu Pro Lys Leu Cys
    450                 455                 460

Ser Gly Gly Ile Ser Leu Pro Glu Gln Arg Val Thr Ile Cys Lys Thr
465                 470                 475                 480

Ile Asp Phe Trp Leu Lys Val Gly Ile Ser Ala Gly Thr Cys Thr Ala
                485                 490                 495

Ile Leu Leu Thr Val Leu Thr Cys Tyr Phe Trp Lys Lys Asn Gln Lys
            500                 505                 510

Leu Glu Tyr Lys Tyr Ser Lys Leu Val Met Asn Ala Thr Leu Lys Asp

```
                    515                 520                 525
Cys Asp Leu Pro Ala Ala Asp Ser Cys Ala Ile Met Glu Gly Glu Asp
            530                 535                 540

Val Glu Asp Asp Leu Ile Phe Thr Ser Lys Lys Ser Leu Phe Gly Lys
545                 550                 555                 560

Ile Lys Ser Phe Thr Ser Lys Gln Pro Ala Pro Val Thr Ile Ser Leu
                565                 570                 575

Ser Glu Asp Ser
            580

<210> SEQ ID NO 6
<211> LENGTH: 1002
<212> TYPE: PRT
<213> ORGANISM: Homo sapiens

<400> SEQUENCE: 6

Met Ala Glu Pro Gly His Ser His His Leu Ser Ala Arg Val Arg Gly
  1               5                  10                  15

Arg Thr Glu Arg Arg Ile Pro Arg Leu Trp Arg Leu Leu Trp Ala
                 20                  25                  30

Gly Thr Ala Phe Gln Val Thr Gln Gly Thr Gly Pro Glu Leu His Ala
             35                  40                  45

Cys Lys Glu Ser Glu Tyr His Tyr Glu Tyr Thr Ala Cys Asp Ser Thr
         50                  55                  60

Gly Ser Arg Trp Arg Val Ala Val Pro His Thr Pro Gly Leu Cys Thr
 65                  70                  75                  80

Ser Leu Pro Asp Pro Val Lys Gly Thr Glu Cys Ser Phe Ser Cys Asn
                 85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Val Gln Asn
        195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
    290                 295                 300

Glu Thr Ser Cys His Gln Cys Asp Pro Asp Lys Tyr Ser Glu Lys Gly
```

```
                305                 310                 315                 320
Ser Ser Ser Cys Asn Val Arg Pro Ala Cys Thr Asp Lys Asp Tyr Phe
                    325                 330                 335

Tyr Thr His Thr Ala Cys Asp Ala Asn Gly Glu Thr Gln Leu Met Tyr
                    340                 345                 350

Lys Trp Ala Lys Pro Lys Ile Cys Ser Glu Asp Leu Glu Gly Ala Val
                    355                 360                 365

Lys Leu Pro Ala Ser Gly Val Lys Thr His Cys Pro Pro Cys Asn Pro
            370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                    405                 410                 415

Pro Ala Val Gly Phe Glu Tyr Lys Trp Trp Asn Thr Leu Pro Thr Asn
                    420                 425                 430

Met Glu Thr Thr Val Leu Ser Gly Ile Asn Phe Glu Tyr Lys Gly Met
            435                 440                 445

Thr Gly Trp Glu Val Ala Gly Asp His Ile Tyr Thr Ala Ala Gly Ala
    450                 455                 460

Ser Asp Asn Asp Phe Met Ile Leu Thr Leu Val Val Pro Gly Phe Arg
465                 470                 475                 480

Pro Pro Gln Ser Val Met Ala Asp Thr Glu Asn Lys Glu Val Ala Arg
                    485                 490                 495

Ile Thr Phe Val Phe Glu Thr Leu Cys Ser Val Asn Cys Glu Leu Tyr
                    500                 505                 510

Phe Met Val Gly Val Asn Ser Arg Thr Asn Thr Pro Val Glu Thr Trp
            515                 520                 525

Lys Gly Ser Lys Gly Lys Gln Ser Tyr Thr Tyr Ile Ile Glu Glu Asn
            530                 535                 540

Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
                    565                 570                 575

Val Thr Asn Val Met Asn Gly Val Ala Ser Tyr Cys Arg Pro Cys Ala
            580                 585                 590

Leu Glu Ala Ser Asp Val Gly Ser Cys Thr Ser Cys Pro Ala Gly
            595                 600                 605

Tyr Tyr Ile Asp Arg Asp Ser Gly Thr Cys His Ser Cys Pro Pro Asn
            610                 615                 620

Thr Ile Leu Lys Ala His Gln Pro Tyr Gly Val Gln Ala Cys Val Pro
625                 630                 635                 640

Cys Gly Pro Gly Thr Lys Asn Asn Lys Ile His Ser Leu Cys Tyr Asn
                    645                 650                 655

Asp Cys Thr Phe Ser Arg Asn Thr Pro Thr Arg Thr Phe Asn Tyr Asn
                    660                 665                 670

Phe Ser Ala Leu Ala Asn Thr Val Thr Leu Ala Gly Gly Pro Ser Phe
            675                 680                 685

Thr Ser Lys Gly Leu Lys Tyr Phe His His Phe Thr Leu Ser Leu Cys
            690                 695                 700

Gly Asn Gln Gly Arg Lys Met Ser Val Cys Thr Asp Asn Val Thr Asp
705                 710                 715                 720

Leu Arg Ile Pro Glu Gly Glu Ser Gly Phe Ser Lys Ser Ile Thr Ala
                    725                 730                 735
```

```
Tyr Val Cys Gln Ala Val Ile Ile Pro Pro Glu Val Thr Gly Tyr Lys
                740                 745                 750

Ala Gly Val Ser Ser Gln Pro Val Ser Leu Ala Asp Arg Leu Ile Gly
            755                 760                 765

Val Thr Thr Asp Met Thr Leu Asp Gly Ile Thr Ser Pro Ala Glu Leu
770                 775                 780

Phe His Leu Glu Ser Leu Gly Ile Pro Asp Val Ile Phe Phe Tyr Arg
785                 790                 795                 800

Ser Asn Asp Val Thr Gln Ser Cys Ser Ser Gly Arg Ser Thr Thr Ile
                805                 810                 815

Arg Val Arg Cys Ser Pro Gln Lys Thr Val Pro Gly Ser Leu Leu Leu
                820                 825                 830

Pro Gly Thr Cys Ser Asp Gly Thr Cys Asp Gly Cys Asn Phe His Phe
            835                 840                 845

Leu Trp Glu Ser Ala Ala Cys Pro Leu Cys Ser Val Ala Asp Tyr
            850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
                900                 905                 910

Ile Ser Ala Gly Thr Cys Thr Ala Ile Leu Leu Thr Val Leu Thr Cys
                915                 920                 925

Tyr Phe Trp Lys Lys Asn Gln Lys Leu Glu Tyr Lys Tyr Ser Lys Leu
            930                 935                 940

Val Met Asn Ala Thr Leu Lys Asp Cys Asp Leu Pro Ala Ala Asp Ser
945                 950                 955                 960

Cys Ala Ile Met Glu Gly Glu Asp Val Glu Asp Leu Ile Phe Thr
                965                 970                 975

Ser Lys Lys Ser Leu Phe Gly Lys Ile Lys Ser Phe Thr Ser Lys Val
            980                 985                 990

Ser Gly Ser Ser Pro Leu Gly Ala Glu Ser
            995                 1000

<210> SEQ ID NO 7
<211> LENGTH: 1004
<212> TYPE: PRT
<213> ORGANISM: Homo sapiens

<400> SEQUENCE: 7

Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
                20                  25                  30

Gly Thr Ala Phe Gln Val Thr Gln Gly Thr Gly Pro Glu Leu His Ala
            35                  40                  45

Cys Lys Glu Ser Glu Tyr His Tyr Glu Tyr Thr Ala Cys Asp Ser Thr
        50                  55                  60

Gly Ser Arg Trp Arg Val Ala Val Pro His Thr Pro Gly Leu Cys Thr
65                  70                  75                  80

Ser Leu Pro Asp Pro Val Lys Gly Thr Glu Cys Ser Phe Ser Cys Asn
                85                  90                  95

Ala Gly Glu Phe Leu Asp Met Lys Asp Gln Ser Cys Lys Pro Cys Ala
                100                 105                 110
```

-continued

Glu Gly Arg Tyr Ser Leu Gly Thr Gly Ile Arg Phe Asp Glu Trp Asp
            115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ile Ile Phe Glu Phe Val Gln Asn
        195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
    290                 295                 300

Glu Thr Ser Cys His Gln Cys Asp Pro Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
            340                 345                 350

Lys Trp Ala Lys Pro Lys Ile Cys Ser Glu Asp Leu Glu Gly Ala Val
        355                 360                 365

Lys Leu Pro Ala Ser Gly Val Lys Thr His Cys Pro Pro Cys Asn Pro
    370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                405                 410                 415

Pro Ala Val Gly Phe Glu Tyr Lys Trp Trp Asn Thr Leu Pro Thr Asn
            420                 425                 430

Met Glu Thr Thr Val Leu Ser Gly Ile Asn Phe Glu Tyr Lys Gly Met
        435                 440                 445

Thr Gly Trp Glu Val Ala Gly Asp His Ile Tyr Thr Ala Ala Gly Ala
    450                 455                 460

Ser Asp Asn Asp Phe Met Ile Leu Thr Leu Val Val Pro Gly Phe Arg
465                 470                 475                 480

Pro Pro Gln Ser Val Met Ala Asp Thr Glu Asn Lys Glu Val Ala Arg
                485                 490                 495

Ile Thr Phe Val Phe Glu Thr Leu Cys Ser Val Asn Cys Glu Leu Tyr
            500                 505                 510

Phe Met Val Gly Val Asn Ser Arg Thr Asn Thr Pro Val Glu Thr Trp
        515                 520                 525

Lys Gly Ser Lys Gly Lys Gln Ser Tyr Thr Tyr Ile Ile Glu Glu Asn
    530                 535                 540

```
Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
                565                 570                 575

Val Thr Asn Val Met Asn Gly Val Ala Ser Tyr Cys Arg Pro Cys Ala
            580                 585                 590

Leu Glu Ala Ser Asp Val Gly Ser Ser Cys Thr Ser Cys Pro Ala Gly
        595                 600                 605

Tyr Tyr Ile Asp Arg Asp Ser Gly Thr Cys His Ser Cys Pro Pro Asn
    610                 615                 620

Thr Ile Leu Lys Ala His Gln Pro Tyr Gly Val Gln Ala Cys Val Pro
625                 630                 635                 640

Cys Gly Pro Gly Thr Lys Asn Asn Lys Ile His Ser Leu Cys Tyr Asn
                645                 650                 655

Asp Cys Thr Phe Ser Arg Asn Thr Pro Thr Arg Thr Phe Asn Tyr Asn
            660                 665                 670

Phe Ser Ala Leu Ala Asn Thr Val Thr Leu Ala Gly Pro Ser Phe
        675                 680                 685

Thr Ser Lys Gly Leu Lys Tyr Phe His His Phe Thr Leu Ser Leu Cys
    690                 695                 700

Gly Asn Gln Gly Arg Lys Met Ser Val Cys Thr Asp Asn Val Thr Asp
705                 710                 715                 720

Leu Arg Ile Pro Glu Gly Ser Gly Phe Ser Lys Ser Ile Thr Ala
                725                 730                 735

Tyr Val Cys Gln Ala Val Ile Ile Pro Pro Glu Val Thr Gly Tyr Lys
            740                 745                 750

Ala Gly Val Ser Ser Gln Pro Val Ser Leu Ala Asp Arg Leu Ile Gly
        755                 760                 765

Val Thr Thr Asp Met Thr Leu Asp Gly Ile Thr Ser Pro Ala Glu Leu
    770                 775                 780

Phe His Leu Glu Ser Leu Gly Ile Pro Asp Val Ile Phe Phe Tyr Arg
785                 790                 795                 800

Ser Asn Asp Val Thr Gln Ser Cys Ser Ser Gly Arg Ser Thr Thr Ile
                805                 810                 815

Arg Val Arg Cys Ser Pro Gln Lys Thr Val Pro Gly Ser Leu Leu Leu
            820                 825                 830

Pro Gly Thr Cys Ser Asp Gly Thr Cys Asp Gly Cys Asn Phe His Phe
        835                 840                 845

Leu Trp Glu Ser Ala Ala Ala Cys Pro Leu Cys Ser Val Ala Asp Tyr
    850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
            900                 905                 910

Ile Ser Ala Gly Thr Cys Thr Ala Ile Leu Thr Val Leu Thr Cys
        915                 920                 925

Tyr Phe Trp Lys Lys Asn Gln Lys Leu Glu Tyr Lys Tyr Ser Lys Leu
    930                 935                 940

Val Met Asn Ala Thr Leu Lys Asp Cys Asp Leu Pro Ala Ala Asp Ser
945                 950                 955                 960

Cys Ala Ile Met Glu Gly Glu Asp Val Glu Asp Asp Leu Ile Phe Thr
```

```
                965                 970                 975
Ser Lys Lys Ser Leu Phe Gly Lys Ile Lys Ser Phe Thr Ser Lys Gln
            980                 985                 990
Pro Ala Pro Val Thr Ile Ser Leu Ser Glu Asp Ser
            995                 1000
```

<210> SEQ ID NO 8
<211> LENGTH: 5940
<212> TYPE: DNA
<213> ORGANISM: Homo sapiens

<400> SEQUENCE: 8

| | | | | | |
|---|---|---|---|---|---|
| aaaaaaccag | gattaggaga | gagagaatga | aggagggtgg | tgccactatt | ttagaagggt | 60 |
| agggatgtcc | tctcaggagg | tgacatttga | gcagagacct | gaaggagatg | agggaggagc | 120 |
| cgtggagctt | tccaggcagc | agacacagca | ggagaggagg | cggcagctgg | gccagacaca | 180 |
| actcatgtac | aaatgggcca | agccgaaaat | ctgtagcgag | gaccttgagg | gggcagtgaa | 240 |
| gctgcctgcc | tctggtgtga | agacccactg | cccacccttgc | aacccaggct | tcttcaaaac | 300 |
| caacaacagc | acctgccagc | cctgcccata | tggttcctac | tccaatggct | cagactgtac | 360 |
| ccgctgccct | gcagggactg | aacctgctgt | gggatttgaa | tacaaatggt | ggaacacgct | 420 |
| gcccacaaac | atgaaaacga | ccgttctcag | tgggatcaac | ttcgagtaca | agggcatgac | 480 |
| aggctgggag | gtggctggtg | atcacattta | cacagctgct | ggagcctcag | acaatgactt | 540 |
| catgattctc | actctggttg | tgccaggatt | tagacctccg | cagtcggtga | tggcagacac | 600 |
| agagaataaa | gaggtggcca | gaatcacatt | tgtctttgag | accctctgtt | ctgtgaactg | 660 |
| tgagctctac | ttcatggtgg | gtgtgaattc | taggaccaac | actcctgtgg | agacgtggaa | 720 |
| aggttccaaa | ggcaaacagt | cctataccta | catcattgag | gagaacacta | ccacgagctt | 780 |
| cacctgggcc | ttccagagga | ccacttttca | tgaggcaagc | aggaagtaca | ccaatgacgt | 840 |
| tgccaagatc | tactccatca | atgtcaccaa | tgttatgaat | ggcgtggcct | cctactgccg | 900 |
| tccctgtgcc | ctagaagcct | ctgatgtggg | ctcctcctgc | acctcttgtc | ctgctggtta | 960 |
| ctatattgac | cgagattcag | gaacctgcca | ctcctgcccc | cctaacacaa | ttctgaaagc | 1020 |
| ccaccagcct | tatggtgtcc | aggcctgtgt | gccctgtggt | ccagggacca | agaacaacaa | 1080 |
| gatccactct | ctgtgctaca | atgattgcac | cttctcacgc | aacactccaa | ccaggacttt | 1140 |
| caactacaac | ttctccgctt | tggcaaacac | cgtcactctt | gctggagggc | caagcttcac | 1200 |
| ttccaaaggg | ttgaaatact | tccatcactt | taccctcagt | ctctgtggaa | accagggtag | 1260 |
| gaaaatgtct | gtgtgcaccg | acaatgtcac | tgacctccgg | attcctgagg | gtgagtcagg | 1320 |
| gttctccaaa | tctatcacag | cctacgtctg | ccaggcagtc | atcatccccc | cagaggtgac | 1380 |
| aggctacaag | gccggggttt | cctcacagcc | tgtcagcctt | gctgatcgac | ttattggggt | 1440 |
| gacaacagat | atgactctgg | atggaatcac | ctccccagct | gaactttttcc | acctggagtc | 1500 |
| cttgggaata | ccggacgtga | tcttcttta | taggtccaat | gatgtgaccc | agtcctgcag | 1560 |
| ttctggagga | tcaaccacca | tccgcgtcag | gtgcagtcca | cagaaaactg | tccctggaag | 1620 |
| tttgctgctg | ccaggaacgt | gctcagatgg | gacctgtgat | ggctgcaact | tccacttcct | 1680 |
| gtgggagagc | gcggctgctt | gccgctctg | ctcagtggct | gactaccatg | ctatcgtcag | 1740 |
| cagctgtgtg | gctgggatcc | agaagactac | ttacgtgtgg | cgagaaccca | agctatgctc | 1800 |
| tggtggcatt | tctctgcctg | agcagagagt | caccatctgc | aaaaccatag | atttctggct | 1860 |
| gaaagtgggc | atctctgcag | gcacctgtac | tgccatcctg | ctcaccgtct | tgacctgcta | 1920 |

```
cttttggaaa aagaatcaaa aactagagta caagtactcc aagctggtga tgaatgctac   1980
tctcaaggac tgtgacctgc cagcagctga cagctgcgcc atcatggaag gcgaggatgt   2040
agaggacgac ctcatctttα ccagcaagaa gtcactcttt gggaagatca aatcatttac   2100
ctccaagagg actcctgatg gatttgactc agtgccgctg aagacatcct caggaggccc   2160
agacatggac ctgtgagagg cactgcctgc ctcacctgcc tcctcacctt gcatagcacc   2220
tttgcaagcc tgcggcgatt tgggtgccag catcctgcaa cacccactgc tggaaatctc   2280
ttcattgtgg ccttatcaga tgtttgaatt tcagatcttt ttttatagag tacccaaacc   2340
ctcctttctg cttgcctcaa acctgccaaa tatacccaca cttgttgt aaattatgcc      2400 cttgcttgta tcttgtttcc caaaatggcc catccgccag agccatagct tcgtctgctc   2460
ataattctta tagctttgga atgaaaatat ttctatcttc ttaagtatag aaactatttc   2520
ctctgtcctc taacttaagg gcagaaacag ctgggagttt tcctcgcatg ccctcagctc   2580
atgatctctt caggagagag gctgggtgag gagggtgtcg gggttccctg gtggataatc   2640
ttcatagcag cctggatcca tttcccctgg ataaccagct caaagggagt gaaaatggta   2700
gtctgagggc aaggggagca aggcctgggt aagaaaagcc ttgaaaagca taaaagagg     2760 ccgggcgcgg tggctcacgc ctgtaatccc agcactttgg gaggccgagg cgggcagatc   2820
atgaggtcgg gagattgaga ccatcctggc taacacggtg aaaccccgtc tctactaaaa   2880
atacaaaaaa ttagccgggc gtggtggcgg gtgcctgtag tcccagctac tcgggaggct   2940
gaggcgggag aatagcgtga acctggaagg cggagcttgc agtgagccga gatcgcgcca   3000
ctgcactcca tccagcctgg gtgacagagt gagactctgc ctcaaaaaaa aaaaaaaaa    3060 agaaaagcac aaagagaggc aacaaggaat gttttgttt ttgagacagg ctctcactct    3120
gtcacctagg ctggagtgca gtggcataat cactgttcag tgcagcctca agctcttggg   3180
ctcaagctat cctcccatct caacctctca gtagctagg actacaagtg tgcaccacca    3240
ggctcactaa tttttatatt ttttgtagac acagggtttc accatgttgc ccaggctggt   3300
ctccaactcc tgggctcaag tgatctgtcc gcctcagcct cccaaactgc tgggattaca   3360
ggcataagcc actgcactca gccttttatt tgttttttaa accacgtagc tcattgcctt   3420
ctcttaagta aatgatagat attctcactg aagccaaagg aataagttca tcaagaaaat   3480
gcccaaagcc ctggtggata catcctccct atctttttt taaaccttcc actatcactc    3540
tatgacactg aaaagaacca ggtaagcccc aaacccagat gttccagcct tatcctctat   3600
tgggtttacc cacagacata gcaaaccctg tcagtgagga aaattcccca tccttgagtg   3660
cccccgtcct agaagtttgg gccatattat ggaacagggg tctcttattt gaaaagagca   3720
caaggaggcc aagattttaa tggggcactt tagggggatac agcccacaat ggcatggcc   3780 tgaggtggcc gtgatgtctg cttctaagct taacgcatct gctcaggcac agaataaacg   3840
tctaggctgg ccaaaaaagg aactgaatcc caggcccata cgccagcacc agaatcaaac   3900
cagtcttcaa ggaaggaagg ctaggagagt ttaacaagat tttcactggg cccagcatgg   3960
tggctcacac ctgtaatccc aaggcagaat ggtggcttga gctcaggagt tcaagaccag   4020
cctgggcaac acagtgagac cctgtctcta aaaaatttaa aaataaacaa ggtgttcacc   4080
aagctgggat acttctcact attaagcccc tatcttctc ttttttttcat tctcaattgc    4140 tttgtgtgat aaaaaactaa agagacttct ggtccaattt ctggcaacat cccttctgaa   4200
aggtgagtag agtgggtgtc ttctatgccc attttcccca attttacaca aactattatc   4260
aatgaacttt taagtaccta gaatgggtaa aaccagagca agactttaaa ttaccttctt   4320
```

| | | | | |
|---|---|---|---|---|
| ctttcttcta | ctggcagttc | tgcctccatc | actatcaggc | tagggtgacc ttcccttggt | 4380 |
| caagccccaa | ttgcccatga | tttgtgcctg | tgcccttct | ccagtgacca tttggtgacc | 4440 |
| agatggtaga | tatagaaagg | ggatggcatt | tgcaagtgac | tagtctgcca caaaatgctc | 4500 |
| atctgattag | ccactgctgc | cctggcaatg | gctttgtaag | agtcaatgag aactagagcc | 4560 |
| aggctgtggt | ccctggccat | caacagtgtt | ggtgacggca | gggagtccct ttggtttaat | 4620 |
| aaatccagtt | tttctttggg | tatccaaatt | ctccctcct | tttgtaggag tcaggctctc | 4680 |
| agaacctgtg | tccatgttgg | aacttccccc | agtgtggatg | cagatacgca gctcctgagc | 4740 |
| tccagcctaa | agtcttctgt | agcctcagca | atacttgggc | acctgctgtc tcactgaata | 4800 |
| gctttctttt | gtgacaaagg | ccacagacag | cccttagact | attccggaaa cagtaggaaa | 4860 |
| aattacatat | gtctttgact | tctttattct | gactccactg | attttagcca taatacttta | 4920 |
| aggagctact | ttttactacc | ccttaccgtg | ctgacttctg | caggtctgcc ctgtgacctg | 4980 |
| tcaggaactc | ctgagttacg | ctactggggt | cacctgttgc | tcccctagca agttaggcat | 5040 |
| gtcatatatt | tttaacagct | ttattgagat | ataattcaca | tattatacaa ttcacccttta | 5100 |
| aaacatacga | ttcaatggtt | ttcagcaaac | tcacagagtt | gtccgcccac ttgagagcaa | 5160 |
| acacatgttc | aattttcttt | tccttttttt | ttttgagaca | gagtcagctt tgtcgcccag | 5220 |
| gctggagtgc | agtgccatga | tcttggctca | ctgcagcctc | cccatcctgg gttcaagtga | 5280 |
| tccttctgct | tcagcctccc | cagtagctgg | gattacaagc | atgcgccacc acgcctagct | 5340 |
| aatttttgtg | tttttagtag | agatggggtt | tcaccatgtt | ggccaggctg gtctcaaact | 5400 |
| cctggactca | agtgatccac | ccacctcggc | ctcccaaagt | gctgggatta caggtgtaag | 5460 |
| ccaccgtgcc | tggcctacgt | gttcaatttt | ctatgaacaa | aggctttagt ccttgaccca | 5520 |
| gggctaaagt | ggtctgtcca | agctgttgtt | ggtagaggga | gtatgataaa atgtttaaat | 5580 |
| ctcatttggt | taccttgagt | cctggaacat | gcagtaactg | tcatgctata gtcatcatct | 5640 |
| gtatttggct | gggaatacaa | atgaagattg | tggtgtattc | aagcagtagg gttttgctt | 5700 |
| ttgtttttgt | tttagtgcca | acaaaacttt | tttttgtctg | actacattaa agataagact | 5760 |
| gactatattt | atacaacaga | aactttgtaa | tagatttttt | cagctttgtg aaatcgaatt | 5820 |
| ttttttcatc | agggctggtt | ggatttcctt | tttaccctgt | aatccaagcg ttaatagttt | 5880 |
| gttagaagat | gggttattgc | atgtcacttt | tttttttgt | aaaataaaaa catacctac | 5940 |

<210> SEQ ID NO 9
<211> LENGTH: 6944
<212> TYPE: DNA
<213> ORGANISM: Homo sapiens

<400> SEQUENCE: 9

| | | | | |
|---|---|---|---|---|
| acccgcaggt | gagctgcaga | ggcgcgcgtg | gtccctgccc | cacccgcgcg gagccagaga | 60 |
| ggaggcggtt | gtcaaggcga | cgtggaagca | gcagccgcag | cacctgagcc gctactgccg | 120 |
| ctcactcagg | acaacgctat | ggctgagcct | gggcacagcc | accatctctc cgccagagtc | 180 |
| agggggaagaa | ctgagaggcg | catacccgg | ctgtggcggc | tgctgctctg ggctgggacc | 240 |
| gccttccagg | tgacccaggg | aacgggaccg | gagcttcatg | cctgcaaaga gtctgagtac | 300 |
| cactatgagt | acacgcgtg | tgacagcacg | ggttccaggt | ggagggtcgc cgtgccgcat | 360 |
| accccgggcc | tgtgcaccag | cctgcctgac | cccgtcaagg | gcaccgagtg ctccttctcc | 420 |
| tgcaacgccg | gggagtttct | ggatatgaag | gaccagtcat | gtaagccatg cgctgagggc | 480 |
| cgctactccc | tcggcacagg | cattcggttt | gatgagtggg | atgagctgcc ccatggcttt | 540 |

```
gccagcctct cagccaacat ggagctggat gacagtgctg ctgagtccac cgggaactgt    600
acttcgtcca agtgggttcc ccggggcgac tacatcgcct ccaacacgga cgaatgcaca    660
gccacactga tgtacgccgt caacctgaag caatctggca ccgttaactt cgaatactac    720
tatccagact ccagcatcat ctttgagttt ttcgttcaga atgaccagtg ccagcccaat    780
gcagatgact ccaggtggat gaagaccaca gagaaaggat gggaattcca cagtgtggag    840
ctaaatcgag gcaataatgt cctctattgg agaaccacag ccttctcagt atggaccaaa    900
gtacccaagc ctgtgctggt gagaaacatt gccataacag gggtggccta cacttcagaa    960
tgcttcccct gcaaacctgg cacgtatgca gacaagcagg gctcctcttt ctgcaaactt   1020
tgcccagcca actcttattc aaataaagga gaaacttctt gccaccagtg tgaccctgac   1080
aaatactcag agaaaggatc ttcttcctgt aacgtgcgcc cagcttgcac agacaaagat   1140
tatttctaca cacacggc ctgcgatgcc aacggagaga cacaactcat gtacaaatgg   1200
gccaagccga aaatctgtag cgaggacctt gaggggcag tgaagctgcc tgcctctggt   1260
gtgaagaccc actgcccacc ctgcaaccca ggcttcttca aaaccaacaa cagcacctgc   1320
cagccctgcc catatggttc ctactccaat ggctcagact gtaccgctg ccctgcaggg   1380 actgaacctg ctgtgggatt tgaatacaaa tggtggaaca cgctgcccac aaacatggaa   1440
acgaccgttc tcagtgggat caacttcgag tacaagggca tgacaggctg ggaggtggct   1500
ggtgatcaca tttacacagc tgctggagcc tcagacaatg acttcatgat tctcactctg   1560
gttgtgccag gatttagacc tccgcagtcg gtgatggcag acacagagaa taaagaggtg   1620
gccagaatca catttgtctt tgagaccctc tgttctgtga actgtgagct ctacttcatg   1680
gtgggtgtga attctaggac caacactcct gtggagacgt ggaaaggttc caaaggcaaa   1740
cagtcctata cctacatcat tgaggagaac actaccacga gcttcacctg ggccttccag   1800
aggaccactt ttcatgaggc aagcaggaag tacaccaatg acgttgccaa gatctactcc   1860
atcaatgtca ccaatgttat gaatggcgtg gcctcctact gccgtccctg tgccctagaa   1920
gcctctgatg tgggctcctc ctgcacctct tgtcctgctg ttactatat tgaccgagat   1980 tcaggaacct gccactcctg cccccctaac acaattctga agcccacca gccttatggt   2040 gtccaggcct gtgtgccctg tggtccaggg accaagaaca caagatcca ctctctgtgc   2100 tacaatgatt gcaccttctc acgcaacact ccaaccagga cttcaacta caacttctcc   2160 gctttggcaa acaccgtcac tcttgctgga gggccaagct tcacttccaa agggttgaaa   2220
tacttccatc actttacccct cagtctctgt ggaaaccagg gtaggaaaat gtctgtgtgc   2280
accgacaatg tcactgacct ccggattcct gagggtgagt cagggttctc caaatctatc   2340
acagcctacg tctgccaggc agtcatcatc ccccagagg tgacaggcta caaggccggg   2400
gtttcctcac agcctgtcag ccttgctgat cgacttattg gggtgacaac agatatgact   2460
ctggatggaa tcacctcccc agctgaactt ttccacctgg agtccttggg aataccggac   2520
gtgatcttct tttataggtc caatgatgtg acccagtcct gcagttctgg gagatcaacc   2580
accatccgcg tcaggtgcag tccacagaaa actgtccctg aagtttgct gctgccagga   2640 acgtgctcag atgggacctg tgatggctgc aacttccact tcctgtggga gagcgcggct   2700
gcttgcccgc tctgctcagt ggctgactac catgctatcg tcagcagctg tgtggctggg   2760
atccagaaga ctacttacgt gtggcgagaa cccaagctat gctctggtgg catttctctg   2820
cctgagcaga gagtcaccat ctgcaaaacc atagatttct ggctgaaagt gggcatctct   2880
gcaggcacct gtactgccat cctgctcacc gtcttgacct gctactttg gaaaaagaat   2940
```

```
caaaaactag agtacaagta ctccaagctg gtgatgaatg ctactctcaa ggactgtgac    3000
ctgccagcag ctgacagctg cgccatcatg gaaggcgagg atgtagagga cgacctcatc    3060
tttaccagca agaagtcact ctttgggaag atcaaatcat ttacctccaa gaggactcct    3120
gatggatttg actcagtgcc gctgaagaca tcctcaggag gcccagacat ggacctgtga    3180
gaggcactgc ctgcctcacc tgcctcctca ccttgcatag cacctttgca agcctgcggc    3240
gatttgggtg ccagcatcct gcaacaccca ctgctgaaaa tctcttcatt gtggccttat    3300
cagatgtttg aatttcagat cttttttttat agagtaccca aaccctcctt tctgcttgcc    3360
tcaaacctgc caaatatacc cacactttgt ttgtaaatta tgcccttgct tgtatcttgt    3420
ttcccaaaat ggcccatccg ccagagccat agcttcgtct gctcataatt cttatagctt    3480
tggaatgaaa atatttctat cttcttaagt atagaaacta tttcctctgt cctctaactt    3540
aagggcagaa acagctggga gttttcctcg catgccctca gctcatgatc tcttcaggag    3600
agaggctggg tgaggagggt gtcggggttc cctggtggat aatcttcata gcagcctgga    3660
tccatttccc ctggataacc agctcaaagg gagtgaaaat ggtagtctga gggcaagggg    3720
agcaaggcct gggtaagaaa agccttgaaa agcataaaaa gaggccgggc gcggtggctc    3780
acgcctgtaa tcccagcact ttgggaggcc gaggcgggca gatcatgagg tcgggagatt    3840
gagaccatcc tggctaacac ggtgaaaccc cgtctctact aaaaatacaa aaaattagcc    3900
gggcgtggtg gcgggtgcct gtagtcccag ctactcggga ggctgaggcg ggagaatagc    3960
gtgaacctgg aaggcggagc ttgcagtgag ccgagatcgc gccactgcac tccatccagc    4020
ctgggtgaca gagtgagact ctgcctcaaa aaaaaaaaaa aaaagaaaa gcacaaagag    4080
aggcaacaag gaatgttttt gttttttgaga caggctctca ctctgtcacc taggctggag    4140
tgcagtggca taatcactgt tcagtgcagc ctcaagctct gggctcaag ctatcctccc    4200
atctcaacct ctcaagtagc taggactaca agtgtgcacc accaggctca ctaatttta    4260
tatttttgt agacacaggg tttcaccatg ttgcccaggc tggtctccaa ctcctgggct    4320
caagtgatct gtccgcctca gcctcccaaa ctgctgggat tacaggcata agccactgca    4380
ctcagccttt tatttgtttt ttaaaccacg tagctcattg ccttctctta agtaaatgat    4440
agatattctc actgaagcca aaggaataag ttcatcaaga aaatgcccaa agccctggtg    4500
gatacatcct cccctatcttt tttttaaacc ttccactatc actctatgac actgaaaaga    4560
accaggtaag ccccaaaccc agatgttcca gccttatcct ctattgggtt tacccacaga    4620
catagcaaac cctgtcagtg aggaaaattc cccatccttg agtgccccg tcctagaagt    4680
ttgggccata ttatggaaca ggggtctctt atttgaaaag agcacaagga ggccaagatt    4740
ttaatgggc actttagggg atacagccca caatggcatg gcctgaggt ggccgtgatg    4800
tctgcttcta agcttaacgc atctgctcag gcacagaata aacgtctagg ctggccaaaa    4860
aaggaactga atcccaggcc catacgccag caccagaatc aaaccagtct tcaaggaagg    4920
aaggctagga gagtttaaca agattttcac tgggcccagc atggtggctc acacctgtaa    4980
tcccaaggca gaatggtggc ttgagctcag gagttcaaga ccagcctggg caacacagtg    5040
agaccctgtc tctaaaaaat ttaaaaataa acaaggtgtt caccaagctg ggatacttct    5100
cactattaag cccctatctt tctctttttt tcattctcaa ttgctttgtg tgataaaaaa    5160
ctaaagagac ttctggtcca atttctggca acatcccttc tgaaaggtga gtagagtggg    5220
tgtcttctat gcccattttc cccaattttta cacaaactat tatcaatgaa cttttaagta    5280
cctagaatgg gtaaaaccag agcaagactt taaattacct tcttcttcttct tctactggca    5340
```

-continued

```
gttctgcctc catcactatc aggctagggt gaccttccct tggtcaagcc ccaattgccc      5400
atgatttgtg cctgtgccct ttctccagtg accatttggt gaccagatgg tagatataga      5460
aaggggatgg catttgcaag tgactagtct gccacaaaat gctcatctga ttagccactg      5520
ctgccctggc aatggctttg taagagtcaa tgagaactag agccaggctg tggtccctgg      5580
ccatcaacag tgttggtgac ggcagggagt ccctttggtt taataaatcc agttttctt       5640 tgggtatcca aattctcccc tccttttgta ggagtcaggc tctcagaacc tgtgtccatg      5700
ttggaacttc ccccagtgtg gatgcagata cgcagctcct gagctccagc ctaaagtctt      5760
ctgtagcctc agcaatactt gggcacctgc tgtctcactg aatagctttc ttttgtgaca      5820
aaggccacag acagccctta gactattccg gaaacagtag gaaaaattac atatgtcttt      5880
gacttcttta ttctgactcc actgatttta gccataatac tttaaggagc tactttttac      5940 tacccttac cgtgctgact tctgcaggtc tgccctgtga cctgtcagga actcctgagt       6000
tacgctactg gggtcacctg ttgctcccct agcaagttag gcatgtcata tatttttaac     6060
agctttattg agatataatt cacatattat acaattcacc tttaaaacat acgattcaat      6120
ggttttcagc aaactcacag agttgtccgc ccacttgaga gcaaacacat gttcaatttt      6180
cttttccttt ttttttttga cacagagtca gctttgtcgc ccaggctgga gtgcagtgcc      6240
atgatcttgg ctcactgcag cctccccatc ctgggttcaa gtgatccttc tgcttcagcc      6300
tccccagtag ctgggattac aagcatgcgc caccacgcct agctaatttt tgtgttttta      6360
gtagagatgg ggtttcacca tgttggccag gctggtctca aactcctgga ctcaagtgat      6420
ccacccacct cggcctccca aagtgctggg attacaggtg taagccaccg tgcctggcct      6480
acgtgttcaa ttttctatga acaaaggctt tagtccttga cccagggcta aagtggtctg      6540
tccaagctgt tgttggtaga gggagtatga taaaatgttt aaatctcatt tggttacctt      6600
gagtcctgga acatgcagta actgtcatgc tatagtcatc atctgtattt ggctgggaat      6660
acaaatgaag attgtggtgt attcaagcag tagggttttt gcttttgttt ttgttttagt      6720
gccaacaaaa cttttttttg tctgactaca ttaaagataa gactgactat atttatacaa      6780
cagaaacttt gtaatagatt ttttcagctt tgtgaaatcg aatttttttt catcagggct      6840
ggttggattt ccttttacc ctgtaatcca agcgttaata gtttgttaga agatgggtta       6900
ttgcatgtca cttttttttt ttgtaaaata aaacatacc ttac                       6944
```

<210> SEQ ID NO 10
<211> LENGTH: 6944
<212> TYPE: DNA
<213> ORGANISM: Homo sapiens

<400> SEQUENCE: 10

```
acccgcaggt gagctgcaga ggcgcgcgtg gtccctgccc cacccgcgcg gagccagaga        60
ggaggcggtt gtcaaggcga cgtggaagca gcagccgcag cacctgagcc gctactgccg       120
ctcactcagg acaacgctat ggctgagcct gggcacagcc accatctctc cgccagagtc       180
aggggaagaa ctgagaggcg catacccggg ctgtggcggc tgctgctctg ggctgggacc       240
gccttccagg tgacccaggg aacgggaccg gagcttcatg cctgcaaaga gtctgagtac       300
cactatgagt acacggcgtg tgacagcacg ggttccaggt ggagggtcgc cgtgccgcat       360
accccgggcc tgtgcaccag cctgcctgac cccgtcaagg gcaccgagtg ctccttctcc       420
tgcaacgccg gggagtttct ggatatgaag gaccagtcat gtaagccatg cgctgagggc       480
cgctactccc tcggcacagg cattcggttt gatgagtggg atgagctgcc ccatggcttt      540
```

```
gccagcctct cagccaacat ggagctggat gacagtgctg ctgagtccac cgggaactgt    600
acttcgtcca agtgggttcc ccggggcgac tacatcgcct ccaacacgga cgaatgcaca    660
gccacactga tgtacgccgt caacctgaag caatctggca ccgttaactt cgaatactac    720
tatccagact ccagcatcat ctttgagttt ttcgttcaga atgaccagtg ccagcccaat    780
gcagatgact ccaggtggat gaagaccaca gagaaaggat gggaattcca cagtgtggag    840
ctaaatcgag gcaataatgt cctctattgg agaaccacag ccttctcagt atggaccaaa    900
gtacccaagc ctgtgctggt gagaaacatt gccataacag gggtggccta cacttcagaa    960
tgcttcccct gcaaacctgg cacgtatgca gacaagcagg gctcctcttt ctgcaaactt   1020
tgcccagcca actcttattc aaataaagga gaaacttctt gccaccagtg tgaccctgac   1080
aaatactcag agaaaggatc ttcttcctgt aacgtgcgcc cagcttgcac agacaaagat   1140
tatttctaca cacacacggc ctgcgatgcc aacggagaga cacaactcat gtacaaatgg   1200
gccaagccga aaatctgtag cgaggacctt gaggggcag tgaagctgcc tgcctctggt   1260
gtgaagaccc actgcccacc ctgcaaccca ggcttcttca aaaccaacaa cagcacctgc   1320
cagccctgcc catatggttc ctactccaat ggctcagact gtaccgctg ccctgcaggg   1380
actgaacctg ctgtgggatt tgaatacaaa tggtggaaca cgctgcccac aaacatggaa   1440
acgaccgttc tcagtgggat caacttcgag tacaagggca tgacaggctg ggaggtggct   1500
ggtgatcaca tttacacagc tgctggagcc tcagacaatg acttcatgat tctcactctg   1560
gttgtgccag gatttagacc tccgcagtcg gtgatggcag acacagagaa taaagaggtg   1620
gccagaatca catttgtctt tgagaccctc tgttctgtga actgtgagct ctacttcatg   1680
gtgggtgtga attctaggac caacactcct gtggagacgt ggaaaggttc caaaggcaaa   1740
cagtcctata cctacatcat tgaggagaac actaccacga gcttcacctg ggccttccag   1800
aggaccactt ttcatgaggc aagcaggaag tacaccaatg acgttgccaa gatctactcc   1860
atcaatgtca ccaatgttat gaatggcgtg gcctcctact gccgtccctg tgccctagaa   1920
gcctctgatg tgggctcctc ctgcacctct tgtcctgctg ttactatat tgaccgagat   1980
tcaggaacct gccactcctg cccccctaac acaattctga agcccacca gccttatggt   2040
gtccaggcct gtgtgccctg tggtccaggg accaagaaca caagatcca ctctctgtgc   2100
tacaatgatt gcaccttctc acgcaacact ccaaccagga cttttcaacta aacttctcc   2160
gctttggcaa acaccgtcac tcttgctgga gggccaagct tcacttccaa agggttgaaa   2220
tacttccatc actttaccct cagtctctgt ggaaaccagg gtaggaaaat gtctgtgtgc   2280
accgacaatg tcactgacct ccggattcct gagggtgagt cagggttctc caaatctatc   2340
acagcctacg tctgccaggc agtcatcatc ccccagagg tgacaggcta caaggccggg   2400
gtttcctcac agcctgtcag ccttgctgat cgacttattg gggtgacaac agatatgact   2460
ctggatggaa tcacctcccc agctgaactt ttccacctgg agtccttggg aataccggac   2520
gtgatcttct tttataggtc caatgatgtg acccagtcct gcagttctgg gagatcaacc   2580
accatccgcg tcaggtgcag tccacagaaa actgtccctg gaagtttgct gctgccagga   2640
acgtgctcag atgggacctg tgatggctgc aacttccact tcctgtggga gagcgcggct   2700
gcttgcccgc tctgctcagt ggctgactac catgctatcg tcagcagctg tgtggctggg   2760
atccagaaga ctacttacgt gtggcgagaa cccaagctat gctctggtgg catttctctg   2820
cctgagcaga gagtcaccat ctgcaaaacc atagatttct ggctgaaagt gggcatctct   2880
gcaggcacct gtactgccat cctgctcacc gtcttgacct gctacttttg gaaaagaat   2940
```

```
caaaaactag agtacaagta ctccaagctg gtgatgaatg ctactctcaa ggactgtgac      3000
ctgccagcag ctgacagctg cgccatcatg gaaggcgagg atgtagagga cgacctcatc      3060
tttaccagca agaagtcact ctttgggaag atcaaatcat ttacctccaa gaggactcct      3120
gatggatttg actcagtgcc gctgaagaca tcctcaggag gcccagacat ggacctgtga      3180
gaggcactgc ctgcctcacc tgcctcctca ccttgcatag caccttttgca agcctgcggc      3240 gatttgggtg ccagcatcct gcaacaccca ctgctggaaa tctcttcatt gtggccttat      3300
cagatgtttg aatttcagat cttttttttat agagtaccca aaccctcctt tctgcttgcc      3360
tcaaacctgc caaatatacc cacactttgt ttgtaaatta tgcccttgct tgtatcttgt      3420
ttcccaaaat ggcccatccg ccagagccat agcttcgtct gctcataatt cttatagctt      3480
tggaatgaaa atatttctat cttcttaagt atagaaacta tttcctctgt cctctaactt      3540
aagggcagaa acagctggga gttttcctcg catgccctca gctcatgatc tcttcaggag      3600
agaggctggg tgaggagggt gtcggggttc cctggtggat aatcttcata gcagcctgga      3660
tccatttccc ctggataacc agctcaaagg gagtgaaaat ggtagtctga gggcaagggg      3720
agcaaggcct gggtaagaaa agccttgaaa agcataaaaa gaggccgggc gcggtggctc      3780
acgcctgtaa tcccagcact ttgggaggcc gaggcgggca gatcatgagg tcgggagatt      3840
gagaccatcc tggctaacac ggtgaaaccc cgtctctact aaaaatacaa aaaattagcc      3900
gggcgtggtg gcgggtgcct gtagtcccag ctactcggga ggctgaggcg ggagaatagc      3960
gtgaacctgg aaggcggagc ttgcagtgag ccgagatcgc gccactgcac tccatccagc      4020
ctgggtgaca gagtgagact ctgcctcaaa aaaaaaaaaa aaaagaaaa gcacaaagag      4080 aggcaacaag gaatgttttt gttttttgaga caggctctca ctctgtcacc taggctggag      4140
tgcagtggca taatcactgt tcagtgcagc ctcaagctct gggctcaag ctatcctccc       4200 atctcaacct ctcaagtagc taggactaca agtgtgcacc accaggctca ctaattttta      4260 tatttttttgt agacacaggg tttcaccatg ttgcccaggc tggtctccaa ctcctgggct      4320
caagtgatct gtccgcctca gcctcccaaa ctgctgggat tacaggcata agccactgca      4380
ctcagccttt tatttgtttt ttaaaccacg tagctcattg ccttctctta agtaaatgat      4440
agatattctc actgaagcca aaggaataag ttcatcaaga aaatgcccaa agccctggtg      4500
gatacatcct ccctatcttt tttttaaacc ttccactatc actctatgac actgaaagaa      4560
accaggtaag ccccaaaccc agatgttcca gccttatcct ctattgggtt tacccacaga      4620
catagcaaac cctgtcagtg aggaaaattc cccatccttg agtgccccg tcctagaagt       4680 ttgggccata ttatggaaca ggggtctctt atttgaaaag agcacaagga ggccaagatt      4740 ttaatgggc acttttagggg atacagccca caatggcatg gcctgaggt ggccgtgatg       4800 tctgcttcta agcttaacgc atctgctcag gcacagaata aacgtctagg ctggccaaaa      4860
aaggaactga atcccaggcc catacgccag caccagaatc aaaccagtct tcaaggaagg      4920
aaggctagga gagtttaaca agattttcac tgggcccagc atggtggctc acacctgtaa      4980
tcccaaggca gaatggtggc ttgagctcag gagttcaaga ccagcctggg caacacagtg      5040
agaccctgtc tctaaaaaat ttaaaaataa acaaggtgtt caccaagctg ggatacttct      5100
cactattaag cccctatctt tctcttttttt tcattctcaa ttgctttgtg tgataaaaaa      5160
ctaaagagac ttctggtcca atttctggca acatcccttc tgaaaggtga gtagagtggg      5220
tgtcttctat gcccatttc cccaatttta cacaaactat tatcaatgaa cttttaagta       5280
cctagaatgg gtaaaaccag agcaagactt taaattacct tcttcttttct tctactggca      5340
```

-continued

| | |
|---|---|
| gttctgcctc catcactatc aggctagggt gaccttccct tggtcaagcc ccaattgccc | 5400 |
| atgatttgtg cctgtgccct ttctccagtg accatttggt gaccagatgg tagatataga | 5460 |
| aaggggatgg catttgcaag tgactagtct gccacaaaat gctcatctga ttagccactg | 5520 |
| ctgcccctggc aatggctttg taagagtcaa tgagaactag agccaggctg tggtccctgg | 5580 |
| ccatcaacag tgttggtgac ggcagggagt ccctttggtt taataaatcc agttttttctt | 5640 |
| tgggtatcca aattctcccc tccttttgta ggagtcaggc tctcagaacc tgtgtccatg | 5700 |
| ttggaacttc ccccagtgtg gatgcagata cgcagctcct gagctccagc ctaaagtctt | 5760 |
| ctgtagcctc agcaatactt gggcacctgc tgtctcactg aatagctttc ttttgtgaca | 5820 |
| aaggccacag acagcccctta gactattccg gaaacagtag gaaaaattac atatgtcttt | 5880 |
| gacttcttta ttctgactcc actgatttta gccataatac tttaaggagc tacttttttac | 5940 |
| taccccttac cgtgctgact tctgcaggtc tgccctgtga cctgtcagga actcctgagt | 6000 |
| tacgctactg gggtcacctg ttgctcccct agcaagttag gcatgtcata tattttttaac | 6060 |
| agctttattg agatataatt cacatattat acaattcacc tttaaaacat acgattcaat | 6120 |
| ggttttcagc aaactcacag agttgtccgc ccacttgaga gcaaacacat gttcaatttt | 6180 |
| cttttccttt tttttttttga gacagagtca gctttgtcgc ccaggctgga gtgcagtgcc | 6240 |
| atgatcttgg ctcactgcag cctccccatc ctgggttcaa gtgatccttc tgcttcagcc | 6300 |
| tccccagtag ctgggattac aagcatgcgc caccacgcct agctaatttt tgtgttttta | 6360 |
| gtagagatgg ggtttcacca tgttggccag gctggtctca aactcctgga ctcaagtgat | 6420 |
| ccacccacct cggcctccca aagtgctggg attacaggtg taagccaccg tgcctggcct | 6480 |
| acgtgttcaa ttttctatga acaaaggctt tagtccttga cccagggcta aagtggtctg | 6540 |
| tccaagctgt tgttggtaga gggagtatga taaaatgttt aaatctcatt tggttaccttt | 6600 |
| gagtcctgga acatgcagta actgtcatgc tatagtcatc atctgtattt ggctgggaat | 6660 |
| acaaatgaag attgtggtgt attcaagcag tagggttttt gcttttgttt ttgttttagt | 6720 |
| gccaacaaaa ctttttttttg tctgactaca ttaaagataa gactgactat atttatacaa | 6780 |
| cagaaacttt gtaatagatt ttttcagctt tgtgaaatcg aatttttttt catcagggct | 6840 |
| ggttggatttt cctttttacc ctgtaatcca agcgttaata gtttgttaga agatgggtta | 6900 |
| ttgcatgtca cttttttttt ttgtaaaata aaacatacc ttac | 6944 |

<210> SEQ ID NO 11
<211> LENGTH: 6944
<212> TYPE: DNA
<213> ORGANISM: Homo sapiens

<400> SEQUENCE: 11

| | |
|---|---|
| acccgcaggt gagctgcaga ggcgcgcgtg gtccctgccc cacccgcgcg gagccagaga | 60 |
| ggaggcggtt gtcaaggcga cgtggaagca gcagccgcag cacctgagcc gctactgccg | 120 |
| ctcactcagg acaacgctat ggctgagcct gggcacagcc accatctctc cgccagagtc | 180 |
| aggggaagaa ctgagaggcg catacccccgg ctgtggcggc tgctgctctg ggctgggacc | 240 |
| gccttccagg tgacccaggg aacgggaccg gagcttcatg cctgcaaaga gtctgagtac | 300 |
| cactatgagt acacggcgtg tgacagcacg ggttccaggt ggagggtcgc cgtgccgcat | 360 |
| accccgggcc tgtgcaccag cctgcctgac cccgtcaagg gcaccgagtg ctccttctcc | 420 |
| tgcaacgccg gggagtttct ggatatgaag gaccagtcat gtaagccatg cgctgagggc | 480 |
| cgctactccc tcggcacagg cattcggttt gatgagtggg atgagctgcc ccatggcttt | 540 |

```
gccagcctct cagccaacat ggagctggat gacagtgctg ctgagtccac cgggaactgt    600
acttcgtcca agtgggttcc ccggggcgac tacatcgcct ccaacacgga cgaatgcaca    660
gccacactga tgtacgccgt caacctgaag caatctggca ccgttaactt cgaatactac    720
tatccagact ccagcatcat ctttgagttt ttcgttcaga atgaccagtg ccagcccaat    780
gcagatgact ccaggtggat gaagaccaca gagaaaggat gggaattcca cagtgtggag    840
ctaaatcgag gcaataatgt cctctattgg agaaccacag ccttctcagt atggaccaaa    900
gtacccaagc ctgtgctggt gagaaacatt gccataacag gggtggccta cacttcagaa    960
tgcttcccct gcaaacctgg cacgtatgca gacaagcagg gctcctcttt ctgcaaactt   1020
tgcccagcca actcttattc aaataaagga gaaacttctt gccaccagtg tgaccctgac   1080
aaatactcag agaaaggatc ttcttcctgt aacgtgcgcc cagcttgcac agacaaagat   1140
tatttctaca cacacggc ctgcgatgcc aacggagaga cacaactcat gtacaaatgg   1200
gccaagccga aaatctgtag cgaggacctt gaggggcag tgaagctgcc tgcctctggt   1260
gtgaagaccc actgcccacc ctgcaaccca ggcttcttca aaaccaacaa cagcacctgc   1320
cagccctgcc catatggttc ctactccaat ggctcagact gtaccgctg ccctgcaggg   1380
actgaacctg ctgtgggatt tgaatacaaa tggtggaaca cgctgcccac aaacatggaa   1440
acgaccgttc tcagtgggat caacttcgag tacaagggca tgacaggctg ggaggtggct   1500
ggtgatcaca tttacacagc tgctggagcc tcagacaatg acttcatgat tctcactctg   1560
gttgtgccag gatttagacc tccgcagtcg gtgatggcag acacagagaa taaagaggtg   1620
gccagaatca catttgtctt tgagaccctc tgttctgtga actgtgagct ctacttcatg   1680
gtgggtgtga attctaggac caacactcct gtggagacgt ggaaaggttc caaaggcaaa   1740
cagtcctata cctacatcat tgaggagaac actaccacga gcttcacctg ggccttccag   1800
aggaccactt ttcatgaggc aagcaggaag tacaccaatg acgttgccaa gatctactcc   1860
atcaatgtca ccaatgttat gaatggcgtg gcctcctact gccgtccctg tgccctagaa   1920
gcctctgatg tgggctcctc ctgcacctct tgtcctgctg ttactatat tgaccgagat   1980
tcaggaacct gccactcctg ccccccctaac acaattctga agcccaccca gccttatggt   2040
gtccaggcct gtgtgccctg tggtccaggg accaagaaca caagatcca ctctctgtgc   2100
tacaatgatt gcaccttctc acgcaacact ccaaccagga cttttcaacta caacttctcc   2160
gctttggcaa acaccgtcac tcttgctgga gggccaagct tcacttccaa agggttgaaa   2220
tacttccatc actttacccct cagtctctgt ggaaaccagg gtaggaaaat gtctgtgtgc   2280
accgacaatg tcactgacct ccggattcct gagggtgagt cagggttctc caaatctatc   2340
acagcctacg tctgccaggc agtcatcatc cccccagagg tgacaggcta caaggccggg   2400
gtttcctcac agcctgtcag ccttgctgat cgacttattg gggtgacaac agatatgact   2460
ctggatggaa tcacctcccc agctgaactt ttccacctgg agtccttggg aataccggac   2520
gtgatcttct tttataggtc caatgatgtg acccagtcct gcagttctgg gagatcaacc   2580
accatccgcg tcaggtgcag tccacagaaa actgtccctg aagtttgct gctgccagga   2640
acgtgctcag atgggacctg tgatggctgc aacttccact tcctgtggga gagcgcggct   2700
gcttgcccgc tctgctcagt ggctgactac catgctatcg tcagcagctg tgtggctggg   2760
atccagaaga ctacttacgt gtggcgagaa cccaagctat gctctggtgg catttctctg   2820
cctgagcaga gagtcaccat ctgcaaaacc atagatttct ggctgaaagt gggcatctct   2880
gcaggcacct gtactgccat cctgctcacc gtcttgacct gctactttg gaaaaagaat   2940
```

```
caaaaactag agtacaagta ctccaagctg gtgatgaatg ctactctcaa ggactgtgac    3000
ctgccagcag ctgacagctg cgccatcatg gaaggcgagg atgtagagga cgacctcatc    3060
tttaccagca agaagtcact ctttgggaag atcaaatcat ttacctccaa gaggactcct    3120
gatggatttg actcagtgcc gctgaagaca tcctcaggag gcccagacat ggacctgtga    3180
gaggcactgc ctgcctcacc tgcctcctca ccttgcatag cacctttgca agcctgcggc    3240
gatttgggtg ccagcatcct gcaacaccca ctgctggaaa tctcttcatt gtggccttat    3300
cagatgtttg aatttcagat cttttttttat agagtaccca aaccctcctt tctgcttgcc    3360
tcaaacctgc caaatatacc cacactttgt ttgtaaatta tgcccttgct tgtatcttgt    3420
ttcccaaaat ggcccatccg ccagagccat agcttcgtct gctcataatt cttatagctt    3480
tggaatgaaa atatttctat cttcttaagt atagaaacta tttcctctgt cctctaactt    3540
aagggcagaa acagctggga gttttcctcg catgccctca gctcatgatc tcttcaggag    3600
agaggctggg tgaggagggt gtcggggttc cctggtggat aatcttcata gcagcctgga    3660
tccatttccc ctggataacc agctcaaagg gagtgaaaat ggtagtctga gggcaagggg    3720
agcaaggcct gggtaagaaa agccttgaaa agcataaaaa gaggccgggc gcggtggctc    3780
acgcctgtaa tcccagcact ttgggaggcc gaggcgggca gatcatgagg tcgggagatt    3840
gagaccatcc tggctaacac ggtgaaaccc cgtctctact aaaaatacaa aaaattagcc    3900
gggcgtggtg gcgggtgcct gtagtcccag ctactcggga ggctgaggcg ggagaatagc    3960
gtgaacctgg aaggcggagc ttgcagtgag ccgagatcgc gccactgcac tccatccagc    4020
ctgggtgaca gagtgagact ctgcctcaaa aaaaaaaaaa aaaagaaaa gcacaaagag    4080 aggcaacaag gaatgttttt gttttttgaga caggctctca ctctgtcacc taggctggag    4140
tgcagtggca taatcactgt tcagtgcagc ctcaagctct gggctcaag ctatcctccc    4200 atctcaaccct ctcaagtagc taggactaca agtgtgcacc accaggctca ctaattttta    4260
tattttttgt agacacaggg tttcaccatg ttgcccaggc tggtctccaa ctcctgggct    4320
caagtgatct gtccgcctca gcctcccaaa ctgctgggat tacaggcata agccactgca    4380
ctcagccttt tatttgtttt ttaaaccacg tagctcattg ccttctctta agtaaatgat    4440
agatattctc actgaagcca aaggaataag ttcatcaaga aaatgcccaa agccctggtg    4500
gatacatcct cccctatcttt ttttaaacc ttccactatc actctatgac actgaaaaga    4560
accaggtaag ccccaaaccc agatgttcca gccttatcct ctattgggtt tacccacaga    4620
catagcaaac cctgtcagtg aggaaaattc cccatccttg agtgccccg tcctagaagt    4680 ttgggccata ttatggaaca ggggtctctt atttgaaaag agcacaagga ggccaagatt    4740
ttaatggggc actttagggg atacagccca caatggcatg ggcctgaggt ggccgtgatg    4800
tctgcttcta agcttaacgc atctgctcag gcacagaata aacgtctagg ctggccaaaa    4860
aaggaactga atcccaggcc catacgccag caccagaatc aaaccagtct tcaaggaagg    4920
aaggctagga gagtttaaca agattttcac tgggcccagc atggtggctc acacctgtaa    4980
tcccaaggca gaatggtggc ttgagctcag gagttcaaga ccagcctggg caacacagtg    5040
agaccctgtc tctaaaaaat ttaaaaataa acaaggtgtt caccaagctg ggatacttct    5100
cactattaag cccctatctt tctcttttt tcattctcaa ttgctttgtg tgataaaaaa    5160
ctaaagagac ttctggtcca atttctggca acatcccttc tgaaaggtga gtagagtggg    5220
tgtcttctat gcccatttc cccaatttta cacaaactat tatcaatgaa cttttaagta    5280
cctagaatgg gtaaaaccag agcaagactt taaattacct tcttctttct tctactggca    5340
```

-continued

```
gttctgcctc catcactatc aggctagggt gaccttccct tggtcaagcc ccaattgccc    5400
atgatttgtg cctgtgccct ttctccagtg accatttggt gaccagatgg tagatataga    5460
aaggggatgg catttgcaag tgactagtct gccacaaaat gctcatctga ttagccactg    5520
ctgccctggc aatggctttg taagagtcaa tgagaactag agccaggctg tggtccctgg    5580
ccatcaacag tgttggtgac ggcagggagt ccctttggtt taataaatcc agttttctt    5640 tgggtatcca aattctcccc tccttttgta ggagtcaggc tctcagaacc tgtgtccatg    5700
ttggaacttc ccccagtgtg gatgcagata cgcagctcct gagctccagc ctaaagtctt    5760
ctgtagcctc agcaatactt gggcacctgc tgtctcactg aatagctttc ttttgtgaca    5820
aaggccacag acagcccta gactattccg gaaacagtag gaaaaattac atatgtcttt    5880
gacttcttta ttctgactcc actgatttta gccataatac tttaaggagc tactttttac    5940
taccccttac cgtgctgact tctgcaggtc tgccctgtga cctgtcagga actcctgagt    6000
tacgctactg gggtcacctg ttgctcccct agcaagttag gcatgtcata tattttaac    6060 agctttattg agatataatt cacatattat acaattcacc tttaaaacat acgattcaat    6120
ggttttcagc aaactcacag agttgtccgc ccacttgaga gcaaacacat gttcaatttt    6180
cttttccttt ttttttttga cacagagtca gctttgtcgc ccaggctgga gtgcagtgcc    6240
atgatcttgg ctcactgcag cctccccatc ctgggttcaa gtgatccttc tgcttcagcc    6300
tccccagtag ctgggattac aagcatgcgc caccacgcct agctaatttt tgtgttttta    6360
gtagagatgg ggtttcacca tgttggccag gctggtctca aactcctgga ctcaagtgat    6420
ccacccacct cggcctccca aagtgctggg attacaggtg taagccaccg tgcctggcct    6480
acgtgttcaa ttttctatga acaaaggctt tagtccttga cccagggcta aagtggtctg    6540
tccaagctgt tgttggtaga gggagtatga taaaatgttt aaatctcatt tggttacctt    6600
gagtcctgga acatgcagta actgtcatgc tatagtcatc atctgtattt ggctgggaat    6660
acaaatgaag attgtggtgt attcaagcag tagggttttt gcttttgttt ttgttttagt    6720
gccaacaaaa cttttttttg tctgactaca ttaaagataa gactgactat atttatacaa    6780
cagaaacttt gtaatagatt ttttcagctt tgtgaaatcg aattttttt catcagggct    6840 ggttggattt cctttttacc ctgtaatcca agcgttaata gtttgttaga agatgggtta    6900
ttgcatgtca cttttttttt ttgtaaaata aaacatacc ttac                      6944
```

<210> SEQ ID NO 12
<211> LENGTH: 7044
<212> TYPE: DNA
<213> ORGANISM: Homo sapiens

<400> SEQUENCE: 12

```
tgtcaaggcg acgtgggtag gaggagagga cagagggagg aggaaggatg ggcggtgttg      60
gcgtagccgc agggaggtga ctgaagcgag cctggcctct tgcatcctcc gcctgtgtac     120
ctccctcccc ttttttttccg ccttctgcca gcagaagcag cagccgcagc acctgagccg    180
ctactgccgc tcactcagga caacgctatg gctgagcctg gcacagcca ccatctctcc      240 gccagagtca ggggaagaac tgagaggcgc ataccccggc tgtggcggct gctgctctgg    300
gctgggaccg ccttccaggt gacccaggga acgggaccgg agcttcatgc ctgcaaagag    360
tctgagtacc actatgagta cacggcgtgt gacagcacgg gttccaggtg gagggtcgcc    420
gtgccgcata ccccgggcct gtgcaccagc ctgcctgacc ccgtcaaggg caccgagtgc    480
tccttctcct gcaacgccgg ggagtttctg gatatgaagg accagtcatg taagccatgc    540
```

```
gctgagggcc gctactccct cggcacaggc attcggtttg atgagtggga tgagctgccc     600
catggctttg ccagcctctc agccaacatg gagctggatg acagtgctgc tgagtccacc     660
gggaactgta cttcgtccaa gtgggttccc cggggcgact acatcgcctc caacacggac     720
gaatgcacag ccacactgat gtacgccgtc aacctgaagc aatctggcac cgttaacttc     780
gaatactact atccagactc cagcatcatc tttgagtttt tcgttcagaa tgaccagtgc     840
cagcccaatg cagatgactc caggtggatg aagaccacag agaaaggatg ggaattccac     900
agtgtggagc taaatcgagg caataatgtc ctctattgga gaaccacagc cttctcagta     960
tggaccaaag tacccaagcc tgtgctggtg agaaacattg ccataacagg ggtggcctac    1020
acttcagaat gcttcccctg caaacctggc acgtatgcag acaagcaggg ctcctctttc    1080
tgcaaacttt gcccagccaa ctcttattca aataaaggag aaacttcttg ccaccagtgt    1140
gaccctgaca atactcaga gaaaggatct tcttcctgta acgtgcgccc agcttgcaca     1200
gacaaagatt atttctacac acacgggcc tgcgatgcca acggagagac acaactcatg     1260
tacaaatggg ccaagccgaa aatctgtagc gaggaccttg agggggcagt gaagctgcct    1320
gcctctggtg tgaagaccca ctgcccaccc tgcaacccag gcttcttcaa aaccaacaac    1380
agcacctgcc agccctgccc atatggttcc tactccaatg gctcagactg tacccgctgc    1440
cctgcaggga ctgaacctgc tgtgggattt gaatacaaat ggtggaacac gctgcccaca    1500
aacatggaaa cgaccgttct cagtgggatc aacttcgagt acaagggcat gacaggctgg    1560
gaggtggctg gtgatcacat ttacacagct gctggagcct cagacaatga cttcatgatt    1620
ctcactctgg ttgtgccagg atttagacct ccgcagtcgg tgatggcaga cacagagaat    1680
aaagaggtgg ccagaatcac atttgtcttt gagaccctct gttctgtgaa ctgtgagctc    1740
tacttcatgg tgggtgtgaa ttctaggacc aacactcctg tggagacgtg gaaaggttcc    1800
aaaggcaaac agtcctatac ctacatcatt gaggagaaca ctaccacgag cttcacctgg    1860
gccttccaga ggaccacttt tcatgaggca agcaggaagt acaccaatga cgttgccaag    1920
atctactcca tcaatgtcac caatgttatg aatggcgtgg cctcctactg ccgtccctgt    1980
gccctagaag cctctgatgt gggctcctcc tgcacctctt gtcctgctgg ttactatatt    2040
gaccgagatt caggaacctg ccactcctgc cccctaaca caattctgaa agcccaccag    2100
ccttatggtg tccaggcctg tgtgccctgt ggtccaggga ccaagaacaa caagatccac    2160
tctctgtgct acaatgattg caccttctca cgcaacactc caaccaggac tttcaactac    2220
aacttctccg ctttggcaaa caccgtcact cttgctggag gccaagctt cacttccaaa    2280
gggttgaaat acttccatca ctttacccct agtctctgtg aaaccaggg taggaaaatg    2340
tctgtgtgca ccgacaatgt cactgacctc cggattcctg agggtgagtc agggttctcc    2400
aaatctatca cagcctacgt ctgccaggca gtcatcatcc ccccagaggt gacaggctac    2460
aaggccgggg tttcctcaca gcctgtcagc cttgctgatc gacttattgg ggtgacaaca    2520
gatatgactc tggatggaat caccctcccca gctgaacttt tccacctgga gtccttggga    2580
ataccggacg tgatcttctt ttataggtcc aatgatgtga cccagtcctg cagttctggg    2640
agatcaacca ccatccgcgt caggtgcagt ccacagaaaa ctgtccctgg aagtttgctg    2700
ctgccaggaa cgtgctcaga tgggacctgt gatggctgca acttccactt cctgtgggag    2760
agcgcggctg cttgcccgct ctgctcagtg gctgactacc atgctatcgt cagcagctgt    2820
gtggctggga tccagaagac tacttacgtg tggcgagaac ccaagctatg ctctggtggc    2880
atttctctgc ctgagcagag agtcaccatc tgcaaaacca tagatttctg gctgaaagtg    2940
```

```
ggcatctctg caggcacctg tactgccatc ctgctcaccg tcttgacctg ctacttttgg    3000
aaaaagaatc aaaaactaga gtacaagtac tccaagctgg tgatgaatgc tactctcaag    3060
gactgtgacc tgccagcagc tgacagctgc gccatcatgg aaggcgagga tgtagaggac    3120
gacctcatct ttaccagcaa gaagtcactc tttgggaaga tcaaatcatt tacctccaag    3180
cagccagctc ctgtcaccat ctctctttca gaggactcct gatggatttg actcagtgcc    3240
gctgaagaca tcctcaggag gcccagacat ggacctgtga gaggcactgc ctgcctcacc    3300
tgcctcctca ccttgcatag caccttttgca agcctgcggc gatttgggtg ccagcatcct    3360
gcaacaccca ctgctggaaa tctcttcatt gtggccttat cagatgtttg aatttcagat    3420 cttttttat agagtaccca aaccctcctt tctgcttgcc tcaaacctgc caaatatacc    3480
cacactttgt ttgtaaatta tgcccttgct tgtatcttgt ttcccaaaat ggcccatccg    3540
ccagagccat agcttcgtct gctcataatt cttatagctt tggaatgaaa atatttctat    3600
cttcttaagt atagaaacta tttcctctgt cctctaactt aagggcagaa acagctggga    3660
gttttcctcg catgccctca gctcatgatc tcttcaggag agaggctggg tgaggagggt    3720
gtcggggttc cctggtggat aatcttcata gcagcctgga tccatttccc ctggataacc    3780
agctcaaagg gagtgaaaat ggtagtctga gggcaagggg agcaaggcct gggtaagaaa    3840
agccttgaaa agcataaaaa gaggccgggc gcggtggctc acgcctgtaa tcccagcact    3900
ttgggaggcc gaggcgggca gatcatgagg tcggagatt gagaccatcc tggctaacac    3960
ggtgaaaccc cgtctctact aaaaatacaa aaaattagcc gggcgtggtg gcgggtgcct    4020
gtagtcccag ctactcggga ggctgaggcg ggagaatagc gtgaacctgg aaggcggagc    4080
ttgcagtgag ccgagatcgc gccactgcac tccatccagc ctgggtgaca gagtgagact    4140
ctgcctcaaa aaaaaaaaa aaaagaaaa gcacaaagag aggcaacaag gaatgttttt    4200 gttttgaga caggctctca ctctgtcacc taggctggag tgcagtggca taatcactgt    4260
tcagtgcagc ctcaagctct tgggctcaag ctatcctccc atctcaacct ctcaagtagc    4320
taggactaca agtgtgcacc accaggctca ctaatttta tattttttgt agacacaggg    4380
tttcaccatg ttgcccaggc tggtctccaa ctcctgggct caagtgatct gtccgcctca    4440
gcctcccaaa ctgctgggat tacaggcata agccactgca ctcagccttt tatttgtttt    4500 ttaaccacg tagctcattg ccttctctta agtaaatgat agatattctc actgaagcca    4560
aaggaataag ttcatcaaga aaatgcccaa agccctggtg gatacatcct ccctatcttt    4620
tttttaaacc ttccactatc actctatgac actgaaaaga accaggtaag ccccaaaccc    4680
agatgttcca gccttatcct ctattgggtt tacccacaga catagcaaac cctgtcagtg    4740
aggaaaattc cccatccttg agtgcccccg tcctagaagt ttgggccata ttatggaaca    4800
ggggtctctt atttgaaaag agcacaagga ggccaagatt ttaatggggc actttagggg    4860
atacagccca caatggcatg ggcctgaggt ggccgtgatg tctgcttcta agcttaacgc    4920
atctgctcag gcacagaata aacgtctagg ctggccaaaa aaggaactga atcccaggcc    4980
catacgccag caccagaatc aaaccagtct tcaaggaagg aaggctagga gagttttaaca    5040 agatttttcac tgggcccagc atggtggctc acacctgtaa tcccaaggca gaatggtggc    5100
ttgagctcag gagttcaaga ccagcctggg caacacagtg agaccctgtc tctaaaaaat    5160
ttaaaaataa acaaggtgtt caccaagctg ggatacttct cactattaag cccctatctt    5220
tctctttttt tcattctcaa ttgctttgtg tgataaaaaa ctaaagagac ttctggtcca    5280
atttctggca acatcccttc tgaaaggtga gtagagtggg tgtcttctat gcccatttc    5340
```

```
cccaattttta cacaaactat tatcaatgaa cttttaagta cctagaatgg gtaaaaccag    5400
agcaagactt taaattacct tcttctttct tctactggca gttctgcctc catcactatc    5460
aggctagggt gaccttccct tggtcaagcc ccaattgccc atgatttgtg cctgtgccct    5520
ttctccagtg accatttggt gaccagatgg tagatataga aagggatgg catttgcaag     5580 tgactagtct gccacaaaat gctcatctga ttagccactg ctgccctggc aatggctttg    5640
taagagtcaa tgagaactag agccaggctg tggtccctgg ccatcaacag tgttggtgac    5700
ggcagggagt ccctttggtt taataaatcc agttttttct tgggtatcca aattctcccc    5760
tccttttgta ggagtcaggc tctcagaacc tgtgtccatg ttggaacttc ccccagtgtg    5820
gatgcagata cgcagctcct gagctccagc ctaaagtctt ctgtagcctc agcaatactt    5880
gggcacctgc tgtctcactg aatagctttc ttttgtgaca aaggccacag acagccctta    5940
gactattccg gaaacagtag gaaaaattac atatgtcttt gacttcttta ttctgactcc    6000
actgatttta gccataatac tttaaggagc tacttttttac tacccttac cgtgctgact    6060 tctgcaggtc tgccctgtga cctgtcagga actcctgagt tacgctactg gggtcacctg    6120
ttgctcccct agcaagttag gcatgtcata tattttaac agcttatttg agatataatt     6180
cacatattat acaattcacc tttaaaacat acgattcaat ggttttcagc aaactcacag    6240
agttgtccgc ccacttgaga gcaaacacat gttcaatttt cttttccttt ttttttttga    6300
gacagagtca gctttgtcgc ccaggctgga gtgcagtgcc atgatcttgg ctcactgcag    6360
cctccccatc ctgggttcaa gtgatccttc tgcttcagcc tccccagtag ctgggattac    6420
aagcatgcgc caccacgcct agctaatttt tgtgttttta gtagagatgg ggtttcacca    6480
tgttggccag gctggtctca aactcctgga ctcaagtgat ccaccacct cggcctccca     6540 aagtgctggg attacaggtg taagccaccg tgcctggcct acgtgttcaa ttttctatga    6600
acaaaggctt tagtccttga cccagggcta agtggtctg tccaagctgt tgttggtaga     6660
gggagtatga taaaatgttt aaatctcatt tggttacctt gagtcctgga acatgcagta    6720
actgtcatgc tatagtcatc atctgtattt ggctgggaat acaaatgaag attgtggtgt    6780
attcaagcag tagggttttt gcttttgttt ttgttttagt gccaacaaaa ctttttttg     6840 tctgactaca ttaaagataa gactgactat atttatacaa cagaaacttt gtaatagatt    6900
ttttcagctt tgtgaaatcg aattttttt catcagggct ggttggattt ccttttacc     6960 ctgtaatcca agcgttaata gtttgttaga agatgggtta ttgcatgtca ctttttttt    7020 ttgtaaaata aaaacatacc ttac                                           7044

<210> SEQ ID NO 13
<211> LENGTH: 7043
<212> TYPE: DNA
<213> ORGANISM: Homo sapiens

<400> SEQUENCE: 13
acccgcaggt gagctgcaga ggcgcgcgtg gtccctgccc cacccgcgcg gagccagaga      60
ggaggcggtt gtcaaggcga cgtggaagca gcagccgcag cacctgagcc gctactgccg     120
ctcactcagg acaacgctat ggctgagcct gggcacagcc accatctctc cgccagagtc    180
aggggaagaa ctgagaggcg cataccccgg ctgtggcggc tgctgctctg ggctgggacc    240
gccttccagg tgacccaggg aacgggaccg gagcttcatg cctgcaaaga gtctgagtac    300
cactatgagt acacgcgtgt gacagcacg ggttccaggt ggagggtcgc cgtgccgcat     360
accccgggcc tgtgcaccag cctgcctgac cccgtcaagg gcaccgagtg ctccttctcc    420
```

```
tgcaacgccg gggagtttct ggatatgaag gaccagtcat gtaagccatg cgctgagggc    480
cgctactccc tcggcacagg cattcggttt gatgagtggg atgagctgcc ccatggcttt    540
gccagcctct cagccaacat ggagctggat gacagtgctg ctgagtccac cgggaactgt    600
acttcgtcca gtgggttccc cggggcgac tacatcgcct ccaacacgga cgaatgcaca    660
gccacactga tgtacgccgt caacctgaag caatctggca ccgttaactt cgaatactac    720
tatccagact ccagcatcat ctttgagttt ttcgttcaga atgaccagtg ccagcccaat    780
gcagatgact ccaggtggat gaagaccaca gagaaggat gggaattcca cagtgtggag    840
ctaaatcgag gcaataatgt cctctattgg agaaccacag ccttctcagt atggaccaaa    900
gtacccaagc ctgtgctggt gagaaacatt gccataacag gggtggccta cacttcagaa    960
tgcttcccct gcaaacctgg cacgtatgca gacaagcagg gctcctcttt ctgcaaactt   1020
tgcccagcca actcttattc aaataaagga gaaacttctt gccaccagtg tgaccctgac   1080
aaatactcag agaaaggatc ttcttcctgt aacgtgcgcc cagcttgcac agacaaagat   1140
tatttctaca cacacggc ctgcgatgcc aacggagaga cacaactcat gtacaaatgg   1200
gccaagccga aaatctgtag cgaggacctt gaggggcag tgaagctgcc tgcctctggt   1260
gtgaagaccc actgcccacc ctgcaaccca ggcttcttca aaaccaacaa cagcacctgc   1320
cagccctgcc catatggttc ctactccaat ggctcagact gtacccgctg ccctgcaggg   1380
actgaacctg ctgtgggatt tgaatacaaa tggtggaaca cgctgcccac aaacatggaa   1440
acgaccgttc tcagtgggat caacttcgag tacaagggca tgacaggctg ggaggtggct   1500
ggtgatcaca tttacacagc tgctggagcc tcagacaatg acttcatgat tctcactctg   1560
gttgtgccag gatttagacc tccgcagtcg gtgatggcag acacagagaa taagaggtg   1620 gccagaatca catttgtctt tgagaccctc tgttctgtga actgtgagct ctacttcatg   1680
gtgggtgtga attctaggac caacactcct gtggagacgt ggaaaggttc caaaggcaaa   1740
cagtcctata cctacatcat tgaggagaac actaccacga gcttcacctg ggccttccag   1800
aggaccactt tcatgaggc aagcaggaag tacaccaatg acgttgccaa gatctactcc   1860
atcaatgtca ccaatgttat gaatggcgtg gcctcctact gccgtccctg tgccctagaa   1920
gcctctgatg tgggctcctc ctgcacctct tgtcctgctg gttactatat tgaccgagat   1980
tcaggaacct gccactcctg ccccctaac acaattctga agcccacca gcttatggt   2040 gtccaggcct gtgtgccctg tggtccaggg accagaaaca acaagatcca ctctctgtgc   2100
tacaatgatt gcaccttctc acgcaacact ccaaccagga cttcaacta caacttctcc   2160 gctttggcaa acaccgtcac tcttgctgga gggccaagct tcacttccaa agggttgaaa   2220
tacttccatc actttaccct cagtctctgt ggaaaccagg gtaggaaaat gtctgtgtgc   2280
accgacaatg tcactgacct ccggattcct gagggtgagt cagggttctc caaatctatc   2340
acagcctacg tctgccaggc agtcatcatc ccccagagg tgacaggcta caaggccggg   2400
gtttcctcac agcctgtcag ccttgctgat cgacttattg gggtgacaac agatatgact   2460
ctggatggaa tcacctcccc agctgaactt ttccacctgg agtccttggg aataccggac   2520
gtgatcttct tttataggtc caatgatgtg acccagtcct gcagttctgg gagatcaacc   2580
accatccgcg tcaggtgcag tccacagaaa actgtccctg gaagtttgct gctgccagga   2640
acgtgctcag atgggacctg tgatggctgc aacttccact tcctgtggga gagcgcggct   2700 gcttgccgc tctgctcagt ggctgactac catgctatcg tcagcagctg tgtggctggg   2760
atccagaaga ctacttacgt gtggcgagaa cccaagctat gctctggtgg catttctctg   2820
```

```
cctgagcaga gagtcaccat ctgcaaaacc atagatttct ggctgaaagt gggcatctct    2880
gcaggcacct gtactgccat cctgctcacc gtcttgacct gctacttttg gaaaagaat     2940 caaaaactag agtacaagta ctccaagctg gtgatgaatg ctactctcaa ggactgtgac    3000
ctgccagcag ctgacagctg cgccatcatg gaaggcgagg atgtagagga cgacctcatc    3060
tttaccagca agaagtcact ctttgggaag atcaaatcat ttacctccaa ggtgtctggg    3120
tccagtcctt tgggagctga atcatagttc agtctcagct gttccccact gagcaattct    3180
gagctgggag ggctggcttt gtgtgggtgg aggactcctg atggatttga ctcagtgccg    3240
ctgaagacat cctcaggagg cccagacatg gacctgtgag aggcactgcc tgcctcacct    3300
gcctcctcac cttgcatagc acctttgcaa gcctgcggcg atttgggtgc cagcatcctg    3360
caacacccac tgctgaaaat ctcttcattg tggccttatc agatgtttga atttcagatc    3420 ttttttttata gagtacccaa accctccttt ctgcttgcct caaacctgcc aaatataccc    3480
acactttgtt tgtaaattat gcccttgctt gtatcttgtt tcccaaaatg gcccatccgc    3540
cagagccata gcttcgtctg ctcataattc ttatagcttt ggaatgaaaa tatttctatc    3600
ttcttaagta tagaaactat ttcctctgtc ctctaactta agggcagaaa cagctgggag    3660
ttttcctcgc atgccctcag ctcatgatct cttcaggaga gaggctgggt gaggagggtg    3720
tcggggttcc ctggtggata atcttcatag cagcctggat ccatttcccc tggataacca    3780
gctcaaaggg agtgaaaatg gtagtctgag ggcaagggga gcaaggcctg ggtaagaaaa    3840
gccttgaaaa gcataaaaag aggccgggcg cggtggctca cgcctgtaat cccagcactt    3900
tgggaggccg aggcgggcag atcatgaggt cgggagattg agaccatcct ggctaacacg    3960
gtgaaacccc gtctctacta aaaatacaaa aaattagccg ggcgtggtgg cgggtgcctg    4020
tagtcccagc tactcgggag gctgaggcgg gagaatagcg tgaacctgga aggcggagct    4080
tgcagtgagc cgagatcgcg ccactgcact ccatccagcc tgggtgacag agtgagactc    4140
tgcctcaaaa aaaaaaaaaa aaagaaaag cacaaagaga ggcaacaagg aatgttttg     4200 ttttgagac aggctctcac tctgtcacct aggctggagt gcagtggcat aatcactgtt    4260
cagtgcagcc tcaagctctt gggctcaagc tatcctccca tctcaacctc tcaagtagct    4320
aggactacaa gtgtgcacca ccaggctcac taattttat attttttgta gacacagggt    4380
ttcaccatgt tgcccaggct ggtctccaac tcctgggctc aagtgatctg tccgcctcag    4440
cctcccaaac tgctgggatt acaggcataa gccactgcac tcagccttt atttgttttt     4500 taaccacgt agctcattgc cttctcttaa gtaaatgata gatattctca ctgaagccaa    4560
aggaataagt tcatcaagaa aatgcccaaa gccctggtgg atacatcctc cctatctttt    4620
ttttaaacct tccactatca ctctatgaca ctgaaaagaa ccaggtaagc cccaaaccca    4680
gatgttccag ccttatcctc tattgggttt acccacagac atagcaaacc ctgtcagtga    4740
ggaaaattcc ccatccttga gtgccccccgt cctagaagtt tgggccatat tatgaacag     4800 gggtctctta tttgaaaaga gcacaaggag gccaagattt taatgggca ctttagggga     4860 tacagcccac aatggcatgg gcctgagtg gccgtgatgt ctgcttctaa gcttaacgca    4920
tctgctcagg cacagaataa acgtctaggc tggccaaaaa aggaactgaa tcccaggccc    4980
atacgccagc accagaatca aaccagtctt caaggaagga aggctaggag agtttaacaa    5040
gattttcact gggcccagca tggtggctca cacctgtaat cccaaggcag aatggtggct    5100
tgagctcagg agttcaagac cagcctgggc aacacagtga gaccctgtct ctaaaaaatt    5160
taaaaataaa caaggtgttc accaagctgg gatacttctc actattaagc ccctatcttt    5220
```

```
ctctttttttt cattctcaat tgctttgtgt gataaaaaac taaagagact tctggtccaa      5280
tttctggcaa catcccttct gaaaggtgag tagagtgggt gtcttctatg cccatttttcc     5340 ccaattttac acaaactatt atcaatgaac ttttaagtac ctagaatggg taaaaccaga      5400
gcaagacttt aaattacctt cttctttctt ctactggcag ttctgcctcc atcactatca     5460
ggctagggtg accttccctt ggtcaagccc caattgccca tgatttgtgc ctgtgccctt     5520
tctccagtga ccatttggtg accagatggt agatatagaa aggggatggc atttgcaagt     5580
gactagtctg ccacaaaatg ctcatctgat tagccactgc tgccctggca atggctttgt     5640
aagagtcaat gagaactaga gccaggctgt ggtccctggc catcaacagt gttggtgacg     5700
gcagggagtc cctttggttt aataaatcca gttttctttt gggtatccaa attctcccct     5760
ccttttgtag gagtcaggct ctcagaacct gtgtccatgt tggaacttcc cccagtgtgg     5820
atgcagatac gcagctcctg agctccagcc taaagtcttc tgtagcctca gcaatacttg     5880
ggcacctgct gtctcactga atagcttctt tttgtgacaa aggccacaga cagcccttag     5940
actattccgg aaacagtagg aaaaattaca tatgtctttg acttctttat tctgactcca     6000
ctgattttag ccataatact ttaaggagct acttttact accccttacc gtgctgactt      6060
ctgcaggtct gccctgtgac ctgtcaggaa ctcctgagtt acgctactgg ggtcacctgt     6120
tgctccccta gcaagttagg catgtcatat attttttaaca gctttattga gatataattc    6180
acatattata caattcacct ttaaaacata cgattcaatg gttttcagca aactcacaga    6240
gttgtccgcc cacttgagag caaacacatg ttcaattttc ttttccttttt tttttttgag   6300 acagagtcag ctttgtcgcc caggctggag tgcagtgcca tgatcttggc tcactgcagc    6360
ctccccatcc tgggttcaag tgatccttct gcttcagcct ccccagtagc tgggattaca    6420
agcatgcgcc accacgccta gctaattttt gtgttttag tagagatggg gtttcaccat     6480
gttggccagg ctggtctcaa actcctggac tcaagtgatc cacccacctc ggcctcccaa    6540
agtgctggga ttacaggtgt aagccaccgt gcctggccta cgtgttcaat tttctatgaa    6600
caaaggcttt agtccttgac ccagggctaa agtggtctgt ccaagctgtt gttggtagag    6660
ggagtatgat aaaatgttta aatctcattt ggttaccttg agtcctggaa catgcagtaa    6720
ctgtcatgct atagtcatca tctgtatttg gctgggaata caaatgaaga ttgtggtgta    6780
ttcaagcagt agggttttg ctttttgttt tgttttagtg ccaacaaaac tttttttttgt    6840 ctgactacat taaagataag actgactata tttatacaac agaaactttg taatagattt    6900
tttcagcttt gtgaaatcga atttttttc atcagggctg gttggatttc cttttaccc      6960 tgtaatccaa gcgttaatag tttgttagaa gatgggttat tgcatgtcac ttttttttt    7020 tgtaaaataa aaacataccct tac                                            7043

<210> SEQ ID NO 14
<211> LENGTH: 7044
<212> TYPE: DNA
<213> ORGANISM: Homo sapiens

<400> SEQUENCE: 14
tgtcaaggcg acgtgggtag gaggagagga cagagggagg aggaaggatg ggcggtgttg        60
gcgtagccgc agggaggtga ctgaagcgag cctggcctct tgcatcctcc gcctgtgtac       120
ctccctcccc ttttttttccg ccttctgcca gcagaagcag cagccgcagc acctgagccg     180
ctactgccgc tcactcagga caacgctatg gctgagcctg gcacagcca ccatctctcc       240 gccagagtca ggggaagaac tgagaggcgc atacccggc tgtggcggct gctgctctgg      300
```

```
gctgggaccg ccttccaggt gacccaggga acgggaccgg agcttcatgc ctgcaaagag    360
tctgagtacc actatgagta cacggcgtgt gacagcacgg gttccaggtg gagggtcgcc    420
gtgccgcata ccccgggcct gtgccaccagc ctgcctgacc ccgtcaaggg caccgagtgc   480
tccttctcct gcaacgccgg ggagtttctg gatatgaagg accagtcatg taagccatgc    540
gctgagggcc gctactccct cggcacaggc attcggtttg atgagtggga tgagctgccc    600
catggctttg ccagcctctc agccaacatg gagctggatg acagtgctgc tgagtccacc    660
gggaactgta cttcgtccaa gtgggttccc cggggcgact acatcgcctc caacacggac    720
gaatgcacag ccacactgat gtacgccgtc aacctgaagc aatctggcac cgttaacttc    780
gaatactact atccagactc cagcatcatc tttgagtttt tcgttcagaa tgaccagtgc    840
cagcccaatg cagatgactc caggtggatg aagaccacag agaaaggatg ggaattccac    900
agtgtggagc taaatcgagg caataatgtc ctctattgga gaaccacagc cttctcagta    960
tggaccaaag tacccaagcc tgtgctggtg agaaacattg ccataacagg ggtggcctac   1020
acttcagaat gcttcccctg caaacctggc acgtatgcag acaagcaggg ctcctctttc   1080
tgcaaacttt gcccagccaa ctcttattca aataaaggag aaacttcttg ccaccagtgt   1140
gaccctgaca atactcaga  gaaaggatct tcttcctgta acgtgcgccc agcttgcaca   1200
gacaaagatt atttctacac acacgggcc tgcgatgcca acggagagac acaactcatg    1260
tacaaatggg ccaagccgaa aatctgtagc gaggaccttg aggggcagt gaagctgcct    1320
gcctctggtg tgaagaccca ctgcccaccc tgcaacccag gcttcttcaa aaccaacaac   1380
agcacctgcc agccctgccc atatggttcc tactccaatg gctcagactg tacccgctgc   1440
cctgcaggga ctgaacctgc tgtgggattt gaatacaaat ggtggaacac gctgcccaca   1500
aacatggaaa cgaccgttct cagtgggatc aacttcgagt acaagggcat gacaggctgg   1560
gaggtggctg tgatcacat ttacacagct gctggagcct cagacaatga cttcatgatt   1620
ctcactctgg ttgtgccagg atttagacct ccgcagtcgg tgatggcaga cacagagaat   1680
aaagaggtgg ccagaatcac atttgtcttt gagaccctct gttctgtgaa ctgtgagctc   1740
tacttcatgg tgggtgtgaa ttctaggacc aacactcctg tggagacgtg gaaaggttcc   1800
aaaggcaaac agtcctatac ctacatcatt gaggagaaca ctaccacgag cttcacctgg   1860
gccttccaga ggaccacttt tcatgaggca agcaggaagt acaccaatga cgttgccaag   1920
atctactcca tcaatgtcac caatgttatg aatggcgtgg cctcctactg ccgtccctgt   1980
gccctagaag cctctgatgt gggctcctcc tgcacctctt gtcctgctgg ttactatatt   2040
gaccgagatt caggaacctg ccactcctgc cccctaacaa cattctgaa  agcccaccag   2100
ccttatggtg tccaggcctg tgtgcccctgt ggtccaggga ccaagaacaa caagatccac   2160
tctctgtgct acaatgattg caccttctca cgcaacactc caaccaggac tttcaactac   2220
aacttctccg ctttggcaaa caccgtcact cttgctggag gccaagctt cacttccaaa   2280
gggttgaaat acttccatca ctttaccctc agtctctgtg gaaaccaggg taggaaaatg   2340
tctgtgtgca ccgacaatgt cactgacctc cggattcctg agggtgagtc agggttctcc   2400
aaatctatca cagcctacgt ctgccaggca gtcatcatcc ccccagaggt gacaggctac   2460
aaggccgggt ttcctcaca gcctgtcagc cttgctgatc gacttattgg ggtgacaaca   2520
gatatgactc tggatggaat cacctcccca gctgaacttt tccacctgga gtccttggga   2580
ataccggacg tgatcttctt ttataggtcc aatgatgtga cccagtcctg cagttctggg   2640
agatcaacca ccatccgcgt caggtgcagt ccacagaaaa ctgtccctgg aagtttgctg   2700
```

```
ctgccaggaa cgtgctcaga tgggacctgt gatggctgca acttccactt cctgtgggag    2760
agcgcggctg cttgcccgct ctgctcagtg gctgactacc atgctatcgt cagcagctgt    2820
gtggctggga tccagaagac tacttacgtg tggcgagaac ccaagctatg ctctggtggc    2880
atttctctgc ctgagcagag agtcaccatc tgcaaaacca tagatttctg gctgaaagtg    2940
ggcatctctg caggcacctg tactgccatc ctgctcaccg tcttgacctg ctactttggg    3000
aaaaagaatc aaaaactaga gtacaagtac tccaagctgg tgatgaatgc tactctcaag    3060
gactgtgacc tgccagcagc tgacagctgc gccatcatgg aaggcgagga tgtagaggac    3120
gacctcatct ttaccagcaa gaagtcactc tttgggaaga tcaaatcatt tacctccaag    3180
cagccagctc ctgtcaccat ctctctttca gaggactcct gatggatttg actcagtgcc    3240
gctgaagaca tcctcaggag gcccagacat ggacctgtga gaggcactgc ctgcctcacc    3300
tgcctcctca ccttgcatag cacctttgca agcctgcggc gatttgggtg ccagcatcct    3360
gcaacaccca ctgctggaaa tctcttcatt gtggccttat cagatgtttg aatttcagat    3420
ctttttttat agagtaccca aaccctcctt tctgcttgcc tcaaacctgc caaatatacc    3480
cacactttgt ttgtaaatta tgcccttgct tgtatcttgt ttcccaaaat ggcccatccg    3540
ccagagccat agcttcgtct gctcataatt cttatagctt tggaatgaaa atatttctat    3600
cttcttaagt atagaaacta tttcctctgt cctctaactt aagggcagaa acagctggga    3660
gttttcctcg catgccctca gctcatgatc tcttcaggag agaggctggg tgaggagggt    3720
gtcggggttc cctggtggat aatcttcata gcagcctgga tccatttccc ctggataacc    3780
agctcaaagg gagtgaaaat ggtagtctga gggcaagggg agcaaggcct gggtaagaaa    3840
agccttgaaa agcataaaaa gaggccgggc gcggtggctc acgcctgtaa tcccagcact    3900
ttgggaggcc gaggcgggca gatcatgagg tcggagattg agaccatcc tggctaacac    3960 ggtgaaaccc cgtctctact aaaaatacaa aaaattagcc gggcgtggtg gcgggtgcct    4020
gtagtcccag ctactcggga ggctgaggcg ggagaatagc gtgaacctgg aaggcggagc    4080
ttgcagtgag ccgagatcgc gccactgcac tccatccagc ctgggtgaca gagtgagact    4140
ctgcctcaaa aaaaaaaaaa aaaagaaaa gcacaaagag aggcaacaag gaatgttttt    4200
gtttttgaga caggctctca ctctgtcacc taggctggag tgcagtggca taatcactgt    4260
tcagtgcagc ctcaagctct gggctcaag ctatcctccc atctcaacct ctcaagtagc    4320
taggactaca agtgtgcacc accaggctca ctaattttta tattttttgt agacacaggg    4380
tttcaccatg ttgcccaggc tggtctccaa ctcctgggct caagtgatct gtccgcctca    4440
gcctcccaaa ctgctgggat tacaggcata agccactgca ctcagccttt tatttgtttt    4500 ttaaccacg tagctcattg ccttctctta agtaaatgat agatattctc actgaagcca    4560
aaggaataag ttcatcaaga aaatgcccaa agccctggtg gatacatcct ccctatcttt    4620
tttttaaacc ttccactatc actctatgac actgaaaaga accaggtaag ccccaaaccc    4680
agatgttcca gccttatcct ctattgggtt tacccacaga catagcaaac cctgtcagtg    4740
aggaaaattc cccatccttg agtgcccccg tcctagaagt ttgggccata ttatggaaca    4800
ggggtctctt atttgaaaag agcacaagga ggccaagatt ttaatggggc actttagggg    4860
atacagccca caatggcatg ggcctgaggt ggccgtgatg tctgcttcta agcttaacgc    4920
atctgctcag gcacagaata aacgtctagg ctggccaaaa aaggaactga atcccaggcc    4980
catacgccag caccagaatc aaaccagtct tcaaggaagg aaggctagga gagtttaaca    5040
agattttcac tgggcccagc atggtggctc acacctgtaa tcccaaggca gaatggtggc    5100
```

```
ttgagctcag gagttcaaga ccagcctggg caacacagtg agaccctgtc tctaaaaaat    5160
ttaaaaataa acaaggtgtt caccaagctg ggatacttct cactattaag cccctatctt    5220
tctctttttt tcattctcaa ttgctttgtg tgataaaaaa ctaaagagac ttctggtcca    5280
atttctggca acatcccttc tgaaaggtga gtagagtggg tgtcttctat gcccattttc    5340 cccaattttta cacaaactat tatcaatgaa cttttaagta cctagaatgg gtaaaaccag    5400
agcaagactt taaattacct tcttctttct tctactggca gttctgcctc catcactatc    5460
aggctagggt gaccttccct tggtcaagcc ccaattgccc atgatttgtg cctgtgccct    5520
ttctccagtg accatttggt gaccagatgg tagatataga aaggggatgg catttgcaag    5580
tgactagtct gccacaaaat gctcatctga ttagccactg ctgccctggc aatggctttg    5640
taagagtcaa tgagaactag agccaggctg tggtccctgg ccatcaacag tgttggtgac    5700
ggcagggagt ccctttggtt taataaatcc agttttttctt tgggtatcca aattctcccc    5760
tccttttgta gggagtcaggc tctcagaacc tgtgtccatg ttggaacttc ccccagtgtg    5820
gatgcagata cgcagctcct gagctccagc ctaaagtctt ctgtagcctc agcaatactt    5880
gggcacctgc tgtctcactg aatagctttc ttttgtgaca aaggcacag acagcccta    5940 gactattccg gaaacagtag gaaaaattac atatgtcttt gacttcttta ttctgactcc    6000
actgatttta gccataatac tttaaggagc tacttttttac taccccttac cgtgctgact    6060
tctgcaggtc tgccctgtga cctgtcagga actcctgagt tacgctactg gggtcacctg    6120
ttgctcccct agcaagttag gcatgtcata tatttttaac agcttattg agatataatt    6180 cacatattat acaattcacc tttaaaacat acgattcaat ggttttcagc aaactcacag    6240
agttgtccgc ccacttgaga gcaaacacat gttcaatttt ctttctctttt tttttttga    6300 gacagagtca gctttgtcgc ccaggctgga gtgcagtgcc atgatcttgg ctcactgcag    6360
cctccccatc ctgggttcaa gtgatccttc tgcttcagcc tccccagtag ctgggattac    6420 aagcatcgc caccacgcct agctaatttt tgtgttttta gtagagatgg ggtttcacca    6480
tgttggccag gctggtctca aactcctgga ctcaagtgat ccaccccacct cggcctccca    6540 aagtgctggg attacaggtg taagccaccg tgcctggcct acgtgttcaa ttttctatga    6600
acaaaggctt tagtccttga cccagggcta aagtggtctg tccaagctgt tgttggtaga    6660
gggagtatga taaaatgttt aaatctcatt tggttacctt gagtcctgga acatgcagta    6720
actgtcatgc tatagtcatc atctgtatttt ggctgggaat acaaatgaag attgtggtgt    6780
attcaagcag tagggttttt gcttttgttt ttgttttagt gccaacaaaa cttttttttg    6840
tctgactaca ttaaagataa gactgactat atttatacaa cagaaacttt gtaatagatt    6900
ttttcagctt tgtgaaatcg aatttttttt catcagggct ggttggattt ccttttttacc    6960 ctgtaatcca agcgttaata gtttgttaga agatgggtta ttgcatgtca ctttttttt    7020 ttgtaaaata aaacatacc ttac                                            7044
```

```
<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
ggggacaagt ttgtacaaaa aagcaggctt c                                      31

<210> SEQ ID NO 16
```

```
<211> LENGTH: 29
<212> TYPE: DNA
<213> ORGANISM: Artificial Sequence
<220> FEATURE:
<223> OTHER INFORMATION: Primer

<400> SEQUENCE: 16
ggggaccact tgtacaaga aagctgggt                                              29

<210> SEQ ID NO 17
<211> LENGTH: 3428
<212> TYPE: DNA
<213> ORGANISM: Homo sapiens

<400> SEQUENCE: 17
cgcaggtgag ctgcagaggc gcgcgtggtc cctgccccac ccgcgcggac tccctcccct     60
ttttttccgc cttctgccag cagaagcagc agccgcagca cctgagccgc tactgccgct    120
cactcaggac aacgctatgg ctgagcctgg gcacagccac catctctccg ccagagtcag    180
gggaagaact gagaggcgca taccccggct gtggcggctg ctgctctggg ctgggaccgc    240
cttccaggtg acccagggaa cgggaccgga gcttcatgcc tgcaaagagt ctgagtacca    300
ctatgagtac acggcgtgtg acagcacggg ttccaggtgg agggtcgccg tgccgcatac    360
cccgggcctg tgcaccagcc tgcctgaccc cgtcaagggc accgagtgct ccttctcctg    420
caacgccggg gagtttctgg atatgaagga ccagtcatgt aagccatgcg ctgagggccg    480
ctactccctc ggcacaggca ttcggtttga tgagtgggat gagctgcccc atggctttgc    540
cagcctctca gccaacatgg agctggatga cagtgctgct gagtccaccg ggaactgtac    600
ttcgtccaag tgggttcccc ggggcgacta catcgcctcc aacacggacg aatgcacagc    660
cacactgatg tacgccgtca acctgaagca atctggcacc gttaacttcg aatactacta    720
tccagactcc agcatcatct ttgagttttt cgttcagaat gaccagtgcc agcccaatgc    780
agatgactcc aggtggatga agaccacaga gaaaggatgg gaattccaca gtgtggagct    840
aaatcgaggc aataatgtcc tctattggag aaccacagcc ttctcagtat ggaccaaagt    900
acccaagcct gtgctggtga aaacattgc ataacagggg tggcctaca cttcagaatg    960 cttcccctgc aaacctggca cgtatgcaga caagcagggc tcctcttcct gcaaactttg   1020
cccagccaac tcttattcaa ataaaggaga aacttcttgc caccagtgtg accctgacaa   1080
atactcagag aaaggatctt cttcctgtaa cgtgcgccca gcttgcacag acaaagatta   1140
tttctacaca cacacggcct gcgatgccaa cggagagaca caactcatgt acaaatgggc   1200
caagccgaaa atctgtagcg aggaccttga gggggcagtg aagctgcctg cctctggtgt   1260
gaagaccacc tgcccaccct gcaacccagg cttcttcaaa accaacaaca gcacctgcca   1320
gccctgccca tatggttcct actccaatgg ctcagactgt acccgctgcc ctgcagggac   1380
tgaacctgct gtgggatttg aatacaaatg gtggaacacg ctgccacaa acatggaaac   1440 gaccgttctc agtgggatca acttcgagta caagggcatg acaggctggg aggtggctgg   1500
tgatcacatt tacacagctg ctggagcctc agacaatgac ttcatgattc tcactctggt   1560
tgtgccagga tttagacctc cgcagtcggt gatggcagac acagagaata agaggtggc   1620 cagaatcaca tttgtctttg agaccctctg ttctgtgaac tgtgagctct acttcatggt   1680
gggtgtgaat tctaggacca acactcctgt ggagacgtgg aaaggttcca aggcaaaca   1740 gtcctatacc tacatcattg aggagaacac taccacgagc ttcacctggg ccttccagag   1800
gaccactttt catgaggcaa gcaggaagta caccaatgac gttgccaaga tctactccat   1860
```

```
caatgtcacc aatgttatga atggtgtggc ctcctactgc cgtccctgtg ccctagaagc  1920
ctctgatgtg ggctcctcct gcacctcttg tcctgctggt tactatattg accgagattc  1980
aggaacctgc cactcctgcc ccactaacac aattctgaaa gcccaccagc cttatggtgt  2040
ccaggcctgt gtgccctgtg gtccagggac caagaacaac aagatccact ctctgtgcta  2100
caacgattgc accttctcac gcaacactcc gaccaggact ttcaactaca acttctccgc  2160
tttggcaaac actgtcactc ttgctggagg gccaagcttc acttccaaag ggctgaaata  2220
cttccatcac tttaccctca gtctctgtgg aaaccagggt aggaaaatgt ctgtgtgcac  2280
cgacaatgtc actgacctcc ggattcctga gggtgagtca gggttctcca aatctatcac  2340
agcctacgtc tgccaggcag tcatcatccc cccagaggtg acaggctaca aggccggggt  2400
ttcctcacag cctgtcagcc ttgctgatcg acttattggg gtgacaacag atatgactct  2460
ggatggaatc acctccccag ctgaactttt ccacctggag tccttgggaa taccggacgt  2520
gatcttcttt tataggtcca atgatgtgac ccagtcctgc agttctggga gatcaaccac  2580
catccgcgtc aggtgcagtc cacagaaaac tgtccctgga agtttgctgc tgccaggaac  2640
gtgctcggat gggacctgtg atggctgcaa cttccacttc ctgtgggaga gcgcggctgc  2700
ttgcccgctc tgctcagtgg ctgactacca tgctatcgtc agcagctgtg tggctgggat  2760
ccagaagact acttacgtgt ggcgagaacc caagctatgc tctggtggca tttctctgcc  2820
tgagcagaga gtcaccatct gcaaaaccat agatttctgg ctgaaagtgg gcatctctgc  2880
aggcacctgt actgccatcc tgctcaccgt cttgacctgc tacttttgga aaagaatca  2940
aaaactagag tacaagtact ccaagctggt gatgaatgct actctcaagg actgtgacct  3000
gccagcagct gacagctgcg ccatcatgga aggcgaggat gtagaggacg acctcatctt  3060
taccagcaag aagtcactct ttgggaagat caaatcattt acctccaaga ggactcctga  3120
tggatttgac tcagtgccgc tgaagacatc ctcaggaggc ctagacatgg acctgtgaga  3180
ggcactgcct gcctcacctg cctcctcacc ttgcatagca cctttgcaag cctgcggcga  3240
tttgggtgcc agcatcctgc aacacccact gctggaaatc tcttcattgt ggccttatca  3300
gatgtttgaa tttcagatct tttttttatag agtacccaaa ccctcctttc tgcttgcctc  3360
aaacctgcca aatatacccca cactttgttt gtaaattaaa aaaaaaaaaa aaaaaaaaa  3420
aaaaaaaa                                                          3428
```

The invention claimed is:

1. A method of diagnosing melanoma in an individual, the method comprising detecting the level of Maba protein in a skin sample from the individual and diagnosing said individual as having melanoma when the level is elevated relative to a control Maba protein level established for normal skin, wherein the Maba protein comprises SEQ ID NO:2.

2. The method of claim 1, wherein the detecting comprises contacting the sample with an isolated antibody that selectively binds to the Maba protein and detecting binding of the antibody to the Maba protein.

3. The method of claim 2, wherein the antibody is coupled to a detectable substance.

* * * * *